US007884084B2

(12) United States Patent
Jockers et al.

(10) Patent No.: US 7,884,084 B2
(45) Date of Patent: Feb. 8, 2011

(54) OLIGONUCLEOTIDES WHICH INHIBIT EXPRESSION OF THE OB-RGRP PROTEIN

(75) Inventors: Ralf Jockers, Bures sur Yvette (FR); Cyril Couturier, Paris (FR); Eugen Uhlmann, Glashuetten (DE)

(73) Assignees: Aventis Pharma S.A., Antony (FR); Institut National de la Sante Et de la Recherche Medicale, Paris (FR); Centre National de la Rechercher Scientifique, Paris (FR)

( * ) Notice: Subject to any disclaimer, the term of this patent is extended or adjusted under 35 U.S.C. 154(b) by 0 days.

(21) Appl. No.: 10/774,721

(22) Filed: Feb. 9, 2004

(65) Prior Publication Data

US 2005/0009042 A1 Jan. 13, 2005

Related U.S. Application Data

(60) Provisional application No. 60/461,005, filed on Apr. 7, 2003.

(30) Foreign Application Priority Data

Feb. 10, 2003 (FR) .................................. 03 01543

(51) Int. Cl.
*C12N 15/11* (2006.01)

(52) U.S. Cl. .................................................... 514/44 A

(58) Field of Classification Search ................ 514/44 A
See application file for complete search history.

(56) References Cited

U.S. PATENT DOCUMENTS

| | | | | |
|---|---|---|---|---|
| 5,510,239 | A * | 4/1996 | Baracchini et al. | 435/6 |
| 5,789,198 | A * | 8/1998 | Akerblom | 435/69.1 |
| 5,801,154 | A * | 9/1998 | Baracchini et al. | 514/44 |
| 5,945,336 | A * | 8/1999 | Brown et al. | 435/375 |
| 5,998,148 | A * | 12/1999 | Bennett et al. | 435/6 |
| 6,010,852 | A * | 1/2000 | Hillman et al. | 435/6 |
| 2002/0044941 | A1* | 4/2002 | Rosen et al. | 424/184.1 |
| 2003/0166847 | A1* | 9/2003 | Bailleul et al. | 530/350 |
| 2003/0180756 | A1* | 9/2003 | Shi et al. | 435/6 |
| 2004/0259247 | A1* | 12/2004 | Tuschl et al. | 435/375 |
| 2005/0118625 | A1* | 6/2005 | Mounts | 435/6 |

FOREIGN PATENT DOCUMENTS

| | | |
|---|---|---|
| EP | 0969091 | 1/2000 |
| WO | WO 9401550 A1 * | 1/1994 |
| WO | WO 97/14191 | 7/1997 |

OTHER PUBLICATIONS

Taylor et al. (1999) Drug Discvery Today 4:562-567.*
Bailleul et al. (1997) Nuc. Acids Res. 25:2752-2758.*
STIC-Biotech Sequence search results (selected pages; 6 pages total).*
Jen et al. (2000) Stem Cells 18:307-319.*
Hannon and Rossi (2004) Nature 431:371-378.*
Yu et al. (2002) Proc. Natl. Acad. Sci. 99:6047-6052.*
Hannon (2002) Nature 418:244-251.*
Bennett et al. (1999) Biochimica Biophysica Acta 1489:19-30.*
Vickers et al. (2003) J. Biol. Chem. 278:7108-7118.*
A. Lundin et al., Expression and intracellular localization of leptin receptor long isofonn-GFG chimera, Biochimica et Biophysics Acata, vol. 1499, No. 1-2, pp. 130-138.
B. Bailleul et al., The leptin receptor promoter controls expression of a second distinct protein, Nucleic Acids Research, vol. 25, No. 14, Jul. 15, 1997, pp. 2752-2758.
K. Seron et al., OB-RGRP and Leprotl1 Define a New Familty of Lipid Raft-Associated Tetraspanning Membrane Proteins Localized At the TGN and/or Endosomes, Biology of the Cell, vol. 93, No. 3/4, Nov. 7, 2001, p. 227.
L. Tartaglia et al., Identification and Expression Cloning of a Leptin Receptor, OB-R, Cell, vol. 83, No. 7, Dec. 29, 1995, pp. 1263-1271.
N. Boute et al., Monitoring the Activation State of the Insulin Receptor Using Bioluminescence Resonance Energy Transfer, Molecular Pharmacology, vol. 60, No. 4, Oct. 2001, pp. 640-645.
N. Boute et al., The use of resonance energy transfer in high-throughput screening: BRET versus FRET, Trends in Pharmacological Sciences, vol. 213, No. 8, Aug. 2002, pp. 351-354.
T. Efferth, Leptin contributes to the protection of human leukemic cells from cisplatinum cytoxity, Anticancer Research, vol. 20, No. 4, Jul. 2000, pp. 2541-2546.
Y. Huang et al., Cloning and characterization of a novel leptin receptor overlapping transcript-like 1 gene (LEPROTL1)1, Biochimica et Biophysica Acta, vol. 1517, No. 2, Jan. 26, 2001, pp. 327-331.
Hideo Makimura et al., Reducing hypothalamic AGRP by RNA interference increases metabolic rate and decreases body weight without influencing food intake, BMC Neuroscience (2002, pp. 1-6).

* cited by examiner

*Primary Examiner*—J. E Angell

(57) ABSTRACT

The present application relates to antisense oligonucleotides which inhibit expression of the OB-RGRP protein and to uses thereof for preventing and/or treating leptin-related pathological conditions.

Figure 3A:
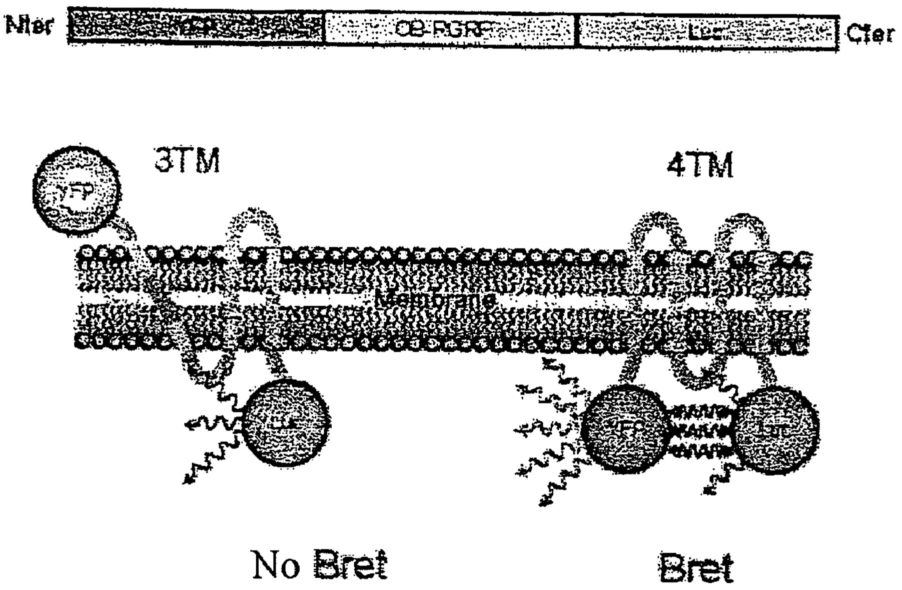

It also relates to a method for detecting compounds which modify the interaction between proteins of the OB-RGRP family and the leptin receptor. This detection may be carried out by measuring the energy transfer between fusion proteins composed of these proteins and of energy-donor and -acceptor proteins.

4 Claims, 13 Drawing Sheets

Figure 1:

| | |
|---|---|
| AS 01: | 3'-teg-G*G*G C*C*C*G G*C A*C*C G*T*C*C T*T*C*G |
| AS 02: | 3'-teg-G*G*G*T*C A A G*C*C*C T*C*T G*T A*C*C*G |
| AS 03: | 3'-teg-G*C*C*C T*C*T G*T A*C*C G*C*C*C G*C*A*A |
| AS 04: | 3'-teg-T*A*C*C G*C*C*C G*C A A*T*T*T*C G A*G*A |
| AS 05: | 3'-teg-T*T*C*G A G A*G*C A*C*C G*T A A*T A*G*G |
| AS 06: | 3'-teg-G*A*A*T A*C G A*C*C*C*T A*C A*C G G*A*A |
| AS 07: | 3'-teg-A*C*A*C G G A A*T*C*T C*C*T*A A*T A*C*C |
| AS 08: | 3'-teg-C*T*C*C*T A A*T A*C*C G*C A A*A*T G*A*C |
| AS 09: | 3'-teg-C*C*G*C*A A A*T G A*C*C*G G G A*A T*A*A |
| AS 10: | 3'-teg-A*C*G G A*C A G*C*C*C T*T*G A*C*C G*T*A |
| AS 11: | 3'-teg-G*G*A*C A G*C*C*C T*T*G A*C*C G*T A*T A*A*A |
| AS 12: | 3'-teg-G*C*C*C T*T*G A*C*C G*T A*T A A*A G*A*A |
| AS 13: | 3'-teg-G*G*A A*C*A*C A A*C*C*G T*C*C*G T*T*A*C |
| AS 14: | 3'-teg-T*G*T A*C A*C G*T G*T A*C G*C*C G*T A*A |
| AS 15: | 3'-teg-G*C*C*T C*C*T G*T C*C*A G*C*C*G C*C*A*A |
| AS 16: | 3'-teg-G*G*A*C*C G A*C*A T*T*G C*A*C G*T C*T A*A*A |

*: Thioester

__: 2'-O-Methylation teg: Triethylene glycol spacer

Figure 2

```
                          10        20        30        40        50        60
                           |         |         |         |         |         |
OB-RGRP_human     --------------MAG-VKALVALSFSGAIGLTFLMLGCALEDYGVYWPLFVLIFHAIS
My47_human        --------------MAG-IKALISLSFGGAIGLMFLMLGCALPIYNKYWPLFVLFFYILS
yt02_C.elegans    MCCHIHIQCFDCCSMKNTILAVAALAFAGVVGLTFLVLGCALPRYGTWTPMFVITFYVLS
YJ14_Yeast        ----------MMEFKVSPLTKIISLSGFLALGFLLVILSCAL--FHNYYPLFDILIFLLA
                                  . :  : :*:   .:*: :::*.***  :  : *:* : :. ::
Consensus         MCCHIHIQCF2222MAG2IKALI2LSF4GAIGLTFLMLGCALP3YG4YWPLFV24FY4LS

                          70        80        90       100       110       120
                           |         |         |         |         |         |
OB-RGRP_human     PIPHFIAKR-----VTYDSDATSSACRELAYFFTTGIVVSAFGFPVILARVAVIKWGACG
My47_human        PIPYCIARR-----LVDDTDAMSNACKELAIFLTTGIVVSAFGLPIVFARAHLIEWGACA
yt02_C.elegans    PVPLLIARR-----FQEDMTGTN-ACIELALFITTGIVISAFALPIVLAHAGTIAMSACF
YJ14_Yeast        PIPNTIFNAGNKYHTSDFMSDSSNTGQDLAHFLTGMLVTSGIALPVVFYHCQLIGHLSCI
                  *:*  * .              . :  :** *:*  :* *.:.:*::: :   *   :*
Consensus         PIP44IARRGNKYH44DDMDATSNAC4ELA4FLTTGIVVSAF2LP2V2A2A4LI4WGAC4

                         130       140       150
                           |         |         |
OB-RGRP_human     LVLAGNAVIFLTIQGFFLIFGRGDDFSWEQW-
My47_human        LVLTGNTVIFATILGFFLVFGSKDDFSWQQW-
yt02_C.elegans    LIFIANSINFSVIIFYFRIFNGEDMNGMSLW-
YJ14_Yeast        MCMIGGLIIYSSIVIFKWFFKKDFNEDDSLFG
                  : : .. : :  *  :  .*      . . :
Consensus         LVLIGN42IFSTI4GFFLIFG44DDFSWS2WG
```

Figure 4 A
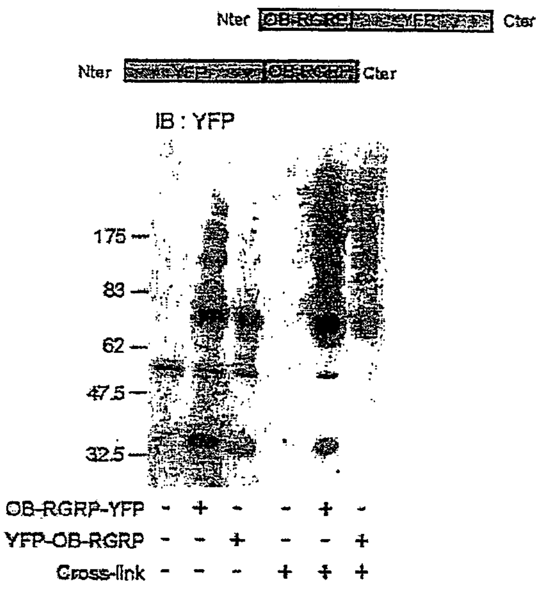
Figure 4B
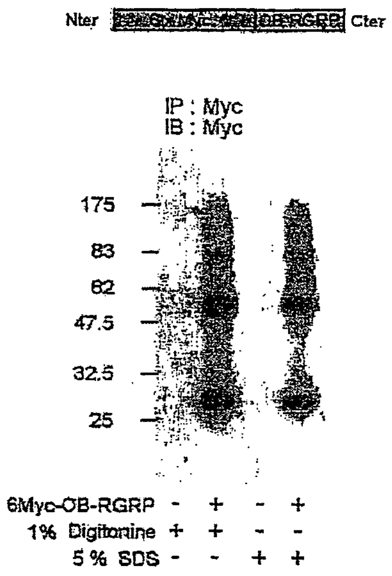

Figure 10a
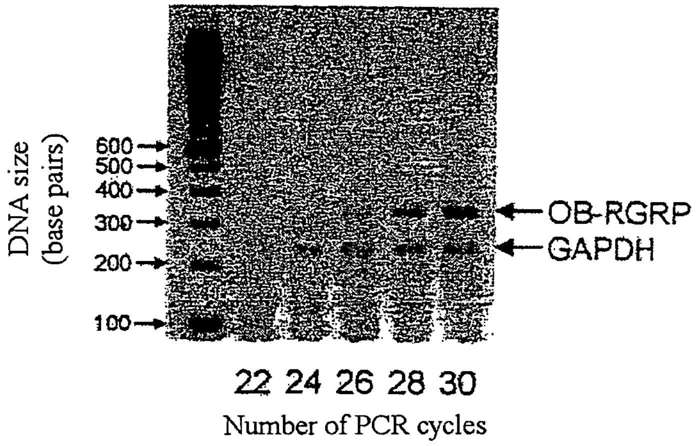
Figure 10b
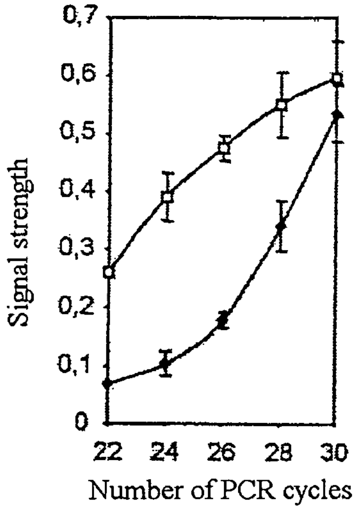
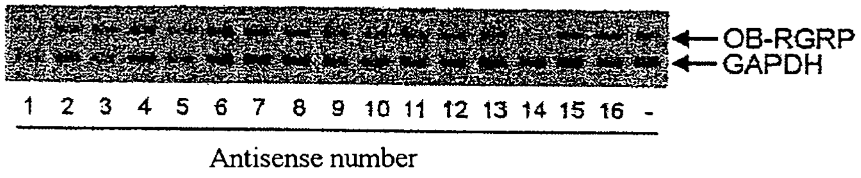
Figure 10c

FIGURE 11A
```
  5'- gugccugucgggaacuggcTT -3'
3'- TTcacggacagcccuugaccg -5'
```
FIGURE 11B
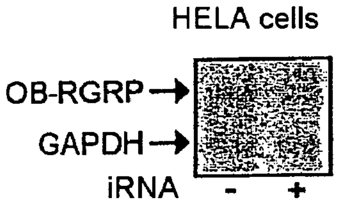
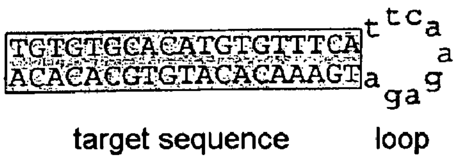
FIGURE 11C
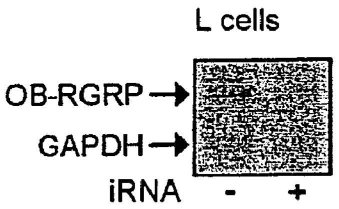
FIGURE 11D

OLIGONUCLEOTIDES WHICH INHIBIT EXPRESSION OF THE OB-RGRP PROTEIN

This application claims priority benefit to U.S. application Ser. No. 60/461,005, filed Apr. 7, 2003 and to French application number 0301543, filed Feb. 10, 2003.

The present application relates to oligonucleotides which inhibit expression of the OB-RGRP protein and to uses thereof for preventing and/or treating leptin-related pathological conditions.

It also relates to a method for detecting leptin receptor ligands using the energy transfer between, firstly, fusion proteins composed of leptin receptors and of energy-donor or -acceptor proteins and, secondly, fusion proteins composed of OB-RGRP or of MYO47 and of energy-donor or -acceptor proteins.

It also relates to fusion proteins for implementing this method.

Leptin is a 16 kDa protein secreted mainly by the adipose tissue, which binds to a receptor (OB-R) belonging to the cytokine receptor family. Five membrane-bound isoforms of this receptor have been identified, and derive from alternative splicing of the same gene. These isoforms which have the same extracellular and transmembrane domain are characterized by intracellular domains of varying sizes (Tartaglia et al (1995) Cell 83, 1263-1271). A soluble form of the receptor has also been identified and comes from an alternative splicing or a proteolytic cleavage of the extracellular domain of the membrane-bound forms. The short form of the receptor (OB-Rs), which appears to be involved in transporting leptin across the blood-brain barrier, is the most expressed isoform. The long form (OB-Rl) is only expressed in a few tissues, such as the hypothalmus, and appears to be responsible for most of the biological effects of leptin (Sweeney, G. (2002) Cell Signal 14, 655-663). Leptin and its receptor have been the subject of particular attention due to their involvement in the regulation of energy balance and of the metabolism, and in the neuroendocrine response to food intake. Recently, it has been shown that leptin is also involved in important addition functions, such as regulation of the bone mass, angiogenesis, cicatrization, thrombus formation, sexual maturation, hematopoiesis, the regulation of immunity and inflammation, fetal development and cancer. The administration of leptin to leptin-deficient organisms such as mice (ob/ob) and certain humans causes a decrease in the lipid mass in various tissues, such as the liver and the adipose tissue (Halaas et al. (1995) Science 269, 543-546, Pelleymounter et al. (1995) Science 269, 540-543, Campfield et al. (1995) Science 269, 546-549, Farooqi et al. (1999) N Engl J Med 341, 879-884). This treatment with leptin also improves the sensitivity to insulin and decreases the fatty mass in mice and humans exhibiting lipodistrophy (Shimomura et al. (1999) Nature 401, 73-76, Oral et al. (2002) New England Journal of Medicine 346, 570-578, Petersen et al. (2002) J Clin Invest 109, 1345-1350). Obese individuals are generally resistant to leptin. The reasons for this resistance are still poorly understood, but several mechanisms have been suggested: a deficiency in leptin transport across the blood-brain barrier, a deficiency in activation of OB-R or in the signaling by these receptors, and the overexpression of negative regulators such as SOCS3 and PTP-1B (Bjorbaek et al. (2000) J Biol Chem 275, 40649-40657, Cheng et al. (2002) Developmental Cell 2, 497-503, Cook and Unger (2002) Developmental Cell 2, 385-387). Understanding the mechanisms of resistance to leptin requires a more detailed characterization of the mechanisms involved in OB-R activation.

OB-R is constitutively associated with janus kinase 2 (JAK 2). The binding of JAK2 to the receptor is critical for the signaling by OB-R and has been proposed as being involved in stabilizing the OB-R receptor dimers. Activation by agonists is thought to cause a change in conformation in the juxtamembrane region of the cytoplasm tail of the OB-R. JAK2, which is constitutively linked to the box1 motif in this region, is activated by autophosphorylation and then phosphorylates the OB-Rl receptor but not the OB-Rs receptor. The phosphorylation of OB-Rl allows anchoring of STAT proteins, which bind to the receptor and are activated by phosphorylation of tyrosine. The activated STAT proteins dimerize and translocate into the nucleus in order to stimulate the transcription of genes via STAT response elements (Tartaglia (1997) J Biol Chem 272, 6093-6096).

Recently, a second promoter for the leptin receptor has been discovered. Interestingly, a second transcript is co-expressed with the OB-R messengers from this promoter. This transcript has been observed in several species, such as mice, rats, humans, yeast and *C. elegans* (Bailleul et al. (1997) Nucleic Acids Res 25, 2752-2758). In situ hybridization experiments confirm the coexpression of OB-R and of the associated gene in the brain of mice, including the hypothalamic regions involved in regulating body weight (Mercer et al., J Neuroendocrinol 2000 July; 12(7):649-55). The corresponding protein is composed of 131 amino acids and is called OB-R-gene related protein (OB-RGRP). This protein was the subject of patent application WO 98/05792.

The fact that OB-RGRP is expressed in yeast and nematodes, which are organisms lacking leptin receptors, indicates a more general role for OB-RGRP, supported by the deletion of this protein in yeast which causes a deficiency in transport of proteins from the golgi to the vacuoles (Belgareh-Touze et al. (2002) Molecular Biology Of The Cell 13, 1694-1708).

In 2002, a cDNA called MY047 was cloned from a human brain cDNA library (Huang et al. (2001) Biochimica et Biophysica acta. Gene structure and expression 327-331). This protein is also the subject of application EP 0 969 091. The function of the corresponding protein is still unknown. MY047 exhibits 68% homology with OB-RGRP, suggesting that these two proteins belong to the same family. Analysis of the sequences available for the human genome sequencing project shows that no other homolog exists.

The applicants have endeavored to determine the role of OB-RGRP and its relationships with leptin receptors.

They have thus shown the specificity of the interactions between OB-RGRP and the OBRs receptor.

They have also shown that it is possible to specifically modify the expression of leptin receptors at the cell surface using oligonucleotides directed against the leptin receptor gene associated protein (OB-RGRP).

A subject of the present application is therefore optionally modified oligonucleotides comprising from 8 to 50 nucleotides which hybridize specifically with the sequence SEQ ID No. 1 and which inhibit OB-RGRP expression.

Advantageously, these oligonucleotides promote the expression of leptin receptors at the cell surface.

Preferentially, these oligonucleotides are antisense oligonucleotides.

Preferentially, these oligonucleotides comprise a sequence exhibiting at least 60%, 70%, 80% or 90% identity with the sequence SEQ ID No. 2.

According to an advantageous embodiment, in these oligonucleotides, nucleotides are thioesterified.

According to another advantageous embodiment, in these oligonucleotides, nucleotides are 2'-O-methylated.

According to another advantageous embodiment, these oligonucleotides have a triethylene glycol residue at their 3' ends.

Although the most commonly used form of antisense compounds is in the form of antisense oligonucleotides, the present invention includes oligonucleotide derivatives and compounds which mimic their structure, such as those described hereinafter, without this list being limiting. The antisense compounds in agreement with this invention preferably comprise from 8 to 50 nucleobases (i.e. they are oligomers made up of 8 to 50 nucleotide units). The antisense compounds particularly targeted are antisense oligonucleotides, more specially those which are made up of approximately 12 to 30 nucleobases. The antisense compounds comprise ribozymes, oligozymes or other short catalytic RNAs or catalytic oligonucleotides which hybridize with the target nucleic acid and modulate its expression. A nucleoside is a combination of a nitrogenous base and a sugar. The base of a nucleoside is generally a heterocyclic nitrogenous base. The two most common types of heterocyclic base are purine and pyrimidine bases. The nucleotides are nucleosides which carry a phosphate group covalently bonded to the sugar of the nucleoside. For the nucleosides comprising a pentanofuranose, the phosphate may be bonded to the hydroxyl at position 2', 3' or 5' of the sugar. The formation of nucleotides comes from the covalent attachment of the phosphate group to two adjacent nucleosides, which makes it possible, step by step, to obtain a linear oligomer. The two ends of such a linear polymer can, in turn, join together to form a circular structure, but the open structure is generally preferred. In the nucleotide structure, the phosphate groups are considered to form the internucleoside skeleton of the oligonucleotide. The normal bond in the RNA or DNA skeleton is a 3'-5' phosphodiester linkage.

Specific examples of antisense compounds which can be used in this invention include oligonucleotides containing a modified backbone or unnatural internucleoside bonds. Thus, oligonucleotides with a modified backbone comprise those which conserve a phosphate atom in their skeleton and those which are lacking therein. For the needs of the present invention, modified oligonucleotides which do not have a phosphorus atom in their internucleoside bond can, nevertheless, be considered to be oligonucleotides. The backbone of these modified oligonucleotides may comprise, for example, the following groups: phosphorothioates, chiral phosphorothioates, phosphorodithioates, phosphotriesters, aminoalkylphosphotriesters, methyl and other alkyl phosphonates, including 3'-alkylene phosphonates, 5'-alkylene phosphonates and chiral phosphonates, phosphinates, phosphoramidates, including 3'-aminophosphoramidate and aminoalkylphosphoramidates, thionophosphoramidates, thionoalkylphosphonates, thionoalkylphosphotriesters, selenophosphates and borophosphates which form normal 3'-5' bonds, and analogs thereof which form 2'-5' bonds, and also those which exhibit a reverse polarity, i.e. comprising at least one internucleoside bond of the 3'-3', 5'-5' or 2'-2' type. The form of oligonucleotides having a reverse polarity which is preferentially used is that which has the first internucleoside bond in 3' is of the 3'-3' type. This corresponds to a single inverted nucleotide residue which may, moreover, be abasic, i.e. in which the heterocyclic nitrogenous base is missing or replaced with a hydroxyl group. The various forms (saline or free acid) are included in the field of this invention.

The backbone of the modified oligonucleotides lacking a phosphorus atom is preferentially made up of short alkyl or cycloalkyl chains, including derivatives thereof comprising one or more hetero atoms, acting as an internucleoside bond. This type of backbone may be based on a morpholino bond (partly consisting of the sugar of the nucleoside), on siloxane, on formacetyl and thioformacetyl, on methylene formacetyl and methylene thioformacetyl, on riboacetyl, on alkenes, on sulfamates, on sulfonate and sulfonamide, on methyleneimine and methylene hydrazine, on amide, and on any other group comprising various nitrogen, sulfur and oxygen atoms or methyl groups.

For other oligonucleotide analogs, the sugar and the internucleoside bond (i.e. the backbone) are replaced at the same time in the nucleotide structure with new groups. The heterocyclic nitrogenous base is conserved in order to ensure hybridization with the target nucleic acid. Such oligomeric compounds, PNAs (for Peptide Nucleic Acids), have shown an excellent capacity for hybridization. In these compounds, the skeleton of the oligonucleotide is replaced with an amide-based backbone, in particular with aminoethyl glycine, grafted directly or indirectly onto the nitrogenous bases. In addition, thorough teaching regarding these PNAs may be found in Nielsen et al., Science, 1991, 254, 1497.

The invention incorporates more particularly oligonucleotides with a phosphorothioate, amide and morpholine backbone, and the oligonucleotides with a hetero atom skeleton, more precisely:

$—CH_2—NH—O—CH_2—$ $—CH_2—N(CH_3)—O—CH_2—$ (called methylene(methylimino) or MMI skeleton)

$—CH_2—O—N(CH_3)—CH_2—$ $—CH_2—N(CH_3)—N(CH_3)—CH_2—$ $—O—N(CH_3)—CH_2—CH_2—$ (in which the phosphodiester bridge is: $O—P—O—CH_2$).

The modification of the oligonucleotides may also be carried on the sugars: the preferred substitutions are at position 2' (F; O-, N- or S-alkane, O-, N- or S-alkene or O-, N- or S-alkyne derivatives of length C1 to C11, which may or may not be substituted) in particular, the preferred derivatives are:

$O—[(CH_2)nO]m-CH_3$ $O—(CH_2)n-O—CH_3$ $O—(CH_2)n-NH_2$ $O—(CH_2)n-CH_3$ $O—(CH_2)n-O—NH_2$ $O—(CH_2)n-O—N[(CH_2)n-CH_3]_2$ in which n and m range from 1 to 10.

Other modifications of the 2' position include the following groups: aliphatic chains, which may or may not be substituted, of length C1 to C10, aryl chains, aryl-alkyl chains and alkyl-aryl chains; —SH, $—SCH_3$, —OCN, —Cl, —Br, —CN, $CF_3$, $—OCF_3$, $—SO_2CH_3$, $—ONO_2$, $—NO_2$, $—N_3$, $—NH_2$; substituted silyls; "reporter" groups; intercalating groups; RNA cleavage groups; group to improve the pharmacodynamic capacities of an oligonucleotide. The preferred modifications include the groups:

2'-methoxyethoxy ($2'-O—CH_2CH_2OCH_3$, also called 2'-O-(2-methoxyethyl) or 2'-MOE) (Martin et al., Helv. Chim. Acta, 1995, 78f 486-504) 2'-dimethylaminooxyethoxy ($O(CH_2)_2ON(CH_3)_2$, also called 2'-DMAOE;

2'-dimethylaminoethoxyethoxy ($2'-O—CH_2OCH_2—N(CH_2)_2$, also called 2'-dimethylaminoethoxyethyl or 2'-DMAEOE).

Another advantageous modification leads to the formation of LNAs (Locked Nucleic Acids) in which the hydroxyl at position 2' is attached to the carbon at position 3' or 4' of the sugar, then forming a sugar with a bicyclic structure. The preferred bridging occurs via a methyl or ethyl linkage between the 2' oxygen and the 4' carbon.

Other preferred substitutions at position 2' include:

—O—$CH_3$(2'-methoxy)

—O—$(CH_2)_3$—$NH_2$ (2'-aminopropoxy)

—$CH_2$—CH═$CH_2$ (2'-allyl)

—O—$CH_2$—CH═$CH_2$ (2'-O-allyl)

—F (2'-fluoro).

These modifications at 2' may be in the ribo (lower) or arabino (upper) position. The 2'-fluoro substituent is the preferred one in the arabino position.

Similar modifications may be made on other positions, in particular at position 3' of the sugar of the nucleotide at the 3'-terminal end or in the oligonucleotides with a 2'-5' backbone, and at position 5' of the sugar at the 5'-terminal end. The sugars of the oligonucleotides can also be replaced with analogs (for example a cyclobutyl can be substituted for a pentofuranyl).

The oligonucleotides can also comprise modifications or substitutions on the nucleobases (nitrogenous heterocyclic bases called "bases" by those skilled in the art). The natural (unmodified) bases are purines (adenine A and guanine G) and pyrimidines (cytosine C, thymine T and uracil U). Included among the modified bases are natural or synthetic molecules such as 5-methylcytosine, 5-hydroxymethylcytosine, xanthine, hypoxanthine, 2-aminoadenine; 6-methyl, 2-methyl and other alkyl derivatives of purine bases (A and G); 2-thio derivative (C, T and U); 5-halo derivative (U, C); 5-propynyl cytosine derivative (U and C); 6-azo derivative (U, T and C); 5-uracil; 4-thiouracil; 8-halo, 8-amino, 8-thiol, 8-thioalkyl, 8-hydroxyl and other adenines and guanine substituted at position 8; 5-halo (in particular 5-bromo), 5-trifluoromethyl and other uracils and cytosines substituted in position 5; 7-methylguanine and 7-methyladenine; 2-fluoroadenine; 2-aminoadenine; 8-azaguanine and 8-azaadenine; 7-deazaguanine and 7-deazaadenine; 3-deazaguanine and 3-deazaadenine. In the other modified bases, tricyclic pyrimidines are found such as phenoxazine cytidine (1H-pyrimido [5,4-b][1,4]benzoxazin-2-(3H)-one), phenothiazine cytidine (1H-pyrimido[5,4-b][1,4]benzothiazin-2(3H)-one), substituted phenoxazine cytidine (such as 9-(2-aminoethoxy)-H-pyrimido[5,4-b][1,4]benzoxazine-2(3H)-one), or carbazole cytidine (2H-pyrimido[4,5-b]indol-'2-one).

The modified bases comprise the compounds in which the purine or pyrimidine heterocycle is replaced with another heterocycle, for example 7-deazaadenine, 7-deazaguanosine, 2-aminopyridine or 2-pyridone (The Concise Encyclopedia Of Polymer Science And Engineering, pages 858-859, Kroschwitz, J. I., ed. John Wiley & Sons, 1990; Englisch et al., Angewandte Chemie, International Edition, 1991, 30, 613; Sanghvi, Y. S., Chapter 15, Antisense Research and Applications, pages 289-302, Crooke, S. T. and Lebleu, B., ed., CRC Press, 1993). Some of these modified bases may be of great value for increasing the affinity of the oligomeric compounds of the invention, such as pyrimidines substituted at position 5, azapyrimidines, or N- and O-substituted purines (such as 2-aminopropyladenine, 5-propynyl uracil, 5-propynyl cytosine). The substituted 5-methylcytosines have a positive effect on the stability of oligomer-nucleic acid duplexes (Sanghvi, Y. S., Crooke, S. T. and Lebleu, B., eds., Antisense Research and Applications, CRC Press, Boca Raton, 1993, pp. 276-278) and are the preferred substitution, in particular in combination with 2'-methoxyethyl modifications of the sugars.

Preferentially, these oligonucleotides are in the single-stranded form.

According to a particularly advantageous embodiment, these oligonucleotides comprise a sequence exhibiting at least 60%, preferably 70%, 80% or 90%, identity with the sequence SEQ ID No. 2, in which the nucleotides at positions 2, 4, 6, 7, 9, 11, 13, 15, 17, 19 and 20, in the 5' to 3' direction, are thioesterified.

According to a particularly advantageous embodiment, these oligonucleotides comprise a sequence exhibiting at least 60% identity with the sequence SEQ ID No. 2, in which the nucleotides at positions 1, 2, 3, 4, 5, 16, 17, 18, 19 and/or 20, in the 5' to 3' direction, are 2'-O-methylated.

Preferentially, the oligonucleotides according to the present invention are DNAs.

A subject of the present invention is also oligonucleotides of the iRNA (Interfering Ribonucleic Acid) type comprising from 10 to 60 nucleotides, and preferably from 15 to 25 nucleotides, which hybridize specifically to the sequence SEQ ID No. 21 and which inhibit the expression of OB-RGRP.

Preferentially, such iRNAs comprise 17 or 19 nucleotides taken continuously from the sequence SEQ ID No. 21, or from the sequence complementary thereto.

These iRNAs may be double-stranded, in which case they advantageously consist of two strands comprising from 15 to 60 nucleotides. According to a preferred embodiment, such an iRNA is one in which at least one of the two strands comprises a sequence exhibiting at least 60%, preferably 70%, 80% or 90%, identity with one of the sequences SEQ ID No. 37 or SEQ ID No. 38.

The iRNAs may also be expressed in single-stranded form. Such iRNAs may then comprise a loop. They advantageously comprise from 15 to 60 nucleotides. According to a preferred embodiment, such an iRNA comprises a sequence exhibiting at least 60%, preferably 70%, 80% or 90%, identity with the sequence SEQ ID No. 42.

Nucleotides A(A/G) and (C/T)T can be added respectively in 5' and in 3' of this sequence of 17 or 19 nucleotides. Other types of residues or chemical groups can, however, be added to these two ends, provided that they do not decrease the activity of the antisenses.

The nucleotide modifications described for the antisenses are also possible for those making up the composition of the siRNAs.

The present invention also includes any modifications of the antisenses or of the iRNAs which are directed toward increasing the resistance of these compounds to cellular nucleases, or their penetration into cells and/or their effectiveness in targeting the OB-RGRP sequence.

When they are DNAs, the oligonucleotides according to the present invention can be produced conveniently and routinely by the well-known technique of solid-phase synthesis. The equipment for such synthesis is sold by various specialized companies, such as Applied Biosystems (Foster City, Calif.). The synthesis of the antisenses in the present invention makes use of chemical synthesis on a suitable support according to methods known to those skilled in the art, in particular described by E. Uhlmann, A. Peyman, A. Ryte, A. Schmidt and E. Buddecke (1999, Methods in Enzymology 313: 268-284) and by E. Uhlmann (Recent advances in the medicinal chemistry of antisense oligonucleotides, Current Opinion of Drug Discovery and Development 3: 203-213, 2000). Any other method of synthesis known to those skilled in the art may also be used.

When they are iRNAs, the oligonucleotides according to the present invention can be synthesized by chemical synthesis, when they are synthetic iRNAs, or expressed in situ using vectors for synthesizing such oligonucleotides, or obtained by in vitro cleavage of a double-stranded RNA with RNAse III or the DICER enzyme.

siRNAs (small iRNAs) can be obtained from various suppliers, such as Proligo (Proligo France SAS 1 rue Robert et Sonia Delaunay 75011 Paris) Dharmacon (Dharmacon, Inc. 1376 Miners Drive #101 Lafayette, Colo. 80026) and Ambion (Ambion (Europe) Ltd. Ermine Business Park Spitfire Close Huntingdon, Cambridgeshire PE29 6XY United Kingdom), or can be synthesized using kits marketed by various companies, such as Dharmacon and Ambion.

Preferentially, the iRNAs according to the present invention are in double-stranded form.

After synthesis, the iRNAs are first of all taken up in RNAse-free water. The pairing of the two single-stranded molecules can be carried out as follows: 20 $\mu$mol.$L^{-1}$ of each strand are mixed in the pairing buffer (100 mmol.$L^{-1}$ of potassium acetate, 30 mmol. $L^{-1}$ of HEPES-KOH, pH 7.4, 2 mmol.$L^{-1}$ of magnesium acetate) and then heated at 90° C. for 1 min, followed by incubation for 1 h at 37° C.

Transfection of the siRNAs can be carried out using the same protocol as for transfection of the antisenses.

An alternative for the iRNA is the use of vectors which allow synthesis of antisense RNAs specific for the gene to be silenced and which will pair in the transfected cells to give an siRNA. A first vector system allows expression of an antisense sequence by two promoters in opposite direction, on each side of this sequence, producing two complementary RNAs which will pair in the transfected cells and give an siRNA. Another vector system uses the synthesis of an RNA having the sequence of the antisense followed by the sense sequence, a few nucleotides apart, which will create a stem-loop RNA structure which will be cleaved in the transfected cells to give an siRNA. Yet another vector system involves the expression of a double-stranded RNA, up to 600 base pairs long, which cannot leave the nucleus since it does not have the necessary sequences: no 3'-cap (ribozyme site) nor a 5'-poly-A tail (MAZ zinc finger protein binding site). This long RNA is cleaved in the nucleus to give functional siRNAs which will pass into the cytoplasm and cause degradation of the target RNA.

These vectors are transfected conventionally as described above for the various DNAs. Stable lines which exhibit a knockout of the target gene can be obtained by antibiotic selection conventionally used to obtain lines.

In general, those skilled in the art may refer, for the iRNAs to the following publications: Elbashir S. M. et al. (2001, *Nature* 411: 494-498), Elbashir S. M. Lendeckel W. and Tuschl T. (2001, *Genes & Dev.* 15: 188-200) and Masters J. R., et al. (2001. *Proc. Natl. Acad. Sci. USA* 98: 8012-8017).

Vectors which allow the expression of iRNAs can be obtained as described by Brummelkamp T. R., Bernards R., Agami R. (2002. *Science* 296: 550-553) and Yu J. Y., DeRuiter S. L., and Turner D. (2002., *Proc. Natl. Acad. Sci. USA* 99: 6047-6052) and Shinagawa T. and Ishii S. (2003, *Genes & Dev.* 17: 1340-1345).

Such vectors, and also cells containing such vectors, are subjects of the present application.

A subject of the present invention is also medicinal products containing such oligonucleotides, vectors and cells, and pharmaceutical compositions containing a pharmacologically active amount of such oligonucleotides, vectors and cells and pharmaceutically acceptable excipients.

Another subject of the present invention is the use of such oligonucleotides, vectors and cells, for producing a medicinal product for preventing and/or treating leptin-related pathological conditions.

A subject of the invention is also a method of curative or preventive treatment of leptin-related diseases, consisting in administering such oligonucleotides, vectors and cells to a patient suffering from said disease.

Another subject of the invention is a method for determining the modification, by a compound, of the interaction between the OB-RGRP or the MYO47 protein, or a protein exhibiting at least 65% identity with this protein or with the MYO47 protein, and the leptin receptor.

It also relates to fusion proteins for implementing this method, and also to nucleic acids encoding these proteins.

A subject of the invention is also a method of curative or preventive treatment of leptin-related diseases, consisting in administering a ligand selected using the method defined above to a patient suffering from said disease.

A first subject of the present invention is therefore a fusion protein which is composed of a sequence exhibiting at least 65% identity with the sequence SEQ ID No. 4, or the sequence SEQ ID No. 16, or of a substantial part of the sequence SEQ ID No. 4 or of the sequence SEQ ID No. 16, and of an energy-donor or energy-acceptor protein, or of a substantial and active part of an energy-donor or energy-acceptor protein.

The fusion proteins according to the present invention are composed in substance of a component corresponding to part or all of a sequence exhibiting at least 65%, preferentially at least 75%, and even more preferentially at least 85% or 95%, identity with the sequence SEQ ID No. 4 or the sequence SEQ ID No. 16, or of a substantial part of the sequence SEQ ID No. 4 or of the sequence SEQ ID No. 16, and of a component corresponding to an energy-donor or -acceptor protein. They may, however, comprise other amino acid sequences, derived from other proteins, such as signal sequences.

Advantageously, the energy-donor protein is Renilla luciferase (Rluc). It may, however, be any other energy-donor protein such that the emission spectrum of the donor overlaps the excitation spectrum of the acceptor sufficiently to allow efficient energy transfer between the two partners. It may thus be GFP, if the energy transfer is FRET, or else aequorin if the energy transfer is CRET. Aequorin can be obtained and used as described in patent application EP 0 187 519, or in the article by Inouye et al. (PNAS USA 82: 3154-3158 (1985)).

As regards the energy-acceptor fluorescent protein, it is preferentially DsRed, GFP or a mutant of this protein, such as YFP, EYFP, wild-type GFP, GFPS65T, Topaz or $GFP_{10}$.

It may however be any other energy-acceptor fluorescent protein such that the excitation spectrum of the acceptor and the emission spectrum of the donor overlap sufficiently to allow efficient energy transfer between the two partners.

These proteins are known to those skilled in the art, who can find their sequences in the literature, in particular in the review by Blinks et al. (Pharmacol. Rev. 28: 1-93 (1976)). In particular, GFP is described by Tsien (Annu. Rev. Biochem. 67: 509-544 (1998)) and the cloning thereof is described by Prasher et al. (Gene 111: 229-233 (1992)). As regards the cloning of DsRed, it is described by Matz et al. (Nat. Biotechnol. 17: 969-973 (1999)). For Rluc, those skilled in the art can refer to Blinks et al. (Pharmacol. Rev. 28: 1-93 (1976)) or else to Lorenz et al. (PNAS 88: 4438-4442 (1991)).

Particularly advantageously, the donor and acceptor fusion proteins have one of the sequences SEQ ID No. 6, SEQ ID No. 8, SEQ ID No. 12, SEQ ID No. 14, SEQ ID No. 18 or SEQ ID No. 20, or a variant of this sequence exhibiting at least 65% identity.

Other subjects of the present invention are nucleic acids encoding these proteins. Such nucleic acids may be complementary or genomic DNAs, or RNAs. These nucleic acids or polynucleotides can be in single-chain form or in the form of duplex.

They are particularly advantageously complementary DNAs.

Preferentially, a subject of the invention is a nucleic acid having at least 65%, preferentially at least 75%, and even more preferentially at least 85% or 95%, nucleotide identity with a nucleic acid of sequence SEQ ID No. 5, SEQ ID No. 7, SEQ ID No. 11, SEQ ID No. 13, SEQ ID No. 17 or SEQ ID No. 19.

According to yet another aspect, the invention relates to a nucleic acid which hybridizes, under high stringency hybridization conditions, with a nucleic acid as defined above, and more particularly a nucleic acid of nucleotide sequence SEQ ID No. 5, SEQ ID No. 7, SEQ ID No. 11, SEQ ID No. 13, SEQ ID No. 17 or SEQ ID No. 19, or a nucleic acid of complementary sequence.

For the purpose of the present invention, the "percentage identity" between two nucleotide or amino acid sequences can be determined by comparing two optimally aligned sequences through a window of comparison.

The part of the nucleotide sequence or polypeptide in the window of comparison, may thus comprise additions or deletions (for example gaps) compared to the reference sequence (which does not comprise these additions or these deletions) so as to obtain optimal alignment of the two sequences.

The percentage is calculated by determining the number of positions at which an identical nucleic acid base or amino acid residue is observed for the two (nucleic acid or peptide) sequences compared, in dividing the number of positions at which there is identity between the two bases or amino acid residues by the total number of positions in the window of comparison, and then multiplying the result by 100 in order to obtain the percentage sequence identity.

The optimal alignment of the sequences for comparison can be produced on a computer using known algorithms contained in the WISCONSIN GENETICS SOFTWARE PACKAGE, GENETICS COMPUTER GROUP (GCG), 575 Science Doctor, Madison, Wis.

By way of illustration, the percentage sequence identity may be produced using the BLAST software (versions BLAST 1.4.9 of March 1996, BLAST 2.0.4 of February 1998 and BLAST 2.0.6 of September 1998), using exclusively the default parameters (S. F. Altschul et al, J. Mol. Biol. 1990 215: 403-410, S. F Altschul et al, Nucleic Acids Res. 1997 25: 3389-3402). Blast searches for sequences similar/homologous to a reference "request" sequence using the algorithm of Altschul et al. The request sequence and the databases used may be peptide-based or nucleic acid-based, any combination being possible.

For the purpose of the present invention, the expression "high stringency hybridization conditions" will be intended to mean the following conditions:

1—Membrane Competition and PRE HYBRIDIZATION:

Mix: 40 μl of salmon sperm DNA (10 mg/ml)+40 μl of human placenta DNA (10 mg/ml)

Denature for 5 min at 96° C., then immerse the mixture in ice.

Remove the 2×SSC and pour 4 ml of formamide mix into the hybridization tube containing the membranes.

Add the mixture of the two denatured DNAs.

Incubate at 42° C. for 5 to 6 hours, with rotation.

2—Labeled Probe Competition:

Add 10 to 50 μl of Cot I DNA to the labeled and purified probe, depending on the amount of repetition.

Denature for 7 to 10 mn at 95° C.

Incubate at 65° C. for 2 to 5 hours.

3—Hybridization:

Remove the prehydribidization mix.

Mix 40 μl of salmon sperm DNA+40 μl of human placental DNA; denature for 5 min at 96° C., then immerse in ice.

Add 4 ml of formamide mix, the mixture of the two DNAs and the denatured Cot I DNA/labeled probe to the hybridization tube.

Incubate for 15 to 20 hours at 42° C., with rotation.

4—Washes:

One wash at ambient temperature in 2×SSC, to rinse.

2 times 5 minutes at ambient temperature in 2×SSC and 0.1% SDS at 65° C.

2 times 15 minutes at 65° C. in 1×SSC and 0.1% SDS at 65° C. Wrap the membranes in Saran wrap and expose.

The hybridization conditions described above are suitable for hybridization, under high stringency conditions, of a nucleic acid molecule of varying length of 20 nucleotides to several hundred nucleotides.

It goes without saying that the hybridization conditions described above can be adjusted as a function of the length of the nucleic acid the hybridization of which is desired, or of the type of labeling chosen, according to the techniques well known to those skilled in the art.

The suitable hybridization conditions may, for example, be adjusted according to the teaching contained in the work by HAMES and HIGGINS (1985, "Nucleic acid hybridization: a practical approach", Hames and Higgins Ed., IRL Press, Oxford) or else in the work by F. AUSUBEL et al. (1989, Current Protocols in Molecular Biology, Green Publishing Associates and Wiley Interscience, N.Y.).

The proteins which are the subjects of the present invention can be obtained by any means known to those skilled in the art. They are, however, advantageously obtained by expression of the nucleic acids as described above, encoding these proteins, optionally inserted into expression vectors, into cells advantageously chosen, optionally followed by an extraction and a purification which may be total or partial.

The invention also relates to a recombinant vector comprising a nucleic acid according to the invention.

Advantageously, such a recombinant vector will comprise a nucleic acid chosen from the following nucleic acids:

a) a nucleic acid encoding a protein having at least 65% amino acid identity with a sequence SEQ ID No. 6, SEQ ID No. 8, SEQ ID No. 18 or SEQ ID No. 20, or a peptide fragment or a variant thereof;

b) a nucleic acid comprising a polynucleotide having a sequence SEQ ID No. 5, SEQ ID No. 7, SEQ ID NO. 17 or SEQ ID No. 19, or a fragment or a variant thereof;

c) a nucleic acid having at least 65% nucleotide identity with a nucleic acid having a sequence SEQ ID No. 5, SEQ ID No. 7, SEQ ID No. 17 or SEQ ID No. 19, or a fragment or a variant thereof;

d) a nucleic acid which hybridizes, under high stringency hybridization conditions, with a nucleic acid of sequence SEQ ID No. 5, SEQ ID No. 7, SEQ ID No. 17 or SEQ ID No. 19, or a fragment or a variant thereof.

For the purposes of the present invention, the term "vector" will be intended to mean a circular or linear DNA or RNA molecule which is indifferently in single-stranded or double-stranded form.

According to one embodiment, the expression vector comprises, besides a nucleic acid in accordance with the invention, regulatory sequences which make it possible to direct the transcription and/the translation thereof.

According to an advantageous embodiment, a recombinant vector according to the invention will in particular comprise the following elements:

(1) elements for regulating the expression of the nucleic acid to be inserted, such as promoters and enhancers;

(2) the coding sequence included in the nucleic acid in accordance with the invention to be inserted into such a vector, said coding sequence being placed in phase with the regulatory signals described in (1); and (3) suitable transcription initiation and stop sequences.

In addition, the recombinant vectors according to the invention may include one or more origins of replication in the cellular hosts in which their amplification or their expression is desired, markers or selection markers. By way of examples, the promoters for eukaryotic cells will comprise the thymidine kinase promoter of the HSV virus or else the mouse metallothionein-L promoter.

In general, in choosing a suitable promoter, those skilled in the art may advantageously refer to the work by SAMBROOK et al. (1989, "Molecular Cloning: A Laboratory Manual," $2^{nd}$ ed., Cold Spring Harbor Laboratory Press, Cold Spring Harbor, N.Y.) or else to the techniques described by FULLER et al. (1996*, Immunology in Current Protocols in Molecular Biology*, Ausubel et al).

The preferred vectors according to the invention are plasmids, such as, for example, the vectors pCDNA3 (Invitrogen), pQE70, pQE60, pQE9 (Qiagen), psiX174, pBluescript SA, pNH8A, pNH16A, pNH18A, pNH46A, pWLNEO, pSV2CAT, pOG44, pXTI and pSG(Stratagene).

They may also be vectors of the baculovirus type, such as the vector pVL1392/1393 (Pharmingen) used to transfect cells of the Sf9 line (ATCC No. CRL 1711) derived from *Spodoptera frugiperda.*

They may also be adenoviral vectors, such as human adenovirus type 2 or 5.

A recombinant vector according to the invention may also be a retroviral vector or else an adeno-associated vector (MV). Such adeno-associated vectors are, for example, described by FLOTTE et al. (1992*, Am. J. Respir. Cell Mol. Biol.*, 7: 349-356).

Objects of the present invention are also cells comprising a protein, a nucleic acid or a vector as described above, or fragments of these cells, lysates of these cells or else membranes of these cells.

Such cells may be cells isolated from an organism and cultured in a suitable growth medium. They are, however, preferentially cell lines. Thus, such lines are particularly advantageously the cells lines HEK 293, COS (ATCC No. CRL 1650), COS-M6 and HeLa (ATCC No. CCL2), or else Cv 1 (ATCC No. CCL70), Sf-9 (ATCC No. CRL 1711), CHO (ATCC No. CCL-61) or 3T3 (ATCC No. CRL-6361).

The membranes of these cells can be prepared by any method known to those skilled in the art.

Preferentially, they will be prepared by mechanical grinding of the cells and then centrifugation of the suspensions obtained, as illustrated in the examples which follow.

The present invention also relates to compositions comprising cells as described above and saponin.

The present invention also relates to a method for determining the modification, by a compound, of the interaction between the OB-RGRP, the MY047 protein or a protein exhibiting at least 65% identity with the sequence SEQ ID No. 4 or the sequence SEQ ID No. 16, and the leptin receptor, comprising the steps consisting in:

bringing said compound into contact with a protein exhibiting at least 65% identity with the sequence SEQ ID No. 4 or the sequence SEQ ID No. 16, and the leptin receptor, or cells, or fragments or lysates or membranes of cells, comprising such proteins, and optionally a suitable enzyme substrate, and measuring the interaction between a protein exhibiting at least 65% identity with the sequence SEQ ID No. 4 or the sequence SEQ ID No. 16, and the leptin receptor.

Preferentially, said compound is brought into contact with an energy-donor fusion protein and an energy-acceptor fusion protein, or cells, or fragments or lysates or membranes of cells, comprising such a protein, and optionally a suitable enzyme substrate.

Preferentially, said method is brought into contact with cells treated with an agent which permeabilizes these cells, such as saponin.

The energy-donor fusion proteins and the energy-acceptor fusion proteins are chosen such that the energy resulting from the activation of the donor may be transferred efficiently to the acceptor.

In an advantageous embodiment of said method, the energy-donor fusion protein is a protein from fusion with luciferase or a substantial part of luciferase, in which case the substrate is advantageously coelenterazine.

In a preferential embodiment of said method, the energy-acceptor fusion protein is a protein from fusion with YFP or a substantial part of YFP.

In an advantageous embodiment of said method, the energy transfer measured in the presence of the test compound is compared to that measured in the absence of the test compound.

In another advantageous embodiment of said method, the energy transfer measured in the presence of the test compound and of leptin (or a ligand of the receptor) is compared to that measured in the presence of the compound in the absence of leptin (or a ligand of the receptor).

Preferentially, the method is carried out on cell membranes, as described above.

Preferentially, the donor and acceptor proteins according to the present invention are chosen such that the energy transfer takes place by first or second generation BRET (for Bioluminescence Resonance Energy Transfer) or LRET (for Luminescence Resonance Energy Transfer). However, such an energy transfer may be effected by FRET (for Fluorescence Resonance Energy Transfer) or else by CRET (for Chemioluminescence Resonance Energy Transfer).

Whatever the type of energy transfer, the energy-donor fusion protein/energy-acceptor fusion protein pairs are chosen so as to allow such transfer.

BRET2 ($2^{nd}$ generation) consists of energy transfer between Renilla luciferase and a mutant GFP, $GFP_{10}$, using a suitable substrate, DeepblueC™ coelanterazine (Biosignal Packard).

CRET consists of energy transfer between aequorin, which is a luciferase, and GFP.

FRET consists of energy transfer between two proteins of the GFP family having different spectra.

To implement these transfers, those skilled in the art may refer to D. Ramsay et al. (Biochem J 365: 429-40 (2002)) and to K. Yoshioka et al. (FEBS Lett 523: 147-151 (2002)) for BRET2, to Baubet et al. (PNAS USA 97: 7260-7265 (2000)) for CRET, and to Matyus (J Photochem Photobiol B 12: 323-337 (1992)) and Pollok and Heim (Trends Cell Biol 9:57-60 (1999)) for FRET.

Another subject of the present invention is a method for screening or detecting compounds intended for the prevention and/or treatment of leptin-related pathological conditions, comprising the steps consisting in:

- bringing said compound into contact with a protein exhibiting at least 65% identity with the sequence SEQ ID No. 4 or the sequence SEQ ID No. 16, and the leptin receptor, or cells, or fragments or lysates or membranes of cells, comprising such proteins, and optionally a suitable enzyme substrate, and
- measuring the interaction between a protein exhibiting at least 65% identity with the sequence SEQ ID No. 4 or the sequence SEQ ID No. 16, and the leptin receptor.

Preferentially, the protein exhibiting at least 65% identity with the sequence SEQ ID No. 4 or the sequence SEQ ID No.16 is the OB-RGRP or MY047.

The method according to the present invention is compatible with the 96-well or 384-well plates generally used. It does not require the use of radioactive molecules, but is sensitive, reproducible and rapid, and the result is easy to read. This characteristic is particularly advantageous for carrying out large scale screening.

The present invention also relates to the use of compounds selected using a method consisting in:

- bringing said compound into contact with a protein exhibiting at least 65% identity with the sequence SEQ ID No. 4 or the sequence SEQ ID No. 16, and the leptin receptor, or cells, or fragments or lysates or membranes of cells, comprising such proteins, and optionally a suitable enzyme substrate, and
- measuring the interaction between a protein exhibiting at least 65% identity with the sequence SEQ ID No. 4 or the sequence SEQ ID No. 16, and the leptin receptor.

A subject of the present invention is, finally, a method of curative or preventive treatment of leptin-related diseases or diseases related to its receptor, comprising the steps of:

- selecting said compound using a method consisting in:
  - bringing said compound into contact with a protein exhibiting at least 65% identity with the sequence SEQ ID No. 4 or the sequence SEQ ID No. 16, and the leptin receptor, or cells, or fragments, or lysates or membranes of cells, comprising such proteins, and optionally a suitable enzyme substrate, and
  - measuring the interaction between a protein exhibiting at least 65% identity with the sequence SEQ ID No. 4 or the sequence SEQ ID No. 16, and the leptin receptor
- administering said compound to a patient suffering from said disease.

Leptin-related pathological conditions may be diseases related to a decrease in bone density, such as, for example, osteoporosis, or, conversely, those related to considerable calcification.

They may also be diseases which have an effect on weight, such as obesity, diabetes or anorexia.

They may also be diseases which have an effect on sexual maturation, hematopoiesis, angiogenesis, thrombus formation, the regulation of immunity and inflammation, fetal development, cicatrization and cancer.

The compounds of the invention, oligonucleotides, iRNAs, or other compounds, may be formulated in pharmaceutical compositions for the purpose of topical, oral, parenteral, intranasal, intravenous, intramuscular, subcutaneous, intraocular administration, etc. Preferentially, the pharmaceutical compositions contain pharmaceutically acceptable vehicles for an injectable formulation. They may in particular be isotonic, sterile, saline (monosodium or disodium phosphate, sodium, potassium, calcium or magnesium chloride, etc., or mixtures of such salts) solutions, or dry, in particular lyophilized, compositions which, by addition, as appropriate, of sterilized water or of physiological saline, make it possible to constitute injectable solutes.

The formulation of therapeutic compositions and their administration fall within the competence of those skilled in the art.

The formulation of the compounds may include various products known to those skilled in the art. Preferentially, the compounds may, for example, have salts, such as sodium, potassium, ammonium, magnesium, calcium, polyamines, or hydrochloric, hydrobromic, sulfuric, phosphoric or nitric acid, added to them. Other salts can also be used, such as those originating from acetic, oxalic, tartaric, succinic, maleic, fumaric, gluconic, citric, malic, ascorbic, benzoic, tannic, palmitic, alginic, polyglutamic, naphthalene-sulfonic, methanesulfonic, p-toluenesulfonic, naphthalenedisulfonic or polygalacturonic acid. Finally, chlorine, bromine and iodine salts can also preferentially be used.

The composition and the formulation for topical administration can include transdermal patches, ointments, lotions, creams, gels, drops, suppositories, sprays, liquids and powders.

The composition and the formulation for oral administration can include powders, granules, microparticles, nanoparticles, suspensions, solutions, which may or may not be aqueous, capsules, gelatin capsules, sachets, tablets or mini tablets. Thickeners, flavors, diluents, emulsifiers, dispersing agents or binders may be added.

The composition and the formulation for parenteral, intrathecal or intravententricular administration can include sterile aqueous solutions which can also contain buffers, diluents and other additives, such as, but not limited to, penetration-increasing agents, transporting products and excipients.

The composition can be formulated and used as a foam, an emulsion, a microemulsion, cationic, pH-sensitive or negatively charged liposomes, and transferomes.

In general, the various formulations can contain a mixture of one or more agents, such as, but not limited to, agents which increase the penetration of the compound (surfactants, bile salts, chelating agents, non-chelating surfactants), excipients (binders, fillers, lubricants, disintegrating agents, wetting agents), or transporters (water, saline solutions, alcohols, polyethylene glycol, gelatin, lactose, amylose, magnesium stearate, talc, silicic acid, viscous paraffin, hydroxymethylcellulose, polyvinylpyrrolidone). Other components can be added, such as dyes, flavors, preserving agents, antioxidants, opacifiers, thickeners and stabilizers.

The dosage depends on the severity and on the sensitivity of the state of the disease to be treated, with a treatment period possibly ranging from a few days to a few months, or until the treatment is effective or a reduction in the disease is observed. The optimum dosage can be calculated from measurements of accumulation of the therapeutic agent in the patient's body. Those skilled in the art can easily determine the optimum dosages, the methods of dosage and the rates of repetition of these dosages. The optimum dosages can vary as a function of the relative effectiveness of each oligonucleotide or iRNA, and can, in general, be estimated by measuring the EC50s of the doses used in vitro and in vivo in animal models. In general, the dosage is between 0.01 μg and 100 g per kilo of bodyweight and can be administered one or more times, daily, weekly, monthly or annually, or even once every 2 to 20 years.

Competent individuals can easily determine the rate of repetition of the dosages based on the amount of time the compound is present in the body fluids or the tissues. Subsequent to a successful treatment, it may be desirable for the patient to continue a maintenance therapy in order to prevent reappearance of the disease; to do this, the oligonucleotide or the iRNA is administered at maintenance doses ranging from 0.01 μg to 100 g per kilo of bodyweight, one or more times a day, up to once every 20 years.

The administration of antisense in vivo has been carried out successfully by various authors, using protocols of simple injection of antisense intravenously (He et al. (1998) Zhonghua Shi Yan He Lin Chuang Bing Du Xue Za Zhi 12:1-4) or intracerebrally (Yoburn et al. (2003) Synapse 47: 109-116, Tischkau et al. (2003) J. Biol. Chem. 278: 718-723). In the last two years, more complex systems for targeting antisense in the organism have been developed and used successfully (Morishita et al. (2002) J. Endocrinol. 175: 475-485, Bartsch et al. (2002) Pharm. Res. 19: 676-680), making it possible, in mice and rats, to treat various cancers (Rait et al. (2002) Mol. Med. 8: 475-486, Ochietti et al. (2002) J. Drug. Target 10: 113-121, Eder et al. (2002) Cancer Gene Ther. 9:117-125). The transfection of antisenses involves the same methods as for the transfection of iRNAs, making it possible to envision the same applications in vivo for the iRNAs. With this in mind, it is possible to imagine targeting the antisense or the iRNAs to the central nervous system, in order to treat disorders of central origin (obesity), but also those produced by a peripheral action of leptin receptors. More particularly, it is possible to envision there being an action of the antisenses or of the iRNAs on the transport of leptin across the blood-brain barrier, involving OB-R. Moreover, endothelial cells have already been successfully targeted using an in vivo antisense strategy (Bartsch et al. (2002) Pharm. Res. 19: 676-680).

FIGURES

FIG. 1

Sequences of the various antisense ODNs are used, AS 01 to AS 16. The SEQ ID Nos. correspond to these AS sequences as follows: AS 01 through AS 13 correspond to SEQ ID Nos. 22 through 34, respectively. AS 14 corresponds with SEQ ID No. 2. AS 15 and AS 16 correspond with SEQ ID Nos. 35 and 36, respectively.

FIG. 2

Alignment of the OB-RGRP protein sequences of various species and of the human MY047 protein sequence. The potential transmembrane domains were determined by various methods (HMMTOP, TMHMM, TopPred2, TMpred) and are written in bold. OB-RBRP_human is found in the sequence listing as SEQ ID No. 3; My47_human is found in the sequence listing as SEQ ID No. 48; yt02_C.elegans is found in the sequence listing as SEQ ID No. 49; YJ14_Levure is found in the sequence listing as SEQ ID No. 50; the Consensus sequence is found in the sequence listing as SEQ ID No. 51.

FIG. 3

Figure 3B:
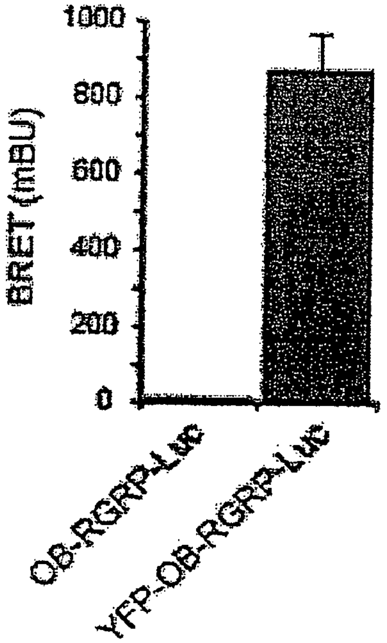

Topology of OB-RGRP studied by BRET, using the double fusion protein YFP-OB-RGRP-Luc. FIG. 3*a*: diagrammatic representation of the topology of OB-RGRP for the models 3 and 4TM. FIG. 3*b*: results of the BRET experiments using the proteins indicated. The data are expressed in mBU.

FIG. 4

Study of the oligomerization of OB-RGRP with SDS-PAGE experiments and immunoprecipitations. FIG. 4*a*: the cells expressing the fusion proteins indicated were treated or not treated with 2 mmol.$L^{-1}$ dithiobis(succinimidyl propionate) (DSP) in PBS (1×, pH7.4) in order to crosslink the protein complexes. The proteins were separated by SDS-PAGE and the proteins from fusions with YFP were detected using a specific anti-YFP antibody. FIG. 4*b*: the cells expressing the construct 6Myc-OB-RGRP were solubilized with 1% of digitonin or 5% of SDS and the solubilized material was immunoprecipitated with an anti-myc antibody. The precipitates were subjected to separation by SDS-PAGE and the proteins tagged with myc were detected with an anti-myc antibody.

FIG. 5

Identification of the molecular determinants involved in the oligomerization of OB-RGRP. The proteins from fusions with the OB-RGRP truncations were treated as described in FIG. 4*b*. TM, transmembrane domain.

FIG. 6

Figure 6:
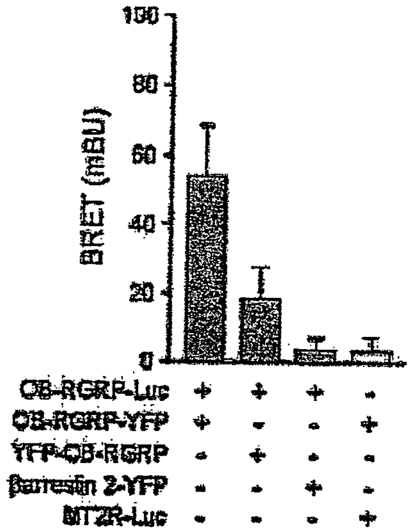
Figure 6B:
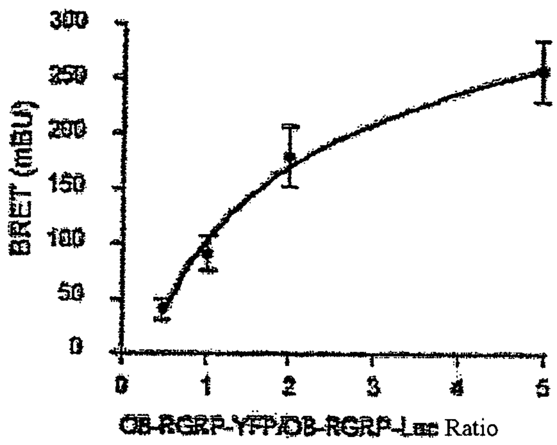

Study of the oligomerization of OB-RGRP in live HEK cells, by BRET technology. FIG. 6*a*: the fusion proteins indicated were coexpressed at an equimolar ratio, and BRET measurement experiments were carried out. FIG. 6*b*: constant amounts of the plasmid OB-RGRP-Luc were coexpressed with increasing amounts of the plasmid OB-RGRP-YFP and BRET measurements were carried out. MT2R-Luc, protein from fusion of the melatonin receptor MT2 with luciferase.

FIG. 7

Interaction of OB-$R_s$ and of OB-RGRP studied by BRET. The fusion proteins indicated were coexpressed at an equimolar ratio and BRET measurements were carried out. IR-YFP, protein from fusion of the insulin receptor with YFP.

FIG. 8

Figure 8A:
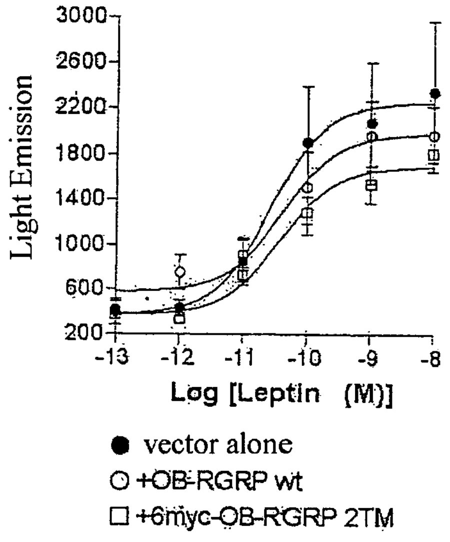
Figure 8B:
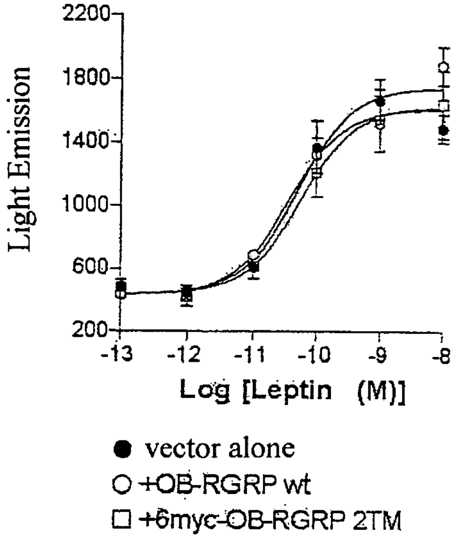

Dose-dependent activation of the reporter genes for STAT3 (FIG. 8*a*) and STAT5 (FIG. 8*b*) in HeLa cells, by OB-Ri in the presence of overexpression of the OB-RGRP protein constructs as indicated.

FIG. 9

Effect of the overexpression of OB-RGRP on the expression of OB-R at the surface of the cells. HEK 293 cells transfected or not transfected with the OB-RGRP expression vector, and COS cells transfected with the OB-R, or OB-$R_s$ expression vectors and +/− the OB-RGRP vectors, were used to determine the amount of receptors expressed at the surface and the total expressed in the cells, by $^{125}$I-leptin-binding experiments.

FIG. 10

Effect of the various antisense oligodeoxynucleotides (ODNS) on the level of OB-RGRP messengers observed by semiquantitative RT-PCR. FIG. 10*a*: determination of the linear zone of amplification of the OB-RGRP and GAPDH transcripts, as a function of the number of PCR cycles. FIG. 10*b*: quantification of the results shown in panel a. FIG. 10*c*: determination of the relative levels of expression of the OB-RGRP mRNAs at 26 PCR cycles, in the cells incubated with the various antisense ODNs.

FIG. 11

Effect of the various interfering RNAs on the level of OB-RGRP messengers observed by semi-quantitative RT-PCR. FIG. 1*la*: sequence SEQ ID No. 37 (5'-3') and SEQ ID No. 38 (3'-5') of the synthetic iRNA used (homolog for humans and mice). FIG. 11*b*: determination of the relative expression levels of the OB-RGRP mRNAs at 26 PCR cycles, in untransfected HELA cells or HELA cells transfected with the synthetic iRNA. FIG. 11*c*: sequence SEQ ID No.42 of the hairpin iRNA synthesized from the vector PCR3.1-RNAi 14. FIG. 11*d*: determination of the relative expression levels of the OB-RGRP mRNAs at 26 PCR cycles, in untransfected Ltk cells or Ltk cells transfected with the vector PCR3.1-RNAi 14.

FIG. 12

Effect of the OB-RGRP-specific antisense ODNs on the activation of a STAT3 reporter gene. The HeLa cells were cotransfected firstly with the OB-Rl expression vector and the constructs of the reporter genes for STAT3 or 5, and then with the antisense ODNs indicated. After 48 hours of stimulation or no stimulation with 10 $nmol.L^{-1}$ of leptin.

FIG. 13

Effect of the OB-RGRP-specific antisense ODNs on the surface expression of OB-R. The HeLa cells were transfected or not transfected with the $OB\text{-}R_l$ or $OB\text{-}R_s$ expression plasmids, before a second transfection with the antisense ODNs indicated, or no second transfection. 48 h post-transfection, the total amount of OB-R and the fraction exposed at the surface were determined in binding experiments with $^{125}I$-leptin.

The present invention is illustrated, without, however, being limited, by the following examples.

Materials and Methods used in the Examples

Plasmid Construction

The proteins from fusion of OB-R with YFP and luciferase were constructed by ligation of YFP and of luciferase to the C-terminal portion of the OB-R receptors, by standard molecular biology techniques. The coding region of YFP was obtained from the vector Cytogem®-Topaze (pGFPtpz-N1) (Packard, Meriden, Conn.) and was inserted into the EcoRV site of the vector pcDNA3/CMV (Invitrogen, Groningen, The Netherlands) containing a modified polylinker. The coding region of Renilla luciferase was obtained from the vector pRL-CMV (Promega, Madison, Wis.) and inserted into the EcoRV site of the modified vector pcDNA3. The coding regions of OB-R, and of OB-R, (a gift from Dr. Gainsford, Royal Melbourne Hospital, Victoria, Australia) were inserted into the two vectors described above, respectively into the EcoR1/BamH1 and Nhe1 sites. The stop codons were deleted by site-directed mutagenesis and the frame of the fusion proteins was adjusted at the same time.

The vector pcDNA3-OB-RGRP was obtained by insertion of the coding region of OB-RGRP, obtained from the vector pCDNA3-Di1, into the EcoR1 and Xba1 sites of the vector pcDNA3/CMV (Invitrogen, Groningen, The Netherlands). The stop codon of OB-RGRP was deleted by site-directed mutagenesis. The vector pcDNA3-OB-RGRP-Luc was obtained by digestion of the vector pRL-CMV N3 (Promega, Madison, Wis.) with Sma1 and Hpa1 and by insertion of the fragment corresponding to the coding region of Renilla luciferase, after the coding region of OB-RGRP, into the filled-in BspE1 site of the vector pcDNA3-OB-RGRP.

The vector pcDNA3-YFP was obtained by subcloning the coding region of YFP from the vector pGFPtpz-N1 (Packard, Meriden, Conn.) inserted into the EcoRV site of the vector pcDNA3/CMV. The vector pcDNA3-OB-RGRP-YFP was obtained by insertion of the BamH1/BspE1 fragment of the vector pCDNA3-OB-RGRP non-stop into the vector pcDNA3-YFP digested with the BamH1 and Age1 enzymes.

The construct pcDNA3-GFP-OB-RGRP-Luc was obtained by insertion of the OB-RGRP-Luc fragment of the vector pcDNA3-OB-RGRP-Rluc, cleaved with EcoR1, into the EcoR1 site of the vector pcDNA3-YFP. The stop codon of the YFP was removed by site-directed mutagenesis.

The vector 6Myc-OBR-GRP (4TM) was obtained by insertion of the 6myc fragment of the vector pCDNA3-RSV-6Myc into the BamH1 and EcoR1 sites of the vector pCDNA3-OBRGRP. The various OB-RGRP deletions (2 and 3 TM) were obtained by PCR and the insertion into the vector pcDNA3, into the EcoR1 and Xba1 sites. The coding sequence of MY047 was obtained by RT-PCR on mRNAs of human origin. The PCR fragment was digested with the EcoR1/Xba1 restriction enzymes and inserted into the vector pcDNA3-Topaze cleaved with the same enzymes. The stop codon of the YFP was then removed by site-directed mutagenesis, so as to obtain the vector pcDNA3-YFP-MY047. The vector pcDNA3-MY047-YFP was obtained by insertion of the DNA fragment obtained by PCR on the vector pcDNA3-YFP-MY047 and cleaved with BamH1, then inserted into the vector pcDNA3-YFP cleaved with the same enzyme. Insertion of the same fragment into the vector pcDNA3-Rluc cleaved with BamH1 made it possible to obtain the vector pcDNA3-MY047-Rluc. Two consecutive PCR reactions were carried out so as to obtain amplification of the mouse U6 promoter followed by the hairpin iRNA sequence of sequence SEQ ID No. 42. In a first reaction, a first pair of primers: U6 sense, 5'-CCATCTAGGCCAAGCT-TATCCGACGCCGCCATCTC-3' SEQ ID No. 41 and that corresponding to the sense sequence of the target followed by a sequence forming the loop (SEQ ID No. 39). This PCR product was then used in a second reaction with the same sense primer (U6 sense) and a second primer corresponding to the antisense sequence of the target preceded by the same sequence forming the loop (SEQ ID No. 40). The various PCR products corresponding to the various hairpin iRNAs were inserted into the vector PCR3.1 using the TA-cloning kit (INVITROGEN, Groningen, the Netherlands), to give the plasmids PCR3.1-RNAi 14. All the constructs were verified by sequencing.

Cell Culture and Transfection

The HEK 293, COS-7 and HeLa cells were cultured in DMEM supplemented with 10% (v/v) of SVF, 4.5 g/liter of glucose, 100 U/ml of penicillin, 0.1 mg/ml of streptomycin and 1 $mmol.L^{-1}$ of glutamine (all from Life Technologies, Gaithersburg, Md.). The transient transfections were carried out with the FuGene 6 reagent (Roche, Basle, Switzerland) according to the supplier's instructions, except for the Ltk cells. The latter were transfected using the DEAE dextran technique: the cells are rinsed twice with PBS, and then 1 ml of a mixture of 2 μg of DNA, DMEM, 20 mM Hepes, 4.5 g/liter of glucose and 200 μg of DEAE-dextran is added to the cells. After incubation for 8 hours, the medium is removed and the cells are then incubated for 1 hour 30 min with 1 ml of DMEM, 4.5 g/liter of glucose and 10% DMSO. The cells are finally rinsed and then incubated with the culture medium.

Preparation of Membranes and Solubilization

The membranes were prepared as previously described (19), and resuspended in 75 $mmol.L^{-1}$ Tris (pH 7.4), 12.5 $mmol.L^{-1}$ $MgCl_2$ and 5 $mmol.L^{-1}$ EDTA, and immediately used in BRET experiments.

SDS PAGE and Western Blotting

The total lysates were prepared by washing the cells once with cold PBS (pH 7.4) and denatured by adding loading buffer (30 $mmol.L^{-1}$ Tris HCl, pH 6.8, 1% glycerol, 5% SDS, 50 $mmol.L^{-1}$ DTT and 0.05% bromophenol blue). The total lysates or the immunoprecipitates were incubated for 10 minutes at 90° C. and then loaded onto 10% acrylamide gel for separation by electrophoresis (SDS-PAGE). The proteins were then transferred onto a nitrocellulose membrane and revealed with specific primary antibodies: anti-YFP (8367-1 Living Colors) diluted to 1/200, anti-myc A14 (sc-789 TEBU Peprotech Santa Cruz Biotechnology) diluted to 1/500, then a secondary antibody coupled to peroxidase (anti-rabid goat IgG; Jackson Immunoresearch Laboratories, Inc., West Baltimore Pike) diluted to 1/10,000. The immunoreactive bands were revealed with an ECL kit (Pharmacia Biotech).

Immunoprecipitation

Two days after transfection, the cells were washed once with cold PBS, and the proteins were extracted by incubation for 15 minutes in lysis buffer (1×PBS, 1% Nonidet P40, 0.5% sodium deoxycholate, 0.1% SDS, 0.02% $NaN_3$, 10 mg.$L^{-1}$ benzamidine and 5 mg/$L^{-1}$ trypsin inhibitors). The lysate was centrifuged at 18000 g for 15 min and the supernatant was then incubated for 3 hours at 4° C. with an anti-myc antibody coupled to agarose beads (sc 40AC TEBU preprotech, Santa CRUZ Biotechnology). The precipitates were washed three times with cold lysis buffer and denatured with loading buffer for SDS-PAGE.

Radiobinding Experiments

The radiobinding experiments were carried out as previously described (Barr et al., (1999) J Biol Chem, 274, 21416-21424), with slight modifications. To determine the surface leptin binding, the cells cultured in the 6-well plates were washed twice with cold PBS and incubated in the binding buffer (DMEM, 25 mmol.$L^{-1}$ Hepes, pH 7.4, 1% BSA) containing 100,000 cpm/well of $^{125}$I-leptin (PerkinElmer life sciences, Paris, France) in the presence or absence of 200 nmol.$L^{-1}$ of leptin (PreproTech Inc, USA) for 4 h at 4° C. The cells were washed twice with cold PBS, then lyzed in 1N NaOH, and the radioactivity was determined in a γ counter. To determine the total binding of leptin, the cells cultured in dishes 10 cm in diameter were solubilized in 1.5 ml of binding buffer containing 0.15% of digitonin, for 2 h at 4° C. The extracts were centrifuged for 30 min at maximum speed and at 4° C. The supernatants (0.2 ml) were incubated with 100,000 cpm of $^{125}$I-leptin in the presence or absence of 200 nmol.$L^{-1}$ of leptin, in a total volume of 0.25 ml, with constant rotation at 4° C. overnight. 0.5 ml of γ-globulin (1.25 mg/ml) and 0.5 ml of polyethylene glycol 6000 (25% w/v) were added in order to precipitate the receptor-ligand complexes, which were centrifuged at 17,000 g for 3 min. The pellet was washed once with 1 ml of polyethlyene glycol 6000 (12% w/v) and the radioactivity was determined in a γ-counter.

Reporter Gene Activation Assay

The HeLa cells cultured in wells of 6-well plates were cotransfected with 500 ng of a reporter plasmid expressing firefly luciferase under the control of STAT3 or STAT5 factor response elements (a gift from Dr. Levy, University of New York, N.Y., USA), 250 pg of the expression vector pcDNA3-Renilla luciferase (used as internal standard between the samples) and with 500 ng of the various OB-R expression vectors or the vector alone. 48 h after transfection, the cells were starved overnight in Optimem medium (Invitrogen, Groningen, The Netherlands) containing 1% of BSA, before stimulation with 10 nmol.$L^{-1}$ of leptin, or no stimulation, for 48 h. The cells were then washed once with PBS, then lyzed in passive lysis buffer (Promega Corporation, Madison, Wis.) for 15 min at ambient temperature. The total lysates were centrifuged for 2 min at 15,000 g and the supernatants were used in an assay to measure luciferase (Dual Luciferase Assay System from Promega Corporation, Madison, Wis.) using a Berthold luminometer (Lumat LB 9507). The results are expressed as ratio of firefly luciferase activity to Renilla luciferase activity.

BRET Measurements in Microplates 48 h after transfection, the COS-7, HeLa or HEK 293 cells expressing the OB-R fusion proteins were detached and washed in PBS. 1-2x$10^5$ cells were distributed into wells of optiplate plates (96-well, Packard Instrument Company, Meriden, Conn.) in the presence or absence of the ligands, and incubated at 25° C. Alternatively, the same procedure was carried out with membranes prepared from the cells expressing the various constructs. The substrate, coelenterazine h (Molecular Probes, Eugene, Oreg.), was added at a final concentration of 5 μmol.$L^{-1}$ and the readings were carried out with a Fusion™ luminometer/fluorimeter (Packard Instrument Company, Meriden, Conn.), which makes it possible to measure luminescence through two filters (luciferase filter: 485±10 nm; YFP filter: 530±12.5 nm). The BRET ratio was defined as the difference in emission at 530 nm/485 nm of the cells cotransfected with the Luc and YFP fusion proteins and the emission at 530 nm/485 nm of the Luc fusion protein transfected alone into the cells. The results are expressed as milliBRET units (mBU), 1 mBRET corresponding to the values of the differences in the ratios multiplied by 1000.

RT-PCR

The total RNAs were extracted by the method of Chomczynski and Sacchi (Chomcynzki P., and Sacchi N. (1987) Anal. Biochem. 162, 156-159). 1 μg of RNA is denatured for 5 minutes at 68° C. and then abruptly cooled for 5 min at 4° C. The denatured sample is reversed transcribed for 1 h at 37° C. in 20 μl of RT reaction medium (5 μmol.$L^{-1}$ PdN6, 10 μmol.$L^{-1}$ DTT, 50 mmol.$L^{-1}$ Tris-HCl, pH=8.3, 75 mmol.$L^{-1}$ KCl, 5 mmol.$L^{-1}$ $MgCl_2$, 500 μmol.$L^{-1}$ dNTP, 200U RT-MMLV). A 2.5 μl aliquot of this reaction is used for a PCR reaction in a final volume of 25 μl (40 mmol.$L^{-1}$ Tris-HCl, pH 8.4: 100 mmol.$L^{-1}$ KCl; 1.5 mmol.$L^{-1}$ $MgCl_2$; 0.2 mmol.$L^{-1}$ of each dNTP; 0.141 mmol.$L^{-1}$ of primers specific for OB-RGRP (human sense: CCGTGGCAGGAAGC SEQ ID No. 43, murine sense: GCAGCCACAGCCCCAGCTCC SEQ ID No. 44, antisense: CAGCCACACGAGCAAG SEQ ID No. 45) and 0.035 mmol.$L^{-1}$ of primers specific for glyceraldehyde phosphate dehydrogenase (GAPDH) (sense: GGAGAAGGCTGGGGC SEQ ID No. 46, antisense: GATGGCATGGACTGTGG SEQ ID No. 47) and 2.5U of TAQ DNA polymerase). The following protocol was used for the PCR reaction: Initial denaturation for 3 min at 94° C., then 22 to 30 cycles of denaturation (20 sec at 94° C.), hybridization (20 sec at 59° C.), elgonation (20 sec at 72° C.) followed by a final elongation of 7 min at 72° C.

An aliquot of the PCR reaction was loaded onto a 2% agarose gel in order to separate the reaction products by electrophoresis. The expected sizes of fragments of GAPDH and of OBR-GRP are, respectively, 229 bp and 334 bp.

Oligonucleotide Synthesis

The oligonucleotides were synthesized on an automatic DNA synthesizer ("Expedite MOSS" 8909 model from Applied Biosystems) by standard phosphoramidite chemistry and iodine oxidation. The demethylation was carried out with a 0.2 mol.$L^{-1}$ solution of 3H-1,2-benzodithiol-3-one 1,1-dioxide in acetonitrile for 120 s. The detachment from the support and the deprotection were carried out in concentrated ammonia (18 h at 55° C.), and the oligonucleotides were then purified by precipitation. The deprotection product was precipitated with 10 volumes of 1-butanol; the pellet taken up in one volume of 0.3 mol.$L^{-1}$ NaCl was reprecipitated by adding 4 volumes of ethanol.

The analysis on a 20% polyacrylamide gel (in a buffer of 8 mol.$L^{-1}$ urea and 454 mmol.$L^{-1}$ Tris-borate, at pH 7.0) showed a greater than 80% proportion of product of expected length.

Transfection of the Synthetic Antisense Oligodeoxynucleotides and Interfering RNA Duplex For the transfection of 300,000 cells cultured in a well of a 6-well plate, 10 μl of antisense ODN at 20 μmol.$L^{-1}$ or 10 μl of the interfering RNA duplex at 20 μM were diluted in 175 μl of DMEM. 3 μl of oligofectamine (Invitrogen, Groningen, The Netherlands) and 12 μl of DMEM were incubated in a second tube for 10 min at ambient temperature. The oligofectamine/DMEM mixture was then added to the diluted antisense ODN, vortexed and incubated for 20 min at ambient temperature. During this time, the cells were washed once with PBS and once with DMEM, and then covered with 800 μl of DMEM. The ODN/oligofectamine mixture was then added dropwise to the cells and incubated for 4 h at 37° C., before adding 500 μl of DMEM supplemented with 30% serum.

EXAMPLE 1

Topology and Cellular Location of OB-RGRP

To study the topology and the subcellular location of OB-RGRP, the protein was tagged with the yellow variant of green fluorescent protein (YFP) at the end of its C-terminal tail. The fusion protein was expressed in HeLa cells and its location was determined by fluorescence microscopy.

The results show that the fusion protein is preferentially targeted to the perinuclear membranes and into intracellular vesicles. Similar results were observed in HEK cells. No colocalization with cytoplasmic and nuclear proteins was observed, confirming the location of OB-RGRP in membranes (not shown). The exact nature of the membrane compartment was determined by colocalization studies with markers specific for subcellular compartments. A strong colocalization was observed with the invariant chain of MHC II molecules, a marker for the endocytic compartment.

Initial analysis of the topology of OB-RGRP suggested an organization in 3 transmembrane (TM) domains (Bailleul et al. (1997) Nucleic Acids Research 25, 2752-2758). A similar organization has been proposed for MY047 (Huang et al. (2001) Biochimica et Biophysica acta. Gene structure and expression 327-331). However, a new analysis of the hydrophobicity profile of the various protein sequences available for OB-RGRP and MY047 is also compatible with a 4-TM model (FIG. 2). The topology differs profoundly between these two models. In the 3-TM model, the N- and C-terminal ends are located on each side of the membrane, whereas in the 4-TM model, the two tails are oriented on the same side of the membrane (FIG. 3*a*). To determine the correct model, we used the resonance energy transfer (BRET) method which has recently been developed to follow protein-protein interactions in living cells (Xu et al. (1999) Proc Natl Acad Sci USA 96, 151-156). In the event of physical proximity (<100 Å between the two interacting proteins, an energy transfer can take place between the energy-donor (Luc) and the energy-acceptor (YFP), fused to the two proteins of interest. We tagged the N-terminal tail of OB-RGRP with YFP, and the C-terminal tail with luciferase, and we observed the energy transfer by measuring BRET with this double fusion protein. The 3-TM model does not allow transfer since the two BRET partners are separated by the lipid bilayer. On the other hand, the 4-TM model predicts strong energy transfers since the two partners are located on the same side of the membrane. As shown in FIG. 3*b*, a very strong energy transfer was detected for the double fusion protein in the intact cells, indicating that OB-RGRP has 4-TMs.

This set of results suggests that OB-RGRP is a membrane-bound protein with 4 transmembrane domains, having 3 short loops and short N- and C-terminal ends oriented on the same side of the membrane. OB-RGRP is mainly located in intracellular compartments.

EXAMPLE 2

Oligomerization of OB-RGRP

Oligomerization is a property common to various proteins, including membrane-bound proteins such as tyrosine kinase receptors, cytokine receptors and phosphotyrisine phosphatases. It has been shown that this oligomerization plays an important role in the function of these proteins. To obtain elements in the function of OB-RGRP, we wanted to know whether this protein oligomerizes.

OB-RGRP was tagged with YFP at its C-terminal tail and expressed in HeLa cells. The proteins were separated by polyacrylamide gel electrophoresis under denaturing conditions (SDS-PAGE) and immunoblotting experiments were carried out with an anti-YFP antibody. FIG. 4*a* reveals several bands specific for OB-RGRP-YFP, corresponding to monomeric and dimeric forms and oligomeric complexes. Similar results were obtained with OB-RGRP tagged at the N-terminal, either with YFP or a myc epitope (FIG. 4*a,b*). Formation of the OB-RGRP oligomers was observed on total cell extracts after immunoprecipitation. The use of a crosslinker on whole cells stabilizes the dimeric complexes, indicating that the dimeric form is the predominant form of OB-RGRP in intact cells (FIG. 4*a*).

Surprisingly, OB-RGRP has unexpected properties since the oligomers are stable in the presence of various denaturing and/or dissociating agents such as 5% SDS, 1% Triton X-100, 1% Nonidet P40, 1% digitonin, 50 mmol.$L^{-1}$ DTT and 2% β-mercaptoethanol. However, similar observations were obtained for other membrane-bound proteins such as glycophorin A and G protein-coupled β2-adrenergic receptors. Studies on these proteins show, respectively, that LIXXGVXXG and LXXXGXXXGXXXL motifs in the transmembrane domains are essential for oligomer formation. Similar motifs were identified in the membrane regions of OB-RGRP.

Figure 5:
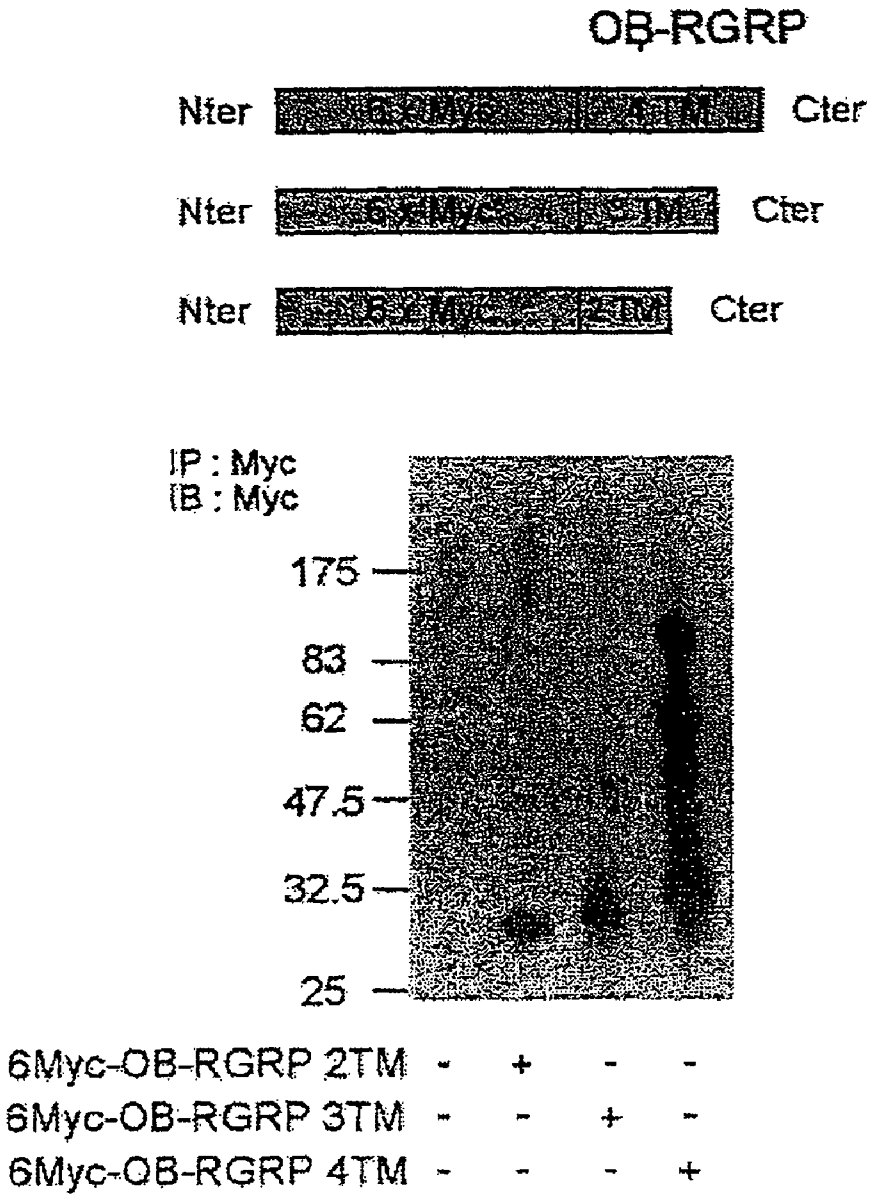

To identify the molecular determinants involved in the dimerization, we prepared OB-RGRP constructs exhibiting progressive deletions of the C-terminal tail (FIG. 5). A construct containing the first two potential TMs loses the ability to form oligomers. Addition of the $3^{rd}$ TM restores the possibility of forming dimers. However, the complete oligomerization profile was only observed in the presence of the 4 potential TMs.

Oligomers of membrane-bound proteins can be artifacts induced during the preparation of samples (solubilization, denaturation, etc.). For this reason, it is important to verify the oligomerization of proteins in living cells. Recently developed energy transfer techniques such as BRET make it possible to follow such protein-protein interactions in living cells. Fusion proteins of OB-RGRP with luciferase and YFP were used to follow OB-RGRP oligomerization in living cells. Coexpression of the OB-RGRP-YFP or YFP-OB-RGRP constructs with the OB-RGRP-Luc construct induces an energy transfer (FIG. 6*a*). The specificity of this interaction was shown by the lack of energy transfer during the coexpression with two different fusion proteins: β-arrestine2-YFP (Angers et al. (2000) Proc Natl Acad Sci USA 97, 3684-3689), or melatonin-Luc MT2 receptor (Ayoub et al. (2002) J Biol Chem 277, 21522-21528). We then expressed various ratios of the BRET partners (FIG. 6*b*). The BRET signal is increased in a hyperbolic manner as a function of the OB-RGRP-YFB/OB-RGRP-Luc ratio, reaching an asymptote which corresponds to saturation of the energy-donor molecules (OB-RGRP-Luc) by the acceptor molecules (OB-RGRP-YFP), which is expected in the case of a specific interaction.

Collectively, these results show that OB-RGRP is a dimeric membrane-bound protein which can also be involved in high molecular weight oligomeric complexes. The $3^{rd}$ and $4^{th}$ potential transmembrane domains appear to be important for oligomer formation.

EXAMPLE 3

Interaction between OB-R and OB-RGRP and MY047

Figure 7:
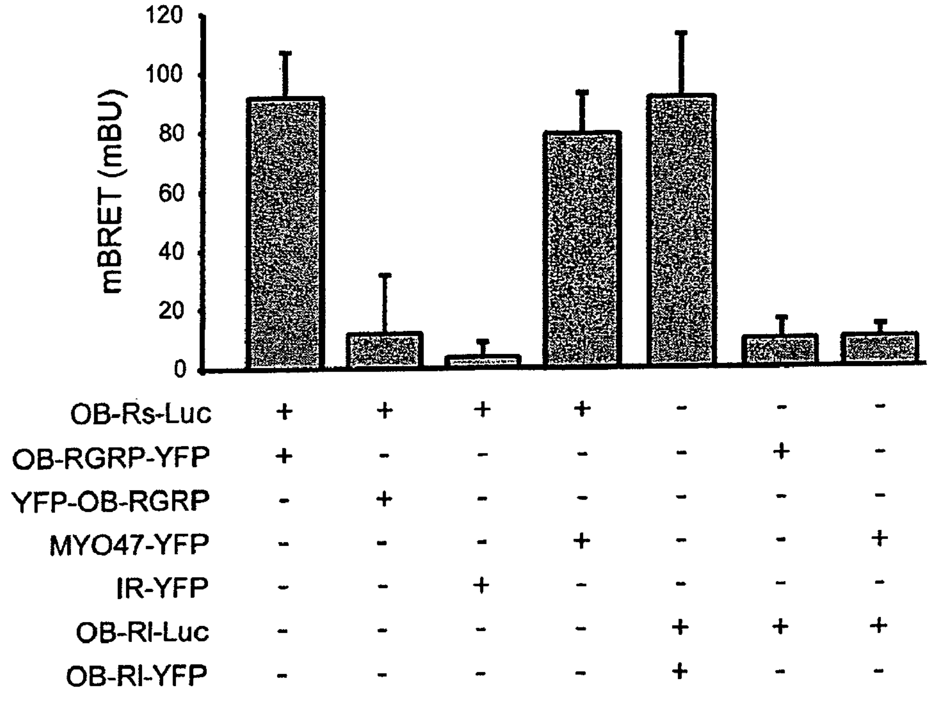

We used BRET technology to study a possible interaction between OB-R and OB-RGRP in living cells. An energy transfer was constitutively observed in the cells coexpressing the OB-$R_s$-Luc construct and the OB-RGRP-YFP construct, indicating proximity of the interaction partners (FIG. 7). The same results were obtained in cells coexpressing OB-$R_s$-Luc and the MYO47-YFP construct, and also in the reverse orientation: in cells coexpressing OB-RGRP-Luc and OB-$R_s$-YFP, or in cells coexpressing MYO47-Luc and OB-$R_s$-YFP. The specificity of these interactions was confirmed by the lack of energy transfer between OB-$R_s$-Luc, OB-RGRP-Luc, MYO47-Luc and a construct of the insulin receptor tagged with YFP (Boute et al. (2001) Mol Pharmacol 60, 640-645), and also in the reverse orientation: by the lack of energy transfer between a construct of the insulin receptor tagged with Luc and the OB-$R_s$-YFP, OB-RGRP-YFP and MYO47-YFP construct. Coexpression of OB-$R_s$-Luc and an OB-RGRP or MYO47 construct exhibiting the YFP tag at the N-terminal produces no significant signal, confirming the specificity of interaction with OB-RGRP-YFP and MYO47, and indicates that the N-terminal end of OB-RGRP and MYO47 must be involved in the interaction with OB-R.

No significant energy transfer was observed in the cells coexpressing the OB-$R_l$-Luc and OB-RGRP-YFP or YFP-OB-RGRP constructs. This is not due to a lack of functional OB-$R_l$-Luc expression since a specific BRET signal was observed in cells coexpressing OB-$R_l$-YFP in order to follow OB-R dimerization. The lack of BRET between the OB-$R_l$-Luc and OB-RGRP-YFP fusion proteins does not exclude a direct interaction between these two proteins since this may be explained by the fact that the distance between the two BRET partners (Luc and YFP) is greater than 100 Å, the maximum distance for obtaining a transfer. This should be the case since the N- and C-terminal ends of OB-RGRP should be located close to the transmembrane region of OB-R, whereas the C-terminal end of OB-$R_l$ should more probably point toward the cytoplasm due to its long intracellular tail of approximately 300 amino acids. Given that the short and long isoforms of OB-R share the same trans- and juxtamembrane regions and that the interaction of OB-RGRP with OB-$R_s$ is located at this level, it is probable that OB-RGRP interacts with OB-$R_l$ in the same way as with OB-$R_s$.

EXAMPLE 4

Effect of the Overexpression of OB-RGRP on OB-R Signaling

Constructs containing STAT3- or STAT5-response elements upstream of a luciferase reporter gene were coexpressed with OB-$R_l$ in the presence or absence of various OB-RGRP constructs (FIG. 8). The two constructs were activated by leptin in a dose-dependent manner, with an EC50 of approximately 50 pM. Similar results were obtained in HEK 293 cells stably expressing a reporter gene for STAT3. The overexpression of various OB-RGRP constructs had no reproducible effect on this activation, indicating that OB-RGRP is not a limiting factor.

EXAMPLE 5

Effect of the Overexpression of OB-RGRP on the Expression of OB-R at the Surface In yeast knockout for OB-RGRP (Vps55), protein transport is disturbed between the golgi and the vacuoles (Belgareh-Touze et al. (2002) Molecular Biology Of The Cell 13, 1694-1708). Although OB-R are activated only when they are expressed at the plasma membrane, a considerable amount of receptors is accumulated in intracellular compartments (Barr, et al. (1999) J Biol Chem, 274, 21416-21424) (Lundin et al. (2000) Biochimica and Biophysica Acta 1499, 130-138). For this reason, we tested the effects of the overexpression of OB-RGRP on the expression of OB-R at the cell surface.

Figure 9:
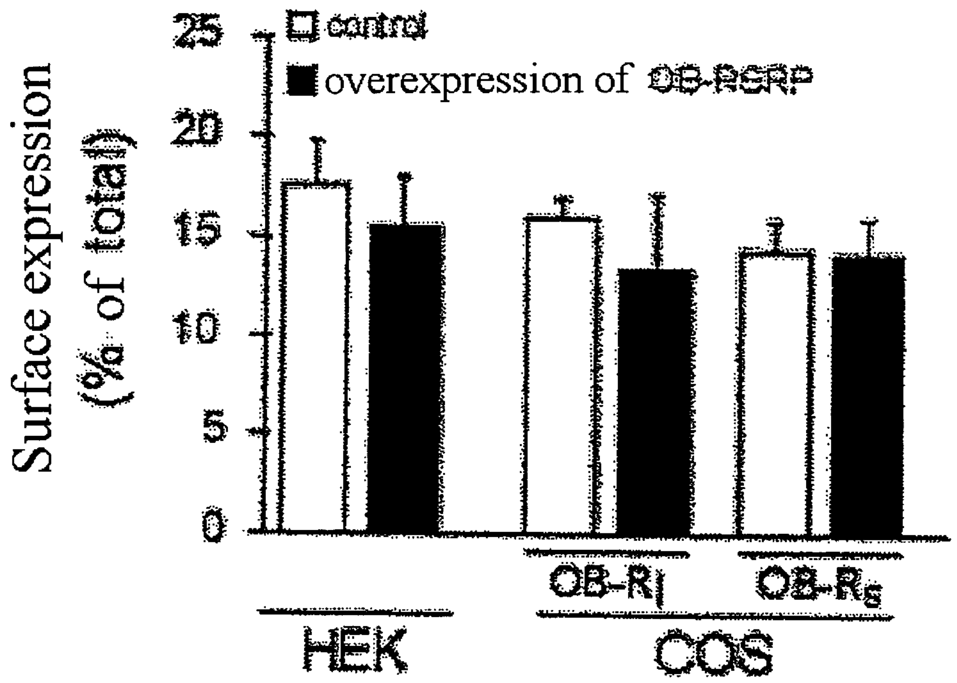

The receptor distribution was studied by $^{125}$I-leptin-binding experiments. In agreement with other authors (Barr et al., 1999), we showed that only 10-20% of the OB-$R_l$ and OB-$R_s$ receptors are expressed at the surface of transfected COS cells (FIG. 9) and of HeLa cells. This is not an artifact due to the expression of exogenous receptors since similar values are obtained in HEK 293 cells expressing endogenous OB-R receptors (FIG. 9). The overexpression of OB-RGRP showed no modification of the total amount in the cells, nor of the % of receptors expressed at the surface (FIG. 9).

EXAMPLE 6

Characterization of OB-RGRP Specific Antisense Deoxynucleotides

OB-RGRP appears to have ubiquitous expression; for this reason, the decrease in expression of this protein was chosen as an alternative approach for studying its role in OB-R function. Fourteen antisenses specific for OB-RGRP (AS 1 to 14; SEQ ID No. 22 to SEQ ID No. 34 and SEQ ID No. 2) and two random antisenses (AS 15 and 16; SEQ ID No. 35 and SEQ ID No. 36) were chosen (see FIG. 1), synthesized, and then tested for their ability to inhibit OB-RGRP expression using semiquantitative RT-PCR experiments in HeLa cells expressing OB-RGRP endogenously (FIG. 10). Only one of these antisenses (AS-14), derived from the untranslated 3' region of the OB-RGRP mRNA, interferes with OB-RGRP expression. Labeling of this antisense with the Cy3 fluorophore made it possible to show that all of the cells were transfected under our experimental conditions, in our various experiments.

EXAMPLE 7

Effect of the Various Interfering RNAs on the Level of OB-RGRP Messengers Observed by Semi-quantitative RT-PCR In order to decrease the expression of OB-RGRP, an alternative approach was to use interfering RNAs. For this, we used, firstly, a synthetic interfering RNA candidate sequence directed against both the human and murine sequence (FIG. 11*a*) and, secondly, a vector (PCR3.1-RNAi 14) expressing a hairpin interfering RNA directed against a murine sequence of OB-RGRP (FIG. 11*c*).

The ability of the iRNAs to decrease the endogenous OB-RGRP expression was tested by RT-PCR.

The synthetic iRNA transfected into HELA cells (of human origin) causes a decrease in the expression of human OB-RGRP.

Transfection of the vector PCR3.1-RNAi-14 causes the same effect in L cells (of murine origin).

EXAMPLE 8

Figure 12:
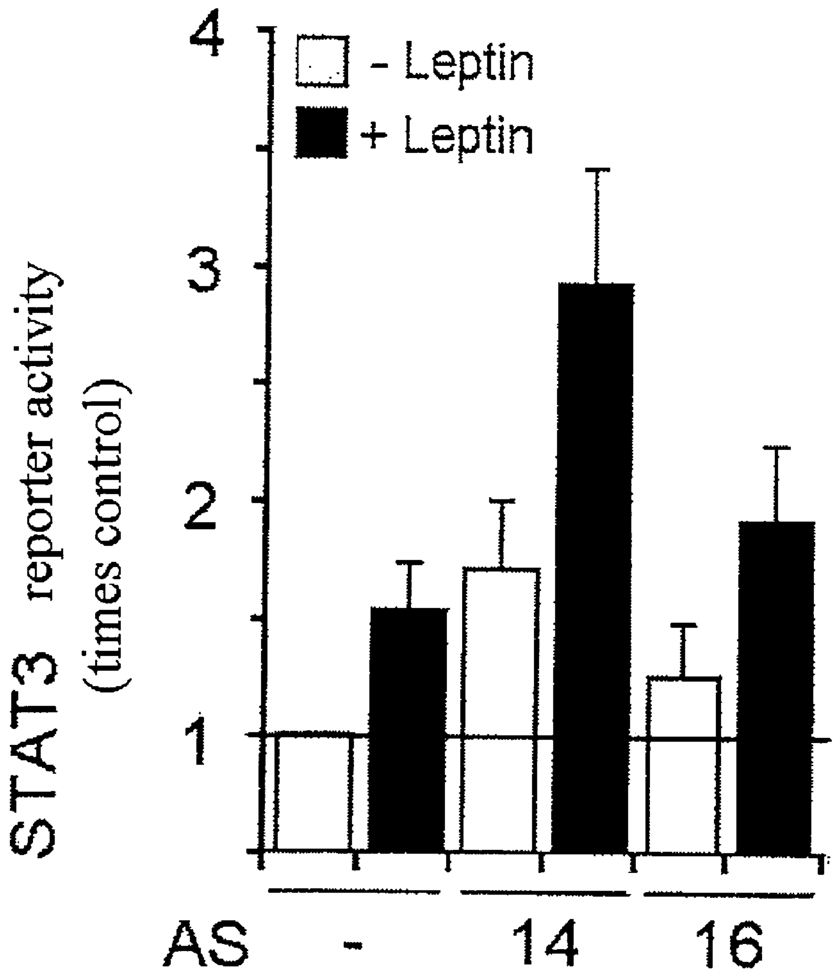
Figure 13:
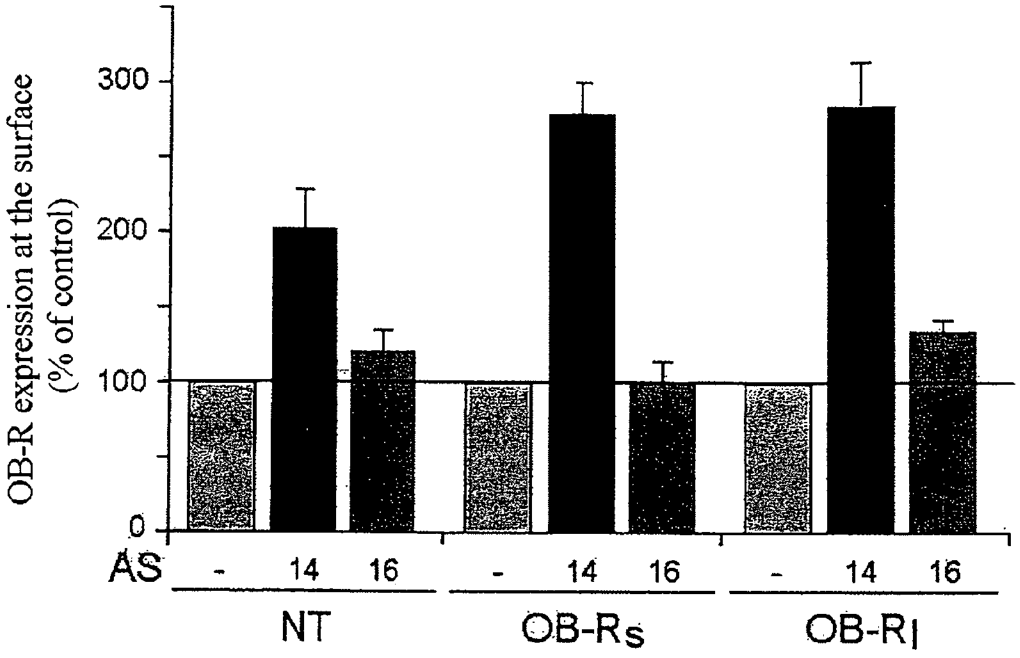

Effect of the OB-RGRP-specific Antisense on the Signaling and Surface Expression of the OB-R HeLa cells were first cotransfected with the expression vectors for OB-$R_l$ and the reporter gene for STAT3, and then with the antisenses. Leptin causes an approximately 1.5-fold increase in the basal activation of the reporter gene for STAT3 in the control cells without antisense, or with a control antisense (AS16) (FIG. 12). In the cells transfected with the antisense specific for OB-RGRP (AS-14), the basal and leptin-stimulated signaling is relatively increased compared to the control conditions. This shows that activation of the JAK/STAT pathway is increased in the cells exhibiting a decrease in OB-RGRP expression. These observations may be explained by an inhibitory effect of OB-RGRP on the basal and OB-R-stimulated activity and, in this case, OB-RGRP can be considered to be a regulator of OB-R signaling. Another alternative is that OB-RGRP might regulate the expression of the surface receptors by limiting the number of OB-R reaching the cell surface. This is in agreement with the fact that only 10 to 20% of the receptors expressed reach the cell surface. In this hypothesis, the decrease in OB-RGRP expression should increase the number of receptors at the cell surface, which should increase the signaling by these receptors. To test this hypothesis, we quantified the number of OB-$R_l$ and OB-$R_s$ receptors expressed at the cell surface in the presence (control) and absence (AS-14) of OB-RGRP (FIG. 13). Transfection of the random antisense showed no effect on the number of receptors expressed at the cell surface, whereas that of the specific antisense (AS-14) caused a 3-fold increase in the number of OB-R expressed at the plasma membrane. Similar results were obtained in nontransfected HeLa cells expressing endogenous receptors. Under these experimental conditions, the total number of receptors, measured by $^{125}$I-leptin-binding experiments, showed no significant variations.

All our results are consistent with the role of OB-RGRP in yeast, in protein transport. The increase in surface expression of OB-R appears to be involved in the increase in signaling observed. However, we cannot entirely exclude the hypothesis that OB-RGRP directly regulates OB-R activity. The application of specific antisenses directed against OB-RGRP should be useful for increasing OB-R signaling in leptin-related disorders, such as human obesity, in which resistance to leptin is observed, characterized by an unadapted response to this hormone. The increase in expression of the receptors at the cell surface and in their signaling should be important for increasing the response to leptin in the case of human obesity, firstly by increasing leptin transport to the brain across the blood-brain barrier and, secondly, by increasing OB-R signaling in the hypothalamus.

The interaction between OB-RGRP and OB-$R_s$ implies that the action of OB-RGRP takes place via this direct interaction with the receptors and that preventing this interaction may lead to the effects of the specific antisense ODN being reproduced. We propose using the BRET test of the interactions between OB-RGRP and OB-$R_s$, and MYO47 and OB-$R_s$, described above, as a test for screening molecules which may modulate this interaction. This test may be carried out either on whole or permeabilized cells coexpressing the proteins from fusions of the OB-RGRP and OB-$R_s$, or MYO47 and OB-$R_s$ BRET partners, or on membrane fractions derived from these cells.

We claim:

1. An antisense oligonucleotide made up of up to 50 nucleotide units complementary to nucleotides of a corresponding portion of the sequence SEQ ID NO. 21 and which inhibits the expression of OB-RGRP, said antisense oligonucleotide comprising AS-14 (SEQ ID NO. 2).

2. A composition containing the antisense oligonucleotide, as claimed in claim 1 and acceptable excipients.

3. The antisense nucleotide of claim 1 made up of up to 30 nucleotide units.

4. A composition containing the antisense oligonucleotide, as claimed in claim 3 and acceptable excipients.

* * * * *

SEQUENCE LISTING

```
<160> NUMBER OF SEQ ID NOS: 51

<210> SEQ ID NO 1
<211> LENGTH: 648
<212> TYPE: DNA
<213> ORGANISM: Homo sapiens

<400> SEQUENCE: 1

cactttattc tgattacagt gcattgaatt tcttagaact catactatct gtatacatgt      60

gcacatgcgg cattttacta tgaaatttaa tatgctgggt tttttaatac ctttatatat     120

catgttcact ttaagaaaga cttcataagt aggagatgag ttttattctc agcaaataga     180

cctgtcaaat ttagattatg ttactcaaat tatgttactt gtttggctgt tcatgtagtc     240

acggtgctct cagaaaatat attaacgcag tcttgtaggc agctgccacc ttatgcagtg     300

catcgaaacc ttttgcttgg ggatgtgctt ggagaggcag ataacgctga agcaggcctc     360

tcatgaccca ggaaggccgg ggtggatccc tctttgtgtt gtagtccatg ctattaaaag     420

tgtggcccac agaccaagag cctcaacatt tcctagagcc ttattagaaa tgcagaatct     480

gaagccccac tctggaccca ggacattttg atgagatcca aaggagttgt atgcacatga     540

aagtttgaga agcatcatca tagagaagta aacatcacac ccaacttcct tatctttcca     600
```

-continued

```
gtggctaaac cacttaacct ctctgggtgt tacctgctca tttgttta              648


<210> SEQ ID NO 2
<211> LENGTH: 20
<212> TYPE: DNA
<213> ORGANISM: Artificial Sequence
<220> FEATURE:
<223> OTHER INFORMATION: AS14
<220> FEATURE:
<221> NAME/KEY: misc_feature
<223> OTHER INFORMATION: antisens AS14

<400> SEQUENCE: 2

aatgccgcat gtgcacatgt                                              20


<210> SEQ ID NO 3
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 3

atg gcg ggc gtt aaa gct ctc gtg gca tta tcc ttc agt ggg gct att      48
Met Ala Gly Val Lys Ala Leu Val Ala Leu Ser Phe Ser Gly Ala Ile
1               5                   10                  15

gga ctg act ttt ctt atg ctg gga tgt gcc tta gag gat tat ggc gtt      96
Gly Leu Thr Phe Leu Met Leu Gly Cys Ala Leu Glu Asp Tyr Gly Val
            20                  25                  30

tac tgg ccc tta ttc gtc ctg att ttc cac gcc atc tcc ccc atc ccc     144
Tyr Trp Pro Leu Phe Val Leu Ile Phe His Ala Ile Ser Pro Ile Pro
        35                  40                  45

cat ttc att gcc aaa aga gtc acc tat gac tca gat gca acc agt agt     192
His Phe Ile Ala Lys Arg Val Thr Tyr Asp Ser Asp Ala Thr Ser Ser
    50                  55                  60

gcc tgt cgg gaa ctg gca tat ttc ttc act act gga att gtt gtt tct     240
Ala Cys Arg Glu Leu Ala Tyr Phe Phe Thr Thr Gly Ile Val Val Ser
65                  70                  75                  80

gcc ttt gga ttt cct gtt att ctt gct cgt gtg gct gtg atc aaa tgg     288
Ala Phe Gly Phe Pro Val Ile Leu Ala Arg Val Ala Val Ile Lys Trp
                85                  90                  95

gga gcc tgc ggc ctt gtg ttg gca ggc aat gca gtc att ttc ctt aca     336
Gly Ala Cys Gly Leu Val Leu Ala Gly Asn Ala Val Ile Phe Leu Thr
            100                 105                 110

att caa ggg ttt ttc ctt ata ttt gga aga gga gat gat ttt agc tgg     384
Ile Gln Gly Phe Phe Leu Ile Phe Gly Arg Gly Asp Asp Phe Ser Trp
        115                 120                 125

gag cag tgg tag                                                     396
Glu Gln Trp
    130


<210> SEQ ID NO 4
<211> LENGTH: 131
<212> TYPE: PRT
<213> ORGANISM: Homo sapiens

<400> SEQUENCE: 4

Met Ala Gly Val Lys Ala Leu Val Ala Leu Ser Phe Ser Gly Ala Ile
1               5                   10                  15

Gly Leu Thr Phe Leu Met Leu Gly Cys Ala Leu Glu Asp Tyr Gly Val
            20                  25                  30

Tyr Trp Pro Leu Phe Val Leu Ile Phe His Ala Ile Ser Pro Ile Pro
```

-continued

```
        35                  40                  45

His Phe Ile Ala Lys Arg Val Thr Tyr Asp Ser Asp Ala Thr Ser Ser
    50                  55                  60

Ala Cys Arg Glu Leu Ala Tyr Phe Phe Thr Thr Gly Ile Val Val Ser
65                  70                  75                  80

Ala Phe Gly Phe Pro Val Ile Leu Ala Arg Val Ala Val Ile Lys Trp
                85                  90                  95

Gly Ala Cys Gly Leu Val Leu Ala Gly Asn Ala Val Ile Phe Leu Thr
            100                 105                 110

Ile Gln Gly Phe Phe Leu Ile Phe Gly Arg Gly Asp Asp Phe Ser Trp
        115                 120                 125

Glu Gln Trp
    130


<210> SEQ ID NO 5
<211> LENGTH: 1359
<212> TYPE: DNA
<213> ORGANISM: Artificial Sequence
<220> FEATURE:
<223> OTHER INFORMATION: OB RGRP LUC
<220> FEATURE:
<221> NAME/KEY: misc_feature
<223> OTHER INFORMATION: OB RGRP LUC
<220> FEATURE:
<221> NAME/KEY: CDS
<222> LOCATION: (1)..(1359)

<400> SEQUENCE: 5

atg gcg ggc gtt aaa gct ctc gtg gca tta tcc ttc agt ggg gct att       48
Met Ala Gly Val Lys Ala Leu Val Ala Leu Ser Phe Ser Gly Ala Ile
1               5                   10                  15

gga ctg act ttt ctt atg ctg gga tgt gcc tta gag gat tat ggc gtt       96
Gly Leu Thr Phe Leu Met Leu Gly Cys Ala Leu Glu Asp Tyr Gly Val
            20                  25                  30

tac tgg ccc tta ttc gtc ctg att ttc cac gcc atc tcc ccc atc ccc      144
Tyr Trp Pro Leu Phe Val Leu Ile Phe His Ala Ile Ser Pro Ile Pro
        35                  40                  45

cat ttc att gcc aaa aga gtc acc tat gac tca gat gca acc agt agt      192
His Phe Ile Ala Lys Arg Val Thr Tyr Asp Ser Asp Ala Thr Ser Ser
    50                  55                  60

gcc tgt cgg gaa ctg gca tat ttc ttc act act gga att gtt gtt tct      240
Ala Cys Arg Glu Leu Ala Tyr Phe Phe Thr Thr Gly Ile Val Val Ser
65                  70                  75                  80

gcc ttt gga ttt cct gtt att ctt gct cgt gtg gct gtg atc aaa tgg      288
Ala Phe Gly Phe Pro Val Ile Leu Ala Arg Val Ala Val Ile Lys Trp
                85                  90                  95

gga gcc tgc ggc ctt gtg ttg gca ggc aat gca gtc att ttc ctt aca      336
Gly Ala Cys Gly Leu Val Leu Ala Gly Asn Ala Val Ile Phe Leu Thr
            100                 105                 110

att caa ggg ttt ttc ctt ata ttt gga aga gga gat gat ttt agc tgg      384
Ile Gln Gly Phe Phe Leu Ile Phe Gly Arg Gly Asp Asp Phe Ser Trp
        115                 120                 125

gag cag tgg att ccg ggg gat cca ccg gct aga gcc acc atg acc agc      432
Glu Gln Trp Ile Pro Gly Asp Pro Pro Ala Arg Ala Thr Met Thr Ser
    130                 135                 140

aag gtg tac gac ccc gag cag agg aag agg atg atc acc ggc ccc cag      480
Lys Val Tyr Asp Pro Glu Gln Arg Lys Arg Met Ile Thr Gly Pro Gln
145                 150                 155                 160

tgg tgg gcc agg tgc aag cag atg aac gtg ctg gac agc ttc atc aac      528
Trp Trp Ala Arg Cys Lys Gln Met Asn Val Leu Asp Ser Phe Ile Asn
                165                 170                 175
```

-continued

```
tac tac gac agc gag aag cac gcc gag aac gcc gtg atc ttc ctg cac      576
Tyr Tyr Asp Ser Glu Lys His Ala Glu Asn Ala Val Ile Phe Leu His
            180                 185                 190

ggc aac gcc gct agc agc tac ctg tgg agg cac gtg gtg ccc cac atc      624
Gly Asn Ala Ala Ser Ser Tyr Leu Trp Arg His Val Val Pro His Ile
        195                 200                 205

gag ccc gtg gcc agg tgc atc atc ccc gat ctg atc ggc atg ggc aag      672
Glu Pro Val Ala Arg Cys Ile Ile Pro Asp Leu Ile Gly Met Gly Lys
    210                 215                 220

agc ggc aag agc ggc aac ggc agc tac agg ctg ctg gac cac tac aag      720
Ser Gly Lys Ser Gly Asn Gly Ser Tyr Arg Leu Leu Asp His Tyr Lys
225                 230                 235                 240

tac ctg acc gcc tgg ttc gag ctc ctg aac ctg ccc aag aag atc atc      768
Tyr Leu Thr Ala Trp Phe Glu Leu Leu Asn Leu Pro Lys Lys Ile Ile
                245                 250                 255

ttc gtg ggc cac gac tgg ggc gcc tgc ctg gcc ttc cac tac agc tac      816
Phe Val Gly His Asp Trp Gly Ala Cys Leu Ala Phe His Tyr Ser Tyr
            260                 265                 270

gag cac cag gac aag atc aag gcc atc gtg cac gcc gag agc gtg gtg      864
Glu His Gln Asp Lys Ile Lys Ala Ile Val His Ala Glu Ser Val Val
        275                 280                 285

gac gtg atc gag agc tgg gac gag tgg cca gac atc gag gag gac atc      912
Asp Val Ile Glu Ser Trp Asp Glu Trp Pro Asp Ile Glu Glu Asp Ile
    290                 295                 300

gcc ctg atc aag agc gag gag ggc gag aag atg gtg ctg gag aac aac      960
Ala Leu Ile Lys Ser Glu Glu Gly Glu Lys Met Val Leu Glu Asn Asn
305                 310                 315                 320

ttc ttc gtg gag acc atg ctg ccc agc aag atc atg aga aag ctg gag     1008
Phe Phe Val Glu Thr Met Leu Pro Ser Lys Ile Met Arg Lys Leu Glu
                325                 330                 335

ccc gag gag ttc gcc gcc tac ctg gag ccc ttc aag gag aag ggc gag     1056
Pro Glu Glu Phe Ala Ala Tyr Leu Glu Pro Phe Lys Glu Lys Gly Glu
            340                 345                 350

gtg aga aga ccc acc ctg agc tgg ccc aga gag atc ccc ctg gtg aag     1104
Val Arg Arg Pro Thr Leu Ser Trp Pro Arg Glu Ile Pro Leu Val Lys
        355                 360                 365

ggc ggc aag ccc gac gtg gtg cag atc gtg aga aac tac aac gcc tac     1152
Gly Gly Lys Pro Asp Val Val Gln Ile Val Arg Asn Tyr Asn Ala Tyr
    370                 375                 380

ctg aga gcc agc gac gac ctg ccc aag atg ttc atc gag agc gac ccc     1200
Leu Arg Ala Ser Asp Asp Leu Pro Lys Met Phe Ile Glu Ser Asp Pro
385                 390                 395                 400

ggc ttc ttc agc aac gcc atc gtg gag ggc gcc aag aag ttc ccc aac     1248
Gly Phe Phe Ser Asn Ala Ile Val Glu Gly Ala Lys Lys Phe Pro Asn
                405                 410                 415

acc gag ttc gtg aag gtg aag ggc ctg cac ttc agc cag gag gac gcc     1296
Thr Glu Phe Val Lys Val Lys Gly Leu His Phe Ser Gln Glu Asp Ala
            420                 425                 430

ccc gac gag atg ggc aag tac atc aag agc ttc gtg gag aga gtg ctg     1344
Pro Asp Glu Met Gly Lys Tyr Ile Lys Ser Phe Val Glu Arg Val Leu
        435                 440                 445

aag aac gag cag taa                                                 1359
Lys Asn Glu Gln
    450
```

<210> SEQ ID NO 6
<211> LENGTH: 452
<212> TYPE: PRT
<213> ORGANISM: Artificial Sequence
<220> FEATURE:

-continued

```
<223> OTHER INFORMATION: OB RGRP LUC
<220> FEATURE:
<221> NAME/KEY: misc_feature
<223> OTHER INFORMATION: OB RGRP LUC

<400> SEQUENCE: 6

Met Ala Gly Val Lys Ala Leu Val Ala Leu Ser Phe Ser Gly Ala Ile
1               5                   10                  15

Gly Leu Thr Phe Leu Met Leu Gly Cys Ala Leu Glu Asp Tyr Gly Val
            20                  25                  30

Tyr Trp Pro Leu Phe Val Leu Ile Phe His Ala Ile Ser Pro Ile Pro
        35                  40                  45

His Phe Ile Ala Lys Arg Val Thr Tyr Asp Ser Asp Ala Thr Ser Ser
    50                  55                  60

Ala Cys Arg Glu Leu Ala Tyr Phe Phe Thr Thr Gly Ile Val Val Ser
65                  70                  75                  80

Ala Phe Gly Phe Pro Val Ile Leu Ala Arg Val Ala Val Ile Lys Trp
                85                  90                  95

Gly Ala Cys Gly Leu Val Leu Ala Gly Asn Ala Val Ile Phe Leu Thr
            100                 105                 110

Ile Gln Gly Phe Phe Leu Ile Phe Gly Arg Gly Asp Asp Phe Ser Trp
        115                 120                 125

Glu Gln Trp Ile Pro Gly Asp Pro Pro Ala Arg Ala Thr Met Thr Ser
    130                 135                 140

Lys Val Tyr Asp Pro Glu Gln Arg Lys Arg Met Ile Thr Gly Pro Gln
145                 150                 155                 160

Trp Trp Ala Arg Cys Lys Gln Met Asn Val Leu Asp Ser Phe Ile Asn
                165                 170                 175

Tyr Tyr Asp Ser Glu Lys His Ala Glu Asn Ala Val Ile Phe Leu His
            180                 185                 190

Gly Asn Ala Ala Ser Ser Tyr Leu Trp Arg His Val Val Pro His Ile
        195                 200                 205

Glu Pro Val Ala Arg Cys Ile Ile Pro Asp Leu Ile Gly Met Gly Lys
    210                 215                 220

Ser Gly Lys Ser Gly Asn Gly Ser Tyr Arg Leu Leu Asp His Tyr Lys
225                 230                 235                 240

Tyr Leu Thr Ala Trp Phe Glu Leu Leu Asn Leu Pro Lys Lys Ile Ile
                245                 250                 255

Phe Val Gly His Asp Trp Gly Ala Cys Leu Ala Phe His Tyr Ser Tyr
            260                 265                 270

Glu His Gln Asp Lys Ile Lys Ala Ile Val His Ala Glu Ser Val Val
        275                 280                 285

Asp Val Ile Glu Ser Trp Asp Glu Trp Pro Asp Ile Glu Glu Asp Ile
    290                 295                 300

Ala Leu Ile Lys Ser Glu Glu Gly Glu Lys Met Val Leu Glu Asn Asn
305                 310                 315                 320

Phe Phe Val Glu Thr Met Leu Pro Ser Lys Ile Met Arg Lys Leu Glu
                325                 330                 335

Pro Glu Glu Phe Ala Ala Tyr Leu Glu Pro Phe Lys Glu Lys Gly Glu
            340                 345                 350

Val Arg Arg Pro Thr Leu Ser Trp Pro Arg Glu Ile Pro Leu Val Lys
        355                 360                 365

Gly Gly Lys Pro Asp Val Val Gln Ile Val Arg Asn Tyr Asn Ala Tyr
    370                 375                 380
```

-continued

```
Leu Arg Ala Ser Asp Asp Leu Pro Lys Met Phe Ile Glu Ser Asp Pro
385                 390                 395                 400

Gly Phe Phe Ser Asn Ala Ile Val Glu Gly Ala Lys Lys Phe Pro Asn
                405                 410                 415

Thr Glu Phe Val Lys Val Lys Gly Leu His Phe Ser Gln Glu Asp Ala
            420                 425                 430

Pro Asp Glu Met Gly Lys Tyr Ile Lys Ser Phe Val Glu Arg Val Leu
        435                 440                 445

Lys Asn Glu Gln
    450


<210> SEQ ID NO 7
<211> LENGTH: 1128
<212> TYPE: DNA
<213> ORGANISM: Artificial Sequence
<220> FEATURE:
<223> OTHER INFORMATION: OB RGRP YFP
<220> FEATURE:
<221> NAME/KEY: misc_feature
<223> OTHER INFORMATION: OB RGRP YFP
<220> FEATURE:
<221> NAME/KEY: CDS
<222> LOCATION: (1)..(1128)

<400> SEQUENCE: 7

atg gcg ggc gtt aaa gct ctc gtg gca tta tcc ttc agt ggg gct att       48
Met Ala Gly Val Lys Ala Leu Val Ala Leu Ser Phe Ser Gly Ala Ile
1               5                   10                  15

gga ctg act ttt ctt atg ctg gga tgt gcc tta gag gat tat ggc gtt       96
Gly Leu Thr Phe Leu Met Leu Gly Cys Ala Leu Glu Asp Tyr Gly Val
            20                  25                  30

tac tgg ccc tta ttc gtc ctg att ttc cac gcc atc tcc ccc atc ccc      144
Tyr Trp Pro Leu Phe Val Leu Ile Phe His Ala Ile Ser Pro Ile Pro
        35                  40                  45

cat ttc att gcc aaa aga gtc acc tat gac tca gat gca acc agt agt      192
His Phe Ile Ala Lys Arg Val Thr Tyr Asp Ser Asp Ala Thr Ser Ser
    50                  55                  60

gcc tgt cgg gaa ctg gca tat ttc ttc act act gga att gtt gtt tct      240
Ala Cys Arg Glu Leu Ala Tyr Phe Phe Thr Thr Gly Ile Val Val Ser
65                  70                  75                  80

gcc ttt gga ttt cct gtt att ctt gct cgt gtg gct gtg atc aaa tgg      288
Ala Phe Gly Phe Pro Val Ile Leu Ala Arg Val Ala Val Ile Lys Trp
                85                  90                  95

gga gcc tgc ggc ctt gtg ttg gca ggc aat gca gtc att ttc ctt aca      336
Gly Ala Cys Gly Leu Val Leu Ala Gly Asn Ala Val Ile Phe Leu Thr
            100                 105                 110

att caa ggg ttt ttc ctt ata ttt gga aga gga gat gat ttt agc tgg      384
Ile Gln Gly Phe Phe Leu Ile Phe Gly Arg Gly Asp Asp Phe Ser Trp
        115                 120                 125

gag cag tgg att ccg gtc gcc acc atg gtg agc aag ggc gag gag ctg      432
Glu Gln Trp Ile Pro Val Ala Thr Met Val Ser Lys Gly Glu Glu Leu
    130                 135                 140

ttc acc ggg gtg gtg ccc atc ctg gtc gag ctg gac ggc gac gta aac      480
Phe Thr Gly Val Val Pro Ile Leu Val Glu Leu Asp Gly Asp Val Asn
145                 150                 155                 160

ggc cac aag ttc agc gtg tcc ggc gag ggc gag ggc gat gcc acc tac      528
Gly His Lys Phe Ser Val Ser Gly Glu Gly Glu Gly Asp Ala Thr Tyr
                165                 170                 175

ggc aag ctg acc ctg aag ttc atc tgc acc acc ggc aag ctg ccc gtg      576
Gly Lys Leu Thr Leu Lys Phe Ile Cys Thr Thr Gly Lys Leu Pro Val
            180                 185                 190
```

-continued

```
ccc tgg ccc acc ctc gtg acc acc ttc ggc tac ggc gtg cag tgc ttc      624
Pro Trp Pro Thr Leu Val Thr Thr Phe Gly Tyr Gly Val Gln Cys Phe
        195                 200                 205

gcc cgc tac ccc gac cac atg cgc cag cac gac ttc ttc aag tcc gcc      672
Ala Arg Tyr Pro Asp His Met Arg Gln His Asp Phe Phe Lys Ser Ala
    210                 215                 220

atg ccc gaa ggc tac gtc cag gag cgc acc atc ttc ttc aag gac gac      720
Met Pro Glu Gly Tyr Val Gln Glu Arg Thr Ile Phe Phe Lys Asp Asp
225                 230                 235                 240

ggc aac tac aag acc cgc gcc gag gtg aag ttc gag ggc gac acc ctg      768
Gly Asn Tyr Lys Thr Arg Ala Glu Val Lys Phe Glu Gly Asp Thr Leu
                245                 250                 255

gtg aac cgc atc gag ctg aag ggc atc gac ttc aag gag gac ggc aac      816
Val Asn Arg Ile Glu Leu Lys Gly Ile Asp Phe Lys Glu Asp Gly Asn
            260                 265                 270

atc ctg ggg cac aag ctg gag tac aac tac aac agc cac aac gtc tat      864
Ile Leu Gly His Lys Leu Glu Tyr Asn Tyr Asn Ser His Asn Val Tyr
        275                 280                 285

atc atg gcc gac aag cag aag aac ggc atc aag gtg aac ttc aag atc      912
Ile Met Ala Asp Lys Gln Lys Asn Gly Ile Lys Val Asn Phe Lys Ile
    290                 295                 300

cgc cac aac atc gag gac ggc agc gtg cag ctc gcc gac cac tac cag      960
Arg His Asn Ile Glu Asp Gly Ser Val Gln Leu Ala Asp His Tyr Gln
305                 310                 315                 320

cag aac acc ccc atc ggc gac ggc ccc gtg ctg ctg ccc gac aac cac     1008
Gln Asn Thr Pro Ile Gly Asp Gly Pro Val Leu Leu Pro Asp Asn His
                325                 330                 335

tac ctg agc tac cag tcc gcc ctg agc aaa gac ccc aac gag aag cgc     1056
Tyr Leu Ser Tyr Gln Ser Ala Leu Ser Lys Asp Pro Asn Glu Lys Arg
            340                 345                 350

gat cac atg gtc ctg ctg gag ttc gtg acc gcc gcc ggg atc act ctc     1104
Asp His Met Val Leu Leu Glu Phe Val Thr Ala Ala Gly Ile Thr Leu
        355                 360                 365

ggc atg gac gag ctg tac aag taa                                     1128
Gly Met Asp Glu Leu Tyr Lys
    370                 375


<210> SEQ ID NO 8
<211> LENGTH: 375
<212> TYPE: PRT
<213> ORGANISM: Artificial Sequence
<220> FEATURE:
<223> OTHER INFORMATION: OB RGRP YFP
<220> FEATURE:
<221> NAME/KEY: misc_feature
<223> OTHER INFORMATION: OB RGRP YFP

<400> SEQUENCE: 8

Met Ala Gly Val Lys Ala Leu Val Ala Leu Ser Phe Ser Gly Ala Ile
1               5                   10                  15

Gly Leu Thr Phe Leu Met Leu Gly Cys Ala Leu Glu Asp Tyr Gly Val
            20                  25                  30

Tyr Trp Pro Leu Phe Val Leu Ile Phe His Ala Ile Ser Pro Ile Pro
        35                  40                  45

His Phe Ile Ala Lys Arg Val Thr Tyr Asp Ser Asp Ala Thr Ser Ser
    50                  55                  60

Ala Cys Arg Glu Leu Ala Tyr Phe Phe Thr Thr Gly Ile Val Val Ser
65                  70                  75                  80

Ala Phe Gly Phe Pro Val Ile Leu Ala Arg Val Ala Val Ile Lys Trp
                85                  90                  95
```

-continued

```
Gly Ala Cys Gly Leu Val Leu Ala Gly Asn Ala Val Ile Phe Leu Thr
            100                 105                 110

Ile Gln Gly Phe Phe Leu Ile Phe Gly Arg Gly Asp Asp Phe Ser Trp
        115                 120                 125

Glu Gln Trp Ile Pro Val Ala Thr Met Val Ser Lys Gly Glu Glu Leu
    130                 135                 140

Phe Thr Gly Val Val Pro Ile Leu Val Glu Leu Asp Gly Asp Val Asn
145                 150                 155                 160

Gly His Lys Phe Ser Val Ser Gly Glu Gly Glu Gly Asp Ala Thr Tyr
                165                 170                 175

Gly Lys Leu Thr Leu Lys Phe Ile Cys Thr Thr Gly Lys Leu Pro Val
            180                 185                 190

Pro Trp Pro Thr Leu Val Thr Thr Phe Gly Tyr Gly Val Gln Cys Phe
        195                 200                 205

Ala Arg Tyr Pro Asp His Met Arg Gln His Asp Phe Phe Lys Ser Ala
    210                 215                 220

Met Pro Glu Gly Tyr Val Gln Glu Arg Thr Ile Phe Phe Lys Asp Asp
225                 230                 235                 240

Gly Asn Tyr Lys Thr Arg Ala Glu Val Lys Phe Glu Gly Asp Thr Leu
                245                 250                 255

Val Asn Arg Ile Glu Leu Lys Gly Ile Asp Phe Lys Glu Asp Gly Asn
            260                 265                 270

Ile Leu Gly His Lys Leu Glu Tyr Asn Tyr Asn Ser His Asn Val Tyr
        275                 280                 285

Ile Met Ala Asp Lys Gln Lys Asn Gly Ile Lys Val Asn Phe Lys Ile
    290                 295                 300

Arg His Asn Ile Glu Asp Gly Ser Val Gln Leu Ala Asp His Tyr Gln
305                 310                 315                 320

Gln Asn Thr Pro Ile Gly Asp Gly Pro Val Leu Leu Pro Asp Asn His
                325                 330                 335

Tyr Leu Ser Tyr Gln Ser Ala Leu Ser Lys Asp Pro Asn Glu Lys Arg
            340                 345                 350

Asp His Met Val Leu Leu Glu Phe Val Thr Ala Ala Gly Ile Thr Leu
        355                 360                 365

Gly Met Asp Glu Leu Tyr Lys
    370                 375


<210> SEQ ID NO 9
<211> LENGTH: 2691
<212> TYPE: DNA
<213> ORGANISM: Homo sapiens
<220> FEATURE:
<221> NAME/KEY: CDS
<222> LOCATION: (1)..(2691)

<400> SEQUENCE: 9

atg att tgt caa aaa ttc tgt gtg gtt ttg tta cat tgg gaa ttt att      48
Met Ile Cys Gln Lys Phe Cys Val Val Leu Leu His Trp Glu Phe Ile
1               5                   10                  15

tat gtg ata act gcg ttt aac ttg tca tat cca att act cct tgg aga      96
Tyr Val Ile Thr Ala Phe Asn Leu Ser Tyr Pro Ile Thr Pro Trp Arg
            20                  25                  30

ttt aag ttg tct tgc atg cca cca aat tca acc tat gac tac ttc ctt     144
Phe Lys Leu Ser Cys Met Pro Pro Asn Ser Thr Tyr Asp Tyr Phe Leu
        35                  40                  45

ttg cct gct gga ctc tca aag aat act tca aat tcg aat gga cat tat     192
Leu Pro Ala Gly Leu Ser Lys Asn Thr Ser Asn Ser Asn Gly His Tyr
```

-continued

```
    50                  55                  60

gag aca gct gtt gaa cct aag ttt aat tca agt ggt act cac ttt tct      240
Glu Thr Ala Val Glu Pro Lys Phe Asn Ser Ser Gly Thr His Phe Ser
65                  70                  75                  80

aac tta tcc aaa aca act ttc cac tgt tgc ttt cgg agt gag caa gat      288
Asn Leu Ser Lys Thr Thr Phe His Cys Cys Phe Arg Ser Glu Gln Asp
                85                  90                  95

aga aac tgc tcc tta tgt gca gac aac att gaa gga aag aca ttt gtt      336
Arg Asn Cys Ser Leu Cys Ala Asp Asn Ile Glu Gly Lys Thr Phe Val
            100                 105                 110

tca aca gta aat tct tta gtt ttt caa caa ata gat gca aac tgg aac      384
Ser Thr Val Asn Ser Leu Val Phe Gln Gln Ile Asp Ala Asn Trp Asn
        115                 120                 125

ata cag tgc tgg cta aaa gga gac tta aaa tta ttc atc tgt tat gtg      432
Ile Gln Cys Trp Leu Lys Gly Asp Leu Lys Leu Phe Ile Cys Tyr Val
    130                 135                 140

gag tca tta ttt aag aat cta ttc agg aat tat aac tat aag gtc cat      480
Glu Ser Leu Phe Lys Asn Leu Phe Arg Asn Tyr Asn Tyr Lys Val His
145                 150                 155                 160

ctt tta tat gtt ctg cct gaa gtg tta gaa gat tca cct ctg gtt ccc      528
Leu Leu Tyr Val Leu Pro Glu Val Leu Glu Asp Ser Pro Leu Val Pro
                165                 170                 175

caa aaa ggc agt ttt cag atg gtt cac tgc aat tgc agt gtt cat gaa      576
Gln Lys Gly Ser Phe Gln Met Val His Cys Asn Cys Ser Val His Glu
            180                 185                 190

tgt tgt gaa tgt ctt gtg cct gtg cca aca gcc aaa ctc aac gac act      624
Cys Cys Glu Cys Leu Val Pro Val Pro Thr Ala Lys Leu Asn Asp Thr
        195                 200                 205

ctc ctt atg tgt ttg aaa atc aca tct ggt gga gta att ttc cag tca      672
Leu Leu Met Cys Leu Lys Ile Thr Ser Gly Gly Val Ile Phe Gln Ser
    210                 215                 220

cct cta atg tca gtt cag ccc ata aat atg gtg aag cct gat cca cca      720
Pro Leu Met Ser Val Gln Pro Ile Asn Met Val Lys Pro Asp Pro Pro
225                 230                 235                 240

tta ggt ttg cat atg gaa atc aca gat gat ggt aat tta aag att tct      768
Leu Gly Leu His Met Glu Ile Thr Asp Asp Gly Asn Leu Lys Ile Ser
                245                 250                 255

tgg tcc agc cca cca ttg gta cca ttt cca ctt caa tat caa gtg aaa      816
Trp Ser Ser Pro Pro Leu Val Pro Phe Pro Leu Gln Tyr Gln Val Lys
            260                 265                 270

tat tca gag aat tct aca aca gtt atc aga gaa gct gac aag att gtc      864
Tyr Ser Glu Asn Ser Thr Thr Val Ile Arg Glu Ala Asp Lys Ile Val
        275                 280                 285

tca gct aca tcc ctg cta gta gac agt ata ctt cct ggg tct tcg tat      912
Ser Ala Thr Ser Leu Leu Val Asp Ser Ile Leu Pro Gly Ser Ser Tyr
    290                 295                 300

gag gtt cag gtg agg ggc aag aga ctg gat ggc cca gga atc tgg agt      960
Glu Val Gln Val Arg Gly Lys Arg Leu Asp Gly Pro Gly Ile Trp Ser
305                 310                 315                 320

gac tgg agt act cct cgt gtc ttt acc aca caa gat gtc ata tac ttt     1008
Asp Trp Ser Thr Pro Arg Val Phe Thr Thr Gln Asp Val Ile Tyr Phe
                325                 330                 335

cca cct aaa att ctg aca agt gtt ggg tct aat gtt tct ttt cac tgc     1056
Pro Pro Lys Ile Leu Thr Ser Val Gly Ser Asn Val Ser Phe His Cys
            340                 345                 350

atc tat aag aag gaa aac aag att gtt ccc tca aaa gag att gtt tgg     1104
Ile Tyr Lys Lys Glu Asn Lys Ile Val Pro Ser Lys Glu Ile Val Trp
        355                 360                 365

tgg atg aat tta gct gag aaa att cct caa agc cag tat gat gtt gtg     1152
```

-continued

```
Trp Met Asn Leu Ala Glu Lys Ile Pro Gln Ser Gln Tyr Asp Val Val
    370                 375                 380

agt gat cat gtt agc aaa gtt act ttt ttc aat ctg aat gaa acc aaa      1200
Ser Asp His Val Ser Lys Val Thr Phe Phe Asn Leu Asn Glu Thr Lys
385                 390                 395                 400

cct cga gga aag ttt acc tat gat gca gtg tac tgc tgc aat gaa cat      1248
Pro Arg Gly Lys Phe Thr Tyr Asp Ala Val Tyr Cys Cys Asn Glu His
                405                 410                 415

gaa tgc cat cat cgc tat gct gaa tta tat gtg att gat gtc aat atc      1296
Glu Cys His His Arg Tyr Ala Glu Leu Tyr Val Ile Asp Val Asn Ile
            420                 425                 430

aat atc tca tgt gaa act gat ggg tac tta act aaa atg act tgc aga      1344
Asn Ile Ser Cys Glu Thr Asp Gly Tyr Leu Thr Lys Met Thr Cys Arg
        435                 440                 445

tgg tca acc agt aca atc cag tca ctt gcg gaa agc act ttg caa ttg      1392
Trp Ser Thr Ser Thr Ile Gln Ser Leu Ala Glu Ser Thr Leu Gln Leu
    450                 455                 460

agg tat cat agg agc agc ctt tac tgt tct gat att cca tct att cat      1440
Arg Tyr His Arg Ser Ser Leu Tyr Cys Ser Asp Ile Pro Ser Ile His
465                 470                 475                 480

ccc ata tct gag ccc aaa gat tgc tat ttg cag agt gat ggt ttt tat      1488
Pro Ile Ser Glu Pro Lys Asp Cys Tyr Leu Gln Ser Asp Gly Phe Tyr
                485                 490                 495

gaa tgc att ttc cag cca atc ttc cta tta tct ggc tac aca atg tgg      1536
Glu Cys Ile Phe Gln Pro Ile Phe Leu Leu Ser Gly Tyr Thr Met Trp
            500                 505                 510

att agg atc aat cac tct cta ggt tca ctt gac tct cca cca aca tgt      1584
Ile Arg Ile Asn His Ser Leu Gly Ser Leu Asp Ser Pro Pro Thr Cys
        515                 520                 525

gtc ctt cct gat tct gtg gtg aag cca ctg cct cca tcc agt gtg aaa      1632
Val Leu Pro Asp Ser Val Val Lys Pro Leu Pro Pro Ser Ser Val Lys
    530                 535                 540

gca gaa att act ata aac att gga tta ttg aaa ata tct tgg gaa aag      1680
Ala Glu Ile Thr Ile Asn Ile Gly Leu Leu Lys Ile Ser Trp Glu Lys
545                 550                 555                 560

cca gtc ttt cca gag aat aac ctt caa ttc cag att cgc tat ggt tta      1728
Pro Val Phe Pro Glu Asn Asn Leu Gln Phe Gln Ile Arg Tyr Gly Leu
                565                 570                 575

agt gga aaa gaa gta caa tgg aag atg tat gag gtt tat gat gca aaa      1776
Ser Gly Lys Glu Val Gln Trp Lys Met Tyr Glu Val Tyr Asp Ala Lys
            580                 585                 590

tca aaa tct gtc agt ctc cca gtt cca gac ttg tgt gca gtc tat gct      1824
Ser Lys Ser Val Ser Leu Pro Val Pro Asp Leu Cys Ala Val Tyr Ala
        595                 600                 605

gtt cag gtg cgc tgt aag agg cta gat gga ctg gga tat tgg agt aat      1872
Val Gln Val Arg Cys Lys Arg Leu Asp Gly Leu Gly Tyr Trp Ser Asn
    610                 615                 620

tgg agc aat cca gcc tac aca gtt gtc atg gat ata aaa gtt cct atg      1920
Trp Ser Asn Pro Ala Tyr Thr Val Val Met Asp Ile Lys Val Pro Met
625                 630                 635                 640

aga gga cct gaa ttt tgg aga ata att aat gga gat act atg aaa aag      1968
Arg Gly Pro Glu Phe Trp Arg Ile Ile Asn Gly Asp Thr Met Lys Lys
                645                 650                 655

gag aaa aat gtc act tta ctt tgg aag ccc ctg atg aaa aat gac tca      2016
Glu Lys Asn Val Thr Leu Leu Trp Lys Pro Leu Met Lys Asn Asp Ser
            660                 665                 670

ttg tgc agt gtt cag aga tat gtg ata aac cat cat act tcc tgc aat      2064
Leu Cys Ser Val Gln Arg Tyr Val Ile Asn His His Thr Ser Cys Asn
        675                 680                 685
```

-continued

```
gga aca tgg tca gaa gat gtg gga aat cac acg aaa ttc act ttc ctg      2112
Gly Thr Trp Ser Glu Asp Val Gly Asn His Thr Lys Phe Thr Phe Leu
    690                 695                 700

tgg aca gag caa gca cat act gtt acg gtt ctg gcc atc aat tca att      2160
Trp Thr Glu Gln Ala His Thr Val Thr Val Leu Ala Ile Asn Ser Ile
705                 710                 715                 720

ggt gct tct gtt gca aat ttt aat tta acc ttt tca tgg cct atg agc      2208
Gly Ala Ser Val Ala Asn Phe Asn Leu Thr Phe Ser Trp Pro Met Ser
                725                 730                 735

aaa gta aat atc gtg cag tca ctc agt gct tat cct tta aac agc agt      2256
Lys Val Asn Ile Val Gln Ser Leu Ser Ala Tyr Pro Leu Asn Ser Ser
            740                 745                 750

tgt gtg att gtt tcc tgg ata cta tca ccc agt gat tac aag cta atg      2304
Cys Val Ile Val Ser Trp Ile Leu Ser Pro Ser Asp Tyr Lys Leu Met
        755                 760                 765

tat ttt att att gag tgg aaa aat ctt aat gaa gat ggt gaa ata aaa      2352
Tyr Phe Ile Ile Glu Trp Lys Asn Leu Asn Glu Asp Gly Glu Ile Lys
    770                 775                 780

tgg ctt aga atc tct tca tct gtt aag aag tat tat atc cat gat cat      2400
Trp Leu Arg Ile Ser Ser Ser Val Lys Lys Tyr Tyr Ile His Asp His
785                 790                 795                 800

ttt atc ccc att gag aag tac cag ttc agt ctt tac cca ata ttt atg      2448
Phe Ile Pro Ile Glu Lys Tyr Gln Phe Ser Leu Tyr Pro Ile Phe Met
                805                 810                 815

gaa gga gtg gga aaa cca aag ata att aat agt ttc act caa gat gat      2496
Glu Gly Val Gly Lys Pro Lys Ile Ile Asn Ser Phe Thr Gln Asp Asp
            820                 825                 830

att gaa aaa cac cag agt gat gca ggt tta tat gta att gtg cca gta      2544
Ile Glu Lys His Gln Ser Asp Ala Gly Leu Tyr Val Ile Val Pro Val
        835                 840                 845

att att tcc tct tcc atc tta ttg ctt gga aca tta tta ata tca cac      2592
Ile Ile Ser Ser Ser Ile Leu Leu Leu Gly Thr Leu Leu Ile Ser His
    850                 855                 860

caa aga atg aaa aag cta ttt tgg gaa gat gtt ccg aac ccc aag aat      2640
Gln Arg Met Lys Lys Leu Phe Trp Glu Asp Val Pro Asn Pro Lys Asn
865                 870                 875                 880

tgt tcc tgg gca caa gga ctt aat ttt cag aag aga acg gac att ctt      2688
Cys Ser Trp Ala Gln Gly Leu Asn Phe Gln Lys Arg Thr Asp Ile Leu
                885                 890                 895

tga                                                                  2691
```

<210> SEQ ID NO 10
<211> LENGTH: 896
<212> TYPE: PRT
<213> ORGANISM: Homo sapiens

<400> SEQUENCE: 10

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95
```

-continued

```
Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510
```

-continued

```
Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Arg Thr Asp Ile Leu
                885                 890                 895
```

<210> SEQ ID NO 11
<211> LENGTH: 3705
<212> TYPE: DNA
<213> ORGANISM: Artificial Sequence
<220> FEATURE:
<223> OTHER INFORMATION: OBR LUC -continued

```
<220> FEATURE:
<221> NAME/KEY: misc_feature
<223> OTHER INFORMATION: OBR LUC
<220> FEATURE:
<221> NAME/KEY: CDS
<222> LOCATION: (1)..(3705)

<400> SEQUENCE: 11

atg gtt ctt gcc agc tct acc acc agc atc cac acc atg ctg ctc ctg       48
Met Val Leu Ala Ser Ser Thr Thr Ser Ile His Thr Met Leu Leu Leu
1               5                   10                  15

ctc ctg atg ctc ttc cac ctg gga ctc caa gct tca atc tcg gcg cgc       96
Leu Leu Met Leu Phe His Leu Gly Leu Gln Ala Ser Ile Ser Ala Arg
            20                  25                  30

cag gag cag aag ctt atc tcg gag gag gac ctg acg cgt tat cca att      144
Gln Glu Gln Lys Leu Ile Ser Glu Glu Asp Leu Thr Arg Tyr Pro Ile
        35                  40                  45

act cct tgg aga ttt aag ttg tct tgc atg cca cca aat tca acc tat      192
Thr Pro Trp Arg Phe Lys Leu Ser Cys Met Pro Pro Asn Ser Thr Tyr
    50                  55                  60

gac tac ttc ctt ttg cct gct gga ctc tca aag aat act tca aat tcg      240
Asp Tyr Phe Leu Leu Pro Ala Gly Leu Ser Lys Asn Thr Ser Asn Ser
65                  70                  75                  80

aat gga cat tat gag aca gct gtt gaa cct aag ttt aat tca agt ggt      288
Asn Gly His Tyr Glu Thr Ala Val Glu Pro Lys Phe Asn Ser Ser Gly
                85                  90                  95

act cac ttt tct aac tta tcc aaa aca act ttc cac tgt tgc ttt cgg      336
Thr His Phe Ser Asn Leu Ser Lys Thr Thr Phe His Cys Cys Phe Arg
            100                 105                 110

agt gag caa gat aga aac tgc tcc tta tgt gca gac aac att gaa gga      384
Ser Glu Gln Asp Arg Asn Cys Ser Leu Cys Ala Asp Asn Ile Glu Gly
        115                 120                 125

acg aca ttt gtt tca aca gta aat tct tta gtt ttt caa caa ata gat      432
Thr Thr Phe Val Ser Thr Val Asn Ser Leu Val Phe Gln Gln Ile Asp
    130                 135                 140

gca aac tgg aac ata cag tgc tgg cta aaa gga gac tta aaa tta ttc      480
Ala Asn Trp Asn Ile Gln Cys Trp Leu Lys Gly Asp Leu Lys Leu Phe
145                 150                 155                 160

atc tgt tat gtg gag tca tta ttt aag aat cta ttc agg aat tat aac      528
Ile Cys Tyr Val Glu Ser Leu Phe Lys Asn Leu Phe Arg Asn Tyr Asn
                165                 170                 175

tat aag gtc cat ctt tta tat gtt ctg cct gaa gtg tta gaa gat tca      576
Tyr Lys Val His Leu Leu Tyr Val Leu Pro Glu Val Leu Glu Asp Ser
            180                 185                 190

cct ctg gtt ccc caa aaa ggc agt ttt cag atg gtt cac tgc aat tgc      624
Pro Leu Val Pro Gln Lys Gly Ser Phe Gln Met Val His Cys Asn Cys
        195                 200                 205

agt gtt cat gaa tgt tgt gaa tgt ctt gtg cct gtg cca aca gcc aaa      672
Ser Val His Glu Cys Cys Glu Cys Leu Val Pro Val Pro Thr Ala Lys
    210                 215                 220

ctc aac gac act ctc ctt atg tgt ttg aaa atc aca tct ggt gga gta      720
Leu Asn Asp Thr Leu Leu Met Cys Leu Lys Ile Thr Ser Gly Gly Val
225                 230                 235                 240

att ttc cgg tca cct cta atg tca gtt cag ccc ata aat atg gtg aag      768
Ile Phe Arg Ser Pro Leu Met Ser Val Gln Pro Ile Asn Met Val Lys
                245                 250                 255

cct gat cca cca tta ggt ttg cat atg gaa atc aca gat gat ggt aat      816
Pro Asp Pro Pro Leu Gly Leu His Met Glu Ile Thr Asp Asp Gly Asn
            260                 265                 270

tta aag att tct tgg tcc agc cca cca ttg gta cca ttt cca ctt caa      864
Leu Lys Ile Ser Trp Ser Ser Pro Pro Leu Val Pro Phe Pro Leu Gln
```

-continued

```
        275                 280                 285

tat caa gtg aaa tat tca gag aat tct aca aca gtt atc aga gaa gct      912
Tyr Gln Val Lys Tyr Ser Glu Asn Ser Thr Thr Val Ile Arg Glu Ala
    290                 295                 300

gac aag att gtc tca gct aca tcc ctg cta gta gac agt ata ctt cct      960
Asp Lys Ile Val Ser Ala Thr Ser Leu Leu Val Asp Ser Ile Leu Pro
305                 310                 315                 320

ggg tct tcg tat gag gtt cag gtg agg ggc aag aga ctg gat ggc cca     1008
Gly Ser Ser Tyr Glu Val Gln Val Arg Gly Lys Arg Leu Asp Gly Pro
                325                 330                 335

gga atc tgg agt gac tgg agt act cct cgt gtc ttt acc aca caa gat     1056
Gly Ile Trp Ser Asp Trp Ser Thr Pro Arg Val Phe Thr Thr Gln Asp
            340                 345                 350

gtc ata tac ttt cca cct aaa att ctg aca agt gtt ggg tct aat gtt     1104
Val Ile Tyr Phe Pro Pro Lys Ile Leu Thr Ser Val Gly Ser Asn Val
        355                 360                 365

tct ttt cac tgc atc tat aag aag gaa aac aag att gtt ccc tca aaa     1152
Ser Phe His Cys Ile Tyr Lys Lys Glu Asn Lys Ile Val Pro Ser Lys
    370                 375                 380

gag att gtt tgg tgg atg aat tta gct gag aaa att cct caa agc cag     1200
Glu Ile Val Trp Trp Met Asn Leu Ala Glu Lys Ile Pro Gln Ser Gln
385                 390                 395                 400

tat gat gtt gtg agt gat cat gtt agc aaa gtt act ttt ttc aat ctg     1248
Tyr Asp Val Val Ser Asp His Val Ser Lys Val Thr Phe Phe Asn Leu
                405                 410                 415

aat gaa acc aaa cct cga gga aag ttt acc tat gat gca gtg tac tgc     1296
Asn Glu Thr Lys Pro Arg Gly Lys Phe Thr Tyr Asp Ala Val Tyr Cys
            420                 425                 430

tgc aat gaa cat gaa tgc cat cat cgc tat gct gaa tta tat gtg att     1344
Cys Asn Glu His Glu Cys His His Arg Tyr Ala Glu Leu Tyr Val Ile
        435                 440                 445

gat gtc aat atc aat atc tca tgt gaa act gat ggg tac tta act aaa     1392
Asp Val Asn Ile Asn Ile Ser Cys Glu Thr Asp Gly Tyr Leu Thr Lys
    450                 455                 460

atg act tgc aga tgg tca acc agt aca atc cag tca ctt gcg gaa agc     1440
Met Thr Cys Arg Trp Ser Thr Ser Thr Ile Gln Ser Leu Ala Glu Ser
465                 470                 475                 480

act ttg caa ttg agg tat cat agg agc agc ctt tac tgt tct gat att     1488
Thr Leu Gln Leu Arg Tyr His Arg Ser Ser Leu Tyr Cys Ser Asp Ile
                485                 490                 495

cca tct att cat ccc ata tct gag ccc aaa gat tgc tat ttg cag agt     1536
Pro Ser Ile His Pro Ile Ser Glu Pro Lys Asp Cys Tyr Leu Gln Ser
            500                 505                 510

gat ggt ttt tat gaa tgc att ttc cag cca atc ttc cta tta tct ggc     1584
Asp Gly Phe Tyr Glu Cys Ile Phe Gln Pro Ile Phe Leu Leu Ser Gly
        515                 520                 525

tac aca atg tgg att agg atc aat cac tct cta ggt tca ctt gac tct     1632
Tyr Thr Met Trp Ile Arg Ile Asn His Ser Leu Gly Ser Leu Asp Ser
    530                 535                 540

cca cca aca tgt gtc ctt cct gat tct gtg gtg aag cca ctg cct cca     1680
Pro Pro Thr Cys Val Leu Pro Asp Ser Val Val Lys Pro Leu Pro Pro
545                 550                 555                 560

tcc agt gtg aaa gca gaa att act ata aac att gga tta ttg aaa ata     1728
Ser Ser Val Lys Ala Glu Ile Thr Ile Asn Ile Gly Leu Leu Lys Ile
                565                 570                 575

tct tgg gaa aag cca gtc ttt cca gag aat aac ctt caa ttc cag att     1776
Ser Trp Glu Lys Pro Val Phe Pro Glu Asn Asn Leu Gln Phe Gln Ile
            580                 585                 590

cgc tat ggt tta agt gga aaa gaa gta caa tgg aag atg tat gag gtt     1824
```

-continued

```
Arg Tyr Gly Leu Ser Gly Lys Glu Val Gln Trp Lys Met Tyr Glu Val
        595                 600                 605

tat gat gca aaa tca aaa tct gtc agt ctc cca gtt cca gac ttg tgt      1872
Tyr Asp Ala Lys Ser Lys Ser Val Ser Leu Pro Val Pro Asp Leu Cys
    610                 615                 620

gca gtc tat gct gtt cag gtg cgc tgt aag agg cta gat gga ctg gga      1920
Ala Val Tyr Ala Val Gln Val Arg Cys Lys Arg Leu Asp Gly Leu Gly
625                 630                 635                 640

tat tgg agt aat tgg agc aat cca gcc tac aca gtt gtc atg gat ata      1968
Tyr Trp Ser Asn Trp Ser Asn Pro Ala Tyr Thr Val Val Met Asp Ile
            645                 650                 655

aaa gtt cct atg aga gga cct gaa ttt tgg aga ata att aat gga gat      2016
Lys Val Pro Met Arg Gly Pro Glu Phe Trp Arg Ile Ile Asn Gly Asp
            660                 665                 670

act atg aaa aag gag aaa aat gtc act tta ctt tgg aag ccc ctg atg      2064
Thr Met Lys Lys Glu Lys Asn Val Thr Leu Leu Trp Lys Pro Leu Met
        675                 680                 685

aaa aat gac tca ttg tgc agt gtt cag aga tat gtg ata aac cat cat      2112
Lys Asn Asp Ser Leu Cys Ser Val Gln Arg Tyr Val Ile Asn His His
    690                 695                 700

act tcc tgc aat gga aca tgg tca gaa gat gtg gga aat cac acg aaa      2160
Thr Ser Cys Asn Gly Thr Trp Ser Glu Asp Val Gly Asn His Thr Lys
705                 710                 715                 720

ttc act ttc ctg tgg aca gag caa gca cat act gtt acg gtt ctg gcc      2208
Phe Thr Phe Leu Trp Thr Glu Gln Ala His Thr Val Thr Val Leu Ala
            725                 730                 735

atc aat tca att ggt gct tct gtt gca aat ttt aat tta acc ttt tca      2256
Ile Asn Ser Ile Gly Ala Ser Val Ala Asn Phe Asn Leu Thr Phe Ser
            740                 745                 750

tgg cct atg agc aaa gta aat atc gtg cag tca ctc agt gct tat cct      2304
Trp Pro Met Ser Lys Val Asn Ile Val Gln Ser Leu Ser Ala Tyr Pro
        755                 760                 765

tta aac agc agt tgt gtg att gtt tcc tgg ata cta tca ccc agt gat      2352
Leu Asn Ser Ser Cys Val Ile Val Ser Trp Ile Leu Ser Pro Ser Asp
    770                 775                 780

tac aag cta atg tat ttt att att gag tgg aaa aat ctt aat gaa gat      2400
Tyr Lys Leu Met Tyr Phe Ile Ile Glu Trp Lys Asn Leu Asn Glu Asp
785                 790                 795                 800

ggt gaa ata aaa tgg ctt aga atc tct tca tct gtt aag aag tat tat      2448
Gly Glu Ile Lys Trp Leu Arg Ile Ser Ser Ser Val Lys Lys Tyr Tyr
            805                 810                 815

atc cat gat cat ttt atc ccc att gag aag tac cag ttc agt ctt tac      2496
Ile His Asp His Phe Ile Pro Ile Glu Lys Tyr Gln Phe Ser Leu Tyr
            820                 825                 830

cca ata ttt atg gaa gga gtg gga aaa cca aag ata att aat agt ttc      2544
Pro Ile Phe Met Glu Gly Val Gly Lys Pro Lys Ile Ile Asn Ser Phe
        835                 840                 845

act caa gat gat att gaa aaa cac cag agt gat gca ggt tta tat gta      2592
Thr Gln Asp Asp Ile Glu Lys His Gln Ser Asp Ala Gly Leu Tyr Val
    850                 855                 860

att gtg cca gta att att tcc tct tcc atc tta ttg ctt gga aca tta      2640
Ile Val Pro Val Ile Ile Ser Ser Ser Ile Leu Leu Leu Gly Thr Leu
865                 870                 875                 880

tta ata tca cac caa aga atg aaa aag cta ttt tgg gaa gat gtt ccg      2688
Leu Ile Ser His Gln Arg Met Lys Lys Leu Phe Trp Glu Asp Val Pro
            885                 890                 895

aac ccc aag aat tgt tcc tgg gca caa gga ctt aat ttt cag aag aga      2736
Asn Pro Lys Asn Cys Ser Trp Ala Gln Gly Leu Asn Phe Gln Lys Arg
            900                 905                 910
```

-continued

```
acg gac att ctg gat cca ccg gct aga gcc acc atg acc agc aag gtg      2784
Thr Asp Ile Leu Asp Pro Pro Ala Arg Ala Thr Met Thr Ser Lys Val
        915                 920                 925

tac gac ccc gag cag agg aag agg atg atc acc ggc ccc cag tgg tgg      2832
Tyr Asp Pro Glu Gln Arg Lys Arg Met Ile Thr Gly Pro Gln Trp Trp
    930                 935                 940

gcc agg tgc aag cag atg aac gtg ctg gac agc ttc atc aac tac tac      2880
Ala Arg Cys Lys Gln Met Asn Val Leu Asp Ser Phe Ile Asn Tyr Tyr
945                 950                 955                 960

gac agc gag aag cac gcc gag aac gcc gtg atc ttc ctg cac ggc aac      2928
Asp Ser Glu Lys His Ala Glu Asn Ala Val Ile Phe Leu His Gly Asn
                965                 970                 975

gcc gct agc agc tac ctg tgg agg cac gtg gtg ccc cac atc gag ccc      2976
Ala Ala Ser Ser Tyr Leu Trp Arg His Val Val Pro His Ile Glu Pro
            980                 985                 990

gtg gcc agg tgc atc atc ccc gat  ctg atc ggc atg ggc  aag agc ggc    3024
Val Ala Arg Cys Ile Ile Pro Asp  Leu Ile Gly Met Gly  Lys Ser Gly
        995                 1000                 1005

aag agc  ggc aac ggc agc tac  agg ctg ctg gac cac  tac aag tac      3069
Lys Ser  Gly Asn Gly Ser Tyr  Arg Leu Leu Asp His  Tyr Lys Tyr
    1010                 1015                 1020

ctg acc  gcc tgg ttc gag ctc  ctg aac ctg ccc aag  aag atc atc      3114
Leu Thr  Ala Trp Phe Glu Leu  Leu Asn Leu Pro Lys  Lys Ile Ile
    1025                 1030                 1035

ttc gtg  ggc cac gac tgg ggc  gcc tgc ctg gcc ttc  cac tac agc      3159
Phe Val  Gly His Asp Trp Gly  Ala Cys Leu Ala Phe  His Tyr Ser
    1040                 1045                 1050

tac gag  cac cag gac aag atc  aag gcc atc gtg cac  gcc gag agc      3204
Tyr Glu  His Gln Asp Lys Ile  Lys Ala Ile Val His  Ala Glu Ser
    1055                 1060                 1065

gtg gtg  gac gtg atc gag agc  tgg gac gag tgg cca  gac atc gag      3249
Val Val  Asp Val Ile Glu Ser  Trp Asp Glu Trp Pro  Asp Ile Glu
    1070                 1075                 1080

gag gac  atc gcc ctg atc aag  agc gag gag ggc gag  aag atg gtg      3294
Glu Asp  Ile Ala Leu Ile Lys  Ser Glu Glu Gly Glu  Lys Met Val
    1085                 1090                 1095

ctg gag  aac aac ttc ttc gtg  gag acc atg ctg ccc  agc aag atc      3339
Leu Glu  Asn Asn Phe Phe Val  Glu Thr Met Leu Pro  Ser Lys Ile
    1100                 1105                 1110

atg aga  aag ctg gag ccc gag  gag ttc gcc gcc tac  ctg gag ccc      3384
Met Arg  Lys Leu Glu Pro Glu  Glu Phe Ala Ala Tyr  Leu Glu Pro
    1115                 1120                 1125

ttc aag  gag aag ggc gag gtg  aga aga ccc acc ctg  agc tgg ccc      3429
Phe Lys  Glu Lys Gly Glu Val  Arg Arg Pro Thr Leu  Ser Trp Pro
    1130                 1135                 1140

aga gag  atc ccc ctg gtg aag  ggc ggc aag ccc gac  gtg gtg cag      3474
Arg Glu  Ile Pro Leu Val Lys  Gly Gly Lys Pro Asp  Val Val Gln
    1145                 1150                 1155

atc gtg  aga aac tac aac gcc  tac ctg aga gcc agc  gac gac ctg      3519
Ile Val  Arg Asn Tyr Asn Ala  Tyr Leu Arg Ala Ser  Asp Asp Leu
    1160                 1165                 1170

ccc aag  atg ttc atc gag agc  gac ccc ggc ttc ttc  agc aac gcc      3564
Pro Lys  Met Phe Ile Glu Ser  Asp Pro Gly Phe Phe  Ser Asn Ala
    1175                 1180                 1185

atc gtg  gag ggc gcc aag aag  ttc ccc aac acc gag  ttc gtg aag      3609
Ile Val  Glu Gly Ala Lys Lys  Phe Pro Asn Thr Glu  Phe Val Lys
    1190                 1195                 1200

gtg aag  ggc ctg cac ttc agc  cag gag gac gcc ccc  gac gag atg      3654
Val Lys  Gly Leu His Phe Ser  Gln Glu Asp Ala Pro  Asp Glu Met
    1205                 1210                 1215
```

-continued

```
ggc aag  tac atc aag agc ttc  gtg gag aga gtg ctg  aag aac gag      3699
Gly Lys  Tyr Ile Lys Ser Phe  Val Glu Arg Val Leu  Lys Asn Glu
    1220                1225                1230

cag taa                                                             3705
Gln


<210> SEQ ID NO 12
<211> LENGTH: 1234
<212> TYPE: PRT
<213> ORGANISM: Artificial Sequence
<220> FEATURE:
<223> OTHER INFORMATION: OBR LUC
<220> FEATURE:
<221> NAME/KEY: misc_feature
<223> OTHER INFORMATION: OBR LUC

<400> SEQUENCE: 12

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Glu Gln Lys Leu Ile Ser Glu Glu Asp Leu Thr Arg Tyr Pro Ile
        35                  40                  45

Thr Pro Trp Arg Phe Lys Leu Ser Cys Met Pro Pro Asn Ser Thr Tyr
    50                  55                  60

Asp Tyr Phe Leu Leu Pro Ala Gly Leu Ser Lys Asn Thr Ser Asn Ser
65                  70                  75                  80

Asn Gly His Tyr Glu Thr Ala Val Glu Pro Lys Phe Asn Ser Ser Gly
                85                  90                  95

Thr His Phe Ser Asn Leu Ser Lys Thr Thr Phe His Cys Cys Phe Arg
            100                 105                 110

Ser Glu Gln Asp Arg Asn Cys Ser Leu Cys Ala Asp Asn Ile Glu Gly
        115                 120                 125

Thr Thr Phe Val Ser Thr Val Asn Ser Leu Val Phe Gln Gln Ile Asp
    130                 135                 140

Ala Asn Trp Asn Ile Gln Cys Trp Leu Lys Gly Asp Leu Lys Leu Phe
145                 150                 155                 160

Ile Cys Tyr Val Glu Ser Leu Phe Lys Asn Leu Phe Arg Asn Tyr Asn
                165                 170                 175

Tyr Lys Val His Leu Leu Tyr Val Leu Pro Glu Val Leu Glu Asp Ser
            180                 185                 190

Pro Leu Val Pro Gln Lys Gly Ser Phe Gln Met Val His Cys Asn Cys
        195                 200                 205

Ser Val His Glu Cys Cys Glu Cys Leu Val Pro Val Pro Thr Ala Lys
    210                 215                 220

Leu Asn Asp Thr Leu Leu Met Cys Leu Lys Ile Thr Ser Gly Gly Val
225                 230                 235                 240

Ile Phe Arg Ser Pro Leu Met Ser Val Gln Pro Ile Asn Met Val Lys
                245                 250                 255

Pro Asp Pro Pro Leu Gly Leu His Met Glu Ile Thr Asp Asp Gly Asn
            260                 265                 270

Leu Lys Ile Ser Trp Ser Ser Pro Pro Leu Val Pro Phe Pro Leu Gln
        275                 280                 285

Tyr Gln Val Lys Tyr Ser Glu Asn Ser Thr Thr Val Ile Arg Glu Ala
    290                 295                 300

Asp Lys Ile Val Ser Ala Thr Ser Leu Leu Val Asp Ser Ile Leu Pro
```

-continued 305 310 315 320

Gly Ser Ser Tyr Glu Val Gln Val Arg Gly Lys Arg Leu Asp Gly Pro
325 330 335

Gly Ile Trp Ser Asp Trp Ser Thr Pro Arg Val Phe Thr Thr Gln Asp
340 345 350

Val Ile Tyr Phe Pro Pro Lys Ile Leu Thr Ser Val Gly Ser Asn Val
355 360 365

Ser Phe His Cys Ile Tyr Lys Lys Glu Asn Lys Ile Val Pro Ser Lys
370 375 380

Glu Ile Val Trp Trp Met Asn Leu Ala Glu Lys Ile Pro Gln Ser Gln
385 390 395 400

Tyr Asp Val Val Ser Asp His Val Ser Lys Val Thr Phe Phe Asn Leu
405 410 415

Asn Glu Thr Lys Pro Arg Gly Lys Phe Thr Tyr Asp Ala Val Tyr Cys
420 425 430

Cys Asn Glu His Glu Cys His His Arg Tyr Ala Glu Leu Tyr Val Ile
435 440 445

Asp Val Asn Ile Asn Ile Ser Cys Glu Thr Asp Gly Tyr Leu Thr Lys
450 455 460

Met Thr Cys Arg Trp Ser Thr Ser Thr Ile Gln Ser Leu Ala Glu Ser
465 470 475 480

Thr Leu Gln Leu Arg Tyr His Arg Ser Ser Leu Tyr Cys Ser Asp Ile
485 490 495

Pro Ser Ile His Pro Ile Ser Glu Pro Lys Asp Cys Tyr Leu Gln Ser
500 505 510

Asp Gly Phe Tyr Glu Cys Ile Phe Gln Pro Ile Phe Leu Leu Ser Gly
515 520 525

Tyr Thr Met Trp Ile Arg Ile Asn His Ser Leu Gly Ser Leu Asp Ser
530 535 540

Pro Pro Thr Cys Val Leu Pro Asp Ser Val Val Lys Pro Leu Pro Pro
545 550 555 560

Ser Ser Val Lys Ala Glu Ile Thr Ile Asn Ile Gly Leu Leu Lys Ile
565 570 575

Ser Trp Glu Lys Pro Val Phe Pro Glu Asn Asn Leu Gln Phe Gln Ile
580 585 590

Arg Tyr Gly Leu Ser Gly Lys Glu Val Gln Trp Lys Met Tyr Glu Val
595 600 605

Tyr Asp Ala Lys Ser Lys Ser Val Ser Leu Pro Val Pro Asp Leu Cys
610 615 620

Ala Val Tyr Ala Val Gln Val Arg Cys Lys Arg Leu Asp Gly Leu Gly
625 630 635 640

Tyr Trp Ser Asn Trp Ser Asn Pro Ala Tyr Thr Val Val Met Asp Ile
645 650 655

Lys Val Pro Met Arg Gly Pro Glu Phe Trp Arg Ile Ile Asn Gly Asp
660 665 670

Thr Met Lys Lys Glu Lys Asn Val Thr Leu Leu Trp Lys Pro Leu Met
675 680 685

Lys Asn Asp Ser Leu Cys Ser Val Gln Arg Tyr Val Ile Asn His His
690 695 700

Thr Ser Cys Asn Gly Thr Trp Ser Glu Asp Val Gly Asn His Thr Lys
705 710 715 720

Phe Thr Phe Leu Trp Thr Glu Gln Ala His Thr Val Thr Val Leu Ala
725 730 735

-continued

```
Ile Asn Ser Ile Gly Ala Ser Val Ala Asn Phe Asn Leu Thr Phe Ser
            740                 745                 750

Trp Pro Met Ser Lys Val Asn Ile Val Gln Ser Leu Ser Ala Tyr Pro
        755                 760                 765

Leu Asn Ser Ser Cys Val Ile Val Ser Trp Ile Leu Ser Pro Ser Asp
    770                 775                 780

Tyr Lys Leu Met Tyr Phe Ile Ile Glu Trp Lys Asn Leu Asn Glu Asp
785                 790                 795                 800

Gly Glu Ile Lys Trp Leu Arg Ile Ser Ser Ser Val Lys Lys Tyr Tyr
                805                 810                 815

Ile His Asp His Phe Ile Pro Ile Glu Lys Tyr Gln Phe Ser Leu Tyr
            820                 825                 830

Pro Ile Phe Met Glu Gly Val Gly Lys Pro Lys Ile Ile Asn Ser Phe
        835                 840                 845

Thr Gln Asp Asp Ile Glu Lys His Gln Ser Asp Ala Gly Leu Tyr Val
    850                 855                 860

Ile Val Pro Val Ile Ile Ser Ser Ser Ile Leu Leu Leu Gly Thr Leu
865                 870                 875                 880

Leu Ile Ser His Gln Arg Met Lys Lys Leu Phe Trp Glu Asp Val Pro
                885                 890                 895

Asn Pro Lys Asn Cys Ser Trp Ala Gln Gly Leu Asn Phe Gln Lys Arg
            900                 905                 910

Thr Asp Ile Leu Asp Pro Pro Ala Arg Ala Thr Met Thr Ser Lys Val
        915                 920                 925

Tyr Asp Pro Glu Gln Arg Lys Arg Met Ile Thr Gly Pro Gln Trp Trp
    930                 935                 940

Ala Arg Cys Lys Gln Met Asn Val Leu Asp Ser Phe Ile Asn Tyr Tyr
945                 950                 955                 960

Asp Ser Glu Lys His Ala Glu Asn Ala Val Ile Phe Leu His Gly Asn
                965                 970                 975

Ala Ala Ser Ser Tyr Leu Trp Arg His Val Val Pro His Ile Glu Pro
            980                 985                 990

Val Ala Arg Cys Ile Ile Pro Asp  Leu Ile Gly Met Gly  Lys Ser Gly
        995                 1000                1005

Lys Ser  Gly Asn Gly Ser Tyr  Arg Leu Leu Asp His  Tyr Lys Tyr
    1010                1015                1020

Leu Thr  Ala Trp Phe Glu Leu  Leu Asn Leu Pro Lys  Lys Ile Ile
    1025                1030                1035

Phe Val  Gly His Asp Trp Gly  Ala Cys Leu Ala Phe  His Tyr Ser
    1040                1045                1050

Tyr Glu  His Gln Asp Lys Ile  Lys Ala Ile Val His  Ala Glu Ser
    1055                1060                1065

Val Val  Asp Val Ile Glu Ser  Trp Asp Glu Trp Pro  Asp Ile Glu
    1070                1075                1080

Glu Asp  Ile Ala Leu Ile Lys  Ser Glu Glu Gly Glu  Lys Met Val
    1085                1090                1095

Leu Glu  Asn Asn Phe Phe Val  Glu Thr Met Leu Pro  Ser Lys Ile
    1100                1105                1110

Met Arg  Lys Leu Glu Pro Glu  Glu Phe Ala Ala Tyr  Leu Glu Pro
    1115                1120                1125

Phe Lys  Glu Lys Gly Glu Val  Arg Arg Pro Thr Leu  Ser Trp Pro
    1130                1135                1140
```

-continued

```
Arg Glu  Ile Pro Leu Val Lys  Gly Gly Lys Pro Asp  Val Val Gln
    1145                 1150                 1155

Ile Val  Arg Asn Tyr Asn Ala  Tyr Leu Arg Ala Ser  Asp Asp Leu
    1160                 1165                 1170

Pro Lys  Met Phe Ile Glu Ser  Asp Pro Gly Phe Phe  Ser Asn Ala
    1175                 1180                 1185

Ile Val  Glu Gly Ala Lys Lys  Phe Pro Asn Thr Glu  Phe Val Lys
    1190                 1195                 1200

Val Lys  Gly Leu His Phe Ser  Gln Glu Asp Ala Pro  Asp Glu Met
    1205                 1210                 1215

Gly Lys  Tyr Ile Lys Ser Phe  Val Glu Arg Val Leu  Lys Asn Glu
    1220                 1225                 1230

Gln


<210> SEQ ID NO 13
<211> LENGTH: 3486
<212> TYPE: DNA
<213> ORGANISM: Artificial Sequence
<220> FEATURE:
<223> OTHER INFORMATION: OBR YFP
<220> FEATURE:
<221> NAME/KEY: misc_feature
<223> OTHER INFORMATION: OBR YFP
<220> FEATURE:
<221> NAME/KEY: CDS
<222> LOCATION: (1)..(3486)

<400> SEQUENCE: 13

atg gtt ctt gcc agc tct acc acc agc atc cac acc atg ctg ctc ctg       48
Met Val Leu Ala Ser Ser Thr Thr Ser Ile His Thr Met Leu Leu Leu
1               5                   10                  15

ctc ctg atg ctc ttc cac ctg gga ctc caa gct tca atc tcg gcg cgc       96
Leu Leu Met Leu Phe His Leu Gly Leu Gln Ala Ser Ile Ser Ala Arg
            20                  25                  30

cag gag cag aag ctt atc tcg gag gag gac ctg acg cgt tat cca att      144
Gln Glu Gln Lys Leu Ile Ser Glu Glu Asp Leu Thr Arg Tyr Pro Ile
        35                  40                  45

act cct tgg aga ttt aag ttg tct tgc atg cca cca aat tca acc tat      192
Thr Pro Trp Arg Phe Lys Leu Ser Cys Met Pro Pro Asn Ser Thr Tyr
    50                  55                  60

gac tac ttc ctt ttg cct gct gga ctc tca aag aat act tca aat tcg      240
Asp Tyr Phe Leu Leu Pro Ala Gly Leu Ser Lys Asn Thr Ser Asn Ser
65                  70                  75                  80

aat gga cat tat gag aca gct gtt gaa cct aag ttt aat tca agt ggt      288
Asn Gly His Tyr Glu Thr Ala Val Glu Pro Lys Phe Asn Ser Ser Gly
                85                  90                  95

act cac ttt tct aac tta tcc aaa aca act ttc cac tgt tgc ttt cgg      336
Thr His Phe Ser Asn Leu Ser Lys Thr Thr Phe His Cys Cys Phe Arg
            100                 105                 110

agt gag caa gat aga aac tgc tcc tta tgt gca gac aac att gaa gga      384
Ser Glu Gln Asp Arg Asn Cys Ser Leu Cys Ala Asp Asn Ile Glu Gly
        115                 120                 125

acg aca ttt gtt tca aca gta aat tct tta gtt ttt caa caa ata gat      432
Thr Thr Phe Val Ser Thr Val Asn Ser Leu Val Phe Gln Gln Ile Asp
    130                 135                 140

gca aac tgg aac ata cag tgc tgg cta aaa gga gac tta aaa tta ttc      480
Ala Asn Trp Asn Ile Gln Cys Trp Leu Lys Gly Asp Leu Lys Leu Phe
145                 150                 155                 160

atc tgt tat gtg gag tca tta ttt aag aat cta ttc agg aat tat aac      528
Ile Cys Tyr Val Glu Ser Leu Phe Lys Asn Leu Phe Arg Asn Tyr Asn
                165                 170                 175
```

-continued

```
tat aag gtc cat ctt tta tat gtt ctg cct gaa gtg tta gaa gat tca      576
Tyr Lys Val His Leu Leu Tyr Val Leu Pro Glu Val Leu Glu Asp Ser
            180                 185                 190

cct ctg gtt ccc caa aaa ggc agt ttt cag atg gtt cac tgc aat tgc      624
Pro Leu Val Pro Gln Lys Gly Ser Phe Gln Met Val His Cys Asn Cys
        195                 200                 205

agt gtt cat gaa tgt tgt gaa tgt ctt gtg cct gtg cca aca gcc aaa      672
Ser Val His Glu Cys Cys Glu Cys Leu Val Pro Val Pro Thr Ala Lys
    210                 215                 220

ctc aac gac act ctc ctt atg tgt ttg aaa atc aca tct ggt gga gta      720
Leu Asn Asp Thr Leu Leu Met Cys Leu Lys Ile Thr Ser Gly Gly Val
225                 230                 235                 240

att ttc cgg tca cct cta atg tca gtt cag ccc ata aat atg gtg aag      768
Ile Phe Arg Ser Pro Leu Met Ser Val Gln Pro Ile Asn Met Val Lys
                245                 250                 255

cct gat cca cca tta ggt ttg cat atg gaa atc aca gat gat ggt aat      816
Pro Asp Pro Pro Leu Gly Leu His Met Glu Ile Thr Asp Asp Gly Asn
            260                 265                 270

tta aag att tct tgg tcc agc cca cca ttg gta cca ttt cca ctt caa      864
Leu Lys Ile Ser Trp Ser Ser Pro Pro Leu Val Pro Phe Pro Leu Gln
        275                 280                 285

tat caa gtg aaa tat tca gag aat tct aca aca gtt atc aga gaa gct      912
Tyr Gln Val Lys Tyr Ser Glu Asn Ser Thr Thr Val Ile Arg Glu Ala
    290                 295                 300

gac aag att gtc tca gct aca tcc ctg cta gta gac agt ata ctt cct      960
Asp Lys Ile Val Ser Ala Thr Ser Leu Leu Val Asp Ser Ile Leu Pro
305                 310                 315                 320

ggg tct tcg tat gag gtt cag gtg agg ggc aag aga ctg gat ggc cca     1008
Gly Ser Ser Tyr Glu Val Gln Val Arg Gly Lys Arg Leu Asp Gly Pro
                325                 330                 335

gga atc tgg agt gac tgg agt act cct cgt gtc ttt acc aca caa gat     1056
Gly Ile Trp Ser Asp Trp Ser Thr Pro Arg Val Phe Thr Thr Gln Asp
            340                 345                 350

gtc ata tac ttt cca cct aaa att ctg aca agt gtt ggg tct aat gtt     1104
Val Ile Tyr Phe Pro Pro Lys Ile Leu Thr Ser Val Gly Ser Asn Val
        355                 360                 365

tct ttt cac tgc atc tat aag aag gaa aac aag att gtt ccc tca aaa     1152
Ser Phe His Cys Ile Tyr Lys Lys Glu Asn Lys Ile Val Pro Ser Lys
    370                 375                 380

gag att gtt tgg tgg atg aat tta gct gag aaa att cct caa agc cag     1200
Glu Ile Val Trp Trp Met Asn Leu Ala Glu Lys Ile Pro Gln Ser Gln
385                 390                 395                 400

tat gat gtt gtg agt gat cat gtt agc aaa gtt act ttt ttc aat ctg     1248
Tyr Asp Val Val Ser Asp His Val Ser Lys Val Thr Phe Phe Asn Leu
                405                 410                 415

aat gaa acc aaa cct cga gga aag ttt acc tat gat gca gtg tac tgc     1296
Asn Glu Thr Lys Pro Arg Gly Lys Phe Thr Tyr Asp Ala Val Tyr Cys
            420                 425                 430

tgc aat gaa cat gaa tgc cat cat cgc tat gct gaa tta tat gtg att     1344
Cys Asn Glu His Glu Cys His His Arg Tyr Ala Glu Leu Tyr Val Ile
        435                 440                 445

gat gtc aat atc aat atc tca tgt gaa act gat ggg tac tta act aaa     1392
Asp Val Asn Ile Asn Ile Ser Cys Glu Thr Asp Gly Tyr Leu Thr Lys
    450                 455                 460

atg act tgc aga tgg tca acc agt aca atc cag tca ctt gcg gaa agc     1440
Met Thr Cys Arg Trp Ser Thr Ser Thr Ile Gln Ser Leu Ala Glu Ser
465                 470                 475                 480

act ttg caa ttg agg tat cat agg agc agc ctt tac tgt tct gat att     1488
Thr Leu Gln Leu Arg Tyr His Arg Ser Ser Leu Tyr Cys Ser Asp Ile
```

-continued

```
                485                 490                 495

cca tct att cat ccc ata tct gag ccc aaa gat tgc tat ttg cag agt     1536
Pro Ser Ile His Pro Ile Ser Glu Pro Lys Asp Cys Tyr Leu Gln Ser
            500                 505                 510

gat ggt ttt tat gaa tgc att ttc cag cca atc ttc cta tta tct ggc     1584
Asp Gly Phe Tyr Glu Cys Ile Phe Gln Pro Ile Phe Leu Leu Ser Gly
        515                 520                 525

tac aca atg tgg att agg atc aat cac tct cta ggt tca ctt gac tct     1632
Tyr Thr Met Trp Ile Arg Ile Asn His Ser Leu Gly Ser Leu Asp Ser
    530                 535                 540

cca cca aca tgt gtc ctt cct gat tct gtg gtg aag cca ctg cct cca     1680
Pro Pro Thr Cys Val Leu Pro Asp Ser Val Val Lys Pro Leu Pro Pro
545                 550                 555                 560

tcc agt gtg aaa gca gaa att act ata aac att gga tta ttg aaa ata     1728
Ser Ser Val Lys Ala Glu Ile Thr Ile Asn Ile Gly Leu Leu Lys Ile
                565                 570                 575

tct tgg gaa aag cca gtc ttt cca gag aat aac ctt caa ttc cag att     1776
Ser Trp Glu Lys Pro Val Phe Pro Glu Asn Asn Leu Gln Phe Gln Ile
            580                 585                 590

cgc tat ggt tta agt gga aaa gaa gta caa tgg aag atg tat gag gtt     1824
Arg Tyr Gly Leu Ser Gly Lys Glu Val Gln Trp Lys Met Tyr Glu Val
        595                 600                 605

tat gat gca aaa tca aaa tct gtc agt ctc cca gtt cca gac ttg tgt     1872
Tyr Asp Ala Lys Ser Lys Ser Val Ser Leu Pro Val Pro Asp Leu Cys
    610                 615                 620

gca gtc tat gct gtt cag gtg cgc tgt aag agg cta gat gga ctg gga     1920
Ala Val Tyr Ala Val Gln Val Arg Cys Lys Arg Leu Asp Gly Leu Gly
625                 630                 635                 640

tat tgg agt aat tgg agc aat cca gcc tac aca gtt gtc atg gat ata     1968
Tyr Trp Ser Asn Trp Ser Asn Pro Ala Tyr Thr Val Val Met Asp Ile
                645                 650                 655

aaa gtt cct atg aga gga cct gaa ttt tgg aga ata att aat gga gat     2016
Lys Val Pro Met Arg Gly Pro Glu Phe Trp Arg Ile Ile Asn Gly Asp
            660                 665                 670

act atg aaa aag gag aaa aat gtc act tta ctt tgg aag ccc ctg atg     2064
Thr Met Lys Lys Glu Lys Asn Val Thr Leu Leu Trp Lys Pro Leu Met
        675                 680                 685

aaa aat gac tca ttg tgc agt gtt cag aga tat gtg ata aac cat cat     2112
Lys Asn Asp Ser Leu Cys Ser Val Gln Arg Tyr Val Ile Asn His His
    690                 695                 700

act tcc tgc aat gga aca tgg tca gaa gat gtg gga aat cac acg aaa     2160
Thr Ser Cys Asn Gly Thr Trp Ser Glu Asp Val Gly Asn His Thr Lys
705                 710                 715                 720

ttc act ttc ctg tgg aca gag caa gca cat act gtt acg gtt ctg gcc     2208
Phe Thr Phe Leu Trp Thr Glu Gln Ala His Thr Val Thr Val Leu Ala
                725                 730                 735

atc aat tca att ggt gct tct gtt gca aat ttt aat tta acc ttt tca     2256
Ile Asn Ser Ile Gly Ala Ser Val Ala Asn Phe Asn Leu Thr Phe Ser
            740                 745                 750

tgg cct atg agc aaa gta aat atc gtg cag tca ctc agt gct tat cct     2304
Trp Pro Met Ser Lys Val Asn Ile Val Gln Ser Leu Ser Ala Tyr Pro
        755                 760                 765

tta aac agc agt tgt gtg att gtt tcc tgg ata cta tca ccc agt gat     2352
Leu Asn Ser Ser Cys Val Ile Val Ser Trp Ile Leu Ser Pro Ser Asp
    770                 775                 780

tac aag cta atg tat ttt att att gag tgg aaa aat ctt aat gaa gat     2400
Tyr Lys Leu Met Tyr Phe Ile Ile Glu Trp Lys Asn Leu Asn Glu Asp
785                 790                 795                 800

ggt gaa ata aaa tgg ctt aga atc tct tca tct gtt aag aag tat tat     2448
```

-continued

```
Gly Glu Ile Lys Trp Leu Arg Ile Ser Ser Ser Val Lys Lys Tyr Tyr
                805                 810                 815

atc cat gat cat ttt atc ccc att gag aag tac cag ttc agt ctt tac      2496
Ile His Asp His Phe Ile Pro Ile Glu Lys Tyr Gln Phe Ser Leu Tyr
            820                 825                 830

cca ata ttt atg gaa gga gtg gga aaa cca aag ata att aat agt ttc      2544
Pro Ile Phe Met Glu Gly Val Gly Lys Pro Lys Ile Ile Asn Ser Phe
        835                 840                 845

act caa gat gat att gaa aaa cac cag agt gat gca ggt tta tat gta      2592
Thr Gln Asp Asp Ile Glu Lys His Gln Ser Asp Ala Gly Leu Tyr Val
    850                 855                 860

att gtg cca gta att att tcc tct tcc atc tta ttg ctt gga aca tta      2640
Ile Val Pro Val Ile Ile Ser Ser Ser Ile Leu Leu Leu Gly Thr Leu
865                 870                 875                 880

tta ata tca cac caa aga atg aaa aag cta ttt tgg gaa gat gtt ccg      2688
Leu Ile Ser His Gln Arg Met Lys Lys Leu Phe Trp Glu Asp Val Pro
                885                 890                 895

aac ccc aag aat tgt tcc tgg gca caa gga ctt aat ttt cag aag aga      2736
Asn Pro Lys Asn Cys Ser Trp Ala Gln Gly Leu Asn Phe Gln Lys Arg
            900                 905                 910

acg gac att ctg gat cca ccg gtc gcc acc atg gtg agc aag ggc gag      2784
Thr Asp Ile Leu Asp Pro Pro Val Ala Thr Met Val Ser Lys Gly Glu
        915                 920                 925

gag ctg ttc acc ggg gtg gtg ccc atc ctg gtc gag ctg gac ggc gac      2832
Glu Leu Phe Thr Gly Val Val Pro Ile Leu Val Glu Leu Asp Gly Asp
    930                 935                 940

gta aac ggc cac aag ttc agc gtg tcc ggc gag ggc gag ggc gat gcc      2880
Val Asn Gly His Lys Phe Ser Val Ser Gly Glu Gly Glu Gly Asp Ala
945                 950                 955                 960

acc tac ggc aag ctg acc ctg aag ttc atc tgc acc acc ggc aag ctg      2928
Thr Tyr Gly Lys Leu Thr Leu Lys Phe Ile Cys Thr Thr Gly Lys Leu
                965                 970                 975

ccc gtg ccc tgg ccc acc ctc gtg acc acc ttc ggc tac ggc gtg cag      2976
Pro Val Pro Trp Pro Thr Leu Val Thr Thr Phe Gly Tyr Gly Val Gln
            980                 985                 990

tgc ttc gcc cgc tac ccc gac cac  atg cgc cag cac gac  ttc ttc aag    3024
Cys Phe Ala Arg Tyr Pro Asp His  Met Arg Gln His Asp  Phe Phe Lys
        995                 1000                1005

tcc gcc  atg ccc gaa ggc tac  gtc cag gag cgc acc  atc ttc ttc      3069
Ser Ala  Met Pro Glu Gly Tyr  Val Gln Glu Arg Thr  Ile Phe Phe
    1010                1015                1020

aag gac  gac ggc aac tac aag  acc cgc gcc gag gtg  aag ttc gag      3114
Lys Asp  Asp Gly Asn Tyr Lys  Thr Arg Ala Glu Val  Lys Phe Glu
    1025                1030                1035

ggc gac  acc ctg gtg aac cgc  atc gag ctg aag ggc  atc gac ttc      3159
Gly Asp  Thr Leu Val Asn Arg  Ile Glu Leu Lys Gly  Ile Asp Phe
    1040                1045                1050

aag gag  gac ggc aac atc ctg  ggg cac aag ctg gag  tac aac tac      3204
Lys Glu  Asp Gly Asn Ile Leu  Gly His Lys Leu Glu  Tyr Asn Tyr
    1055                1060                1065

aac agc  cac aac gtc tat atc  atg gcc gac aag cag  aag aac ggc      3249
Asn Ser  His Asn Val Tyr Ile  Met Ala Asp Lys Gln  Lys Asn Gly
    1070                1075                1080

atc aag  gtg aac ttc aag atc  cgc cac aac atc gag  gac ggc agc      3294
Ile Lys  Val Asn Phe Lys Ile  Arg His Asn Ile Glu  Asp Gly Ser
    1085                1090                1095

gtg cag  ctc gcc gac cac tac  cag cag aac acc ccc  atc ggc gac      3339
Val Gln  Leu Ala Asp His Tyr  Gln Gln Asn Thr Pro  Ile Gly Asp
    1100                1105                1110
```

-continued

```
ggc ccc  gtg ctg ctg ccc gac  aac cac tac ctg agc  tac cag tcc      3384
Gly Pro  Val Leu Leu Pro Asp  Asn His Tyr Leu Ser  Tyr Gln Ser
    1115                 1120                 1125

gcc ctg  agc aaa gac ccc aac  gag aag cgc gat cac  atg gtc ctg      3429
Ala Leu  Ser Lys Asp Pro Asn  Glu Lys Arg Asp His  Met Val Leu
    1130                 1135                 1140

ctg gag  ttc gtg acc gcc gcc  ggg atc act ctc ggc  atg gac gag      3474
Leu Glu  Phe Val Thr Ala Ala  Gly Ile Thr Leu Gly  Met Asp Glu
    1145                 1150                 1155

ctg tac  aag taa                                                   3486
Leu Tyr  Lys
    1160
```

<210> SEQ ID NO 14
<211> LENGTH: 1161
<212> TYPE: PRT
<213> ORGANISM: Artificial Sequence
<220> FEATURE:
<223> OTHER INFORMATION: OBR YFP
<220> FEATURE:
<221> NAME/KEY: misc_feature
<223> OTHER INFORMATION: OBR YFP

<400> SEQUENCE: 14

```
Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Glu Gln Lys Leu Ile Ser Glu Glu Asp Leu Thr Arg Tyr Pro Ile
        35                  40                  45

Thr Pro Trp Arg Phe Lys Leu Ser Cys Met Pro Pro Asn Ser Thr Tyr
    50                  55                  60

Asp Tyr Phe Leu Leu Pro Ala Gly Leu Ser Lys Asn Thr Ser Asn Ser
65                  70                  75                  80

Asn Gly His Tyr Glu Thr Ala Val Glu Pro Lys Phe Asn Ser Ser Gly
                85                  90                  95

Thr His Phe Ser Asn Leu Ser Lys Thr Thr Phe His Cys Cys Phe Arg
            100                 105                 110

Ser Glu Gln Asp Arg Asn Cys Ser Leu Cys Ala Asp Asn Ile Glu Gly
        115                 120                 125

Thr Thr Phe Val Ser Thr Val Asn Ser Leu Val Phe Gln Gln Ile Asp
    130                 135                 140

Ala Asn Trp Asn Ile Gln Cys Trp Leu Lys Gly Asp Leu Lys Leu Phe
145                 150                 155                 160

Ile Cys Tyr Val Glu Ser Leu Phe Lys Asn Leu Phe Arg Asn Tyr Asn
                165                 170                 175

Tyr Lys Val His Leu Leu Tyr Val Leu Pro Glu Val Leu Glu Asp Ser
            180                 185                 190

Pro Leu Val Pro Gln Lys Gly Ser Phe Gln Met Val His Cys Asn Cys
        195                 200                 205

Ser Val His Glu Cys Cys Glu Cys Leu Val Pro Val Pro Thr Ala Lys
    210                 215                 220

Leu Asn Asp Thr Leu Leu Met Cys Leu Lys Ile Thr Ser Gly Gly Val
225                 230                 235                 240

Ile Phe Arg Ser Pro Leu Met Ser Val Gln Pro Ile Asn Met Val Lys
                245                 250                 255

Pro Asp Pro Pro Leu Gly Leu His Met Glu Ile Thr Asp Asp Gly Asn
            260                 265                 270
```

-continued

```
Leu Lys Ile Ser Trp Ser Ser Pro Pro Leu Val Pro Phe Pro Leu Gln
        275                 280                 285

Tyr Gln Val Lys Tyr Ser Glu Asn Ser Thr Thr Val Ile Arg Glu Ala
    290                 295                 300

Asp Lys Ile Val Ser Ala Thr Ser Leu Leu Val Asp Ser Ile Leu Pro
305                 310                 315                 320

Gly Ser Ser Tyr Glu Val Gln Val Arg Gly Lys Arg Leu Asp Gly Pro
                325                 330                 335

Gly Ile Trp Ser Asp Trp Ser Thr Pro Arg Val Phe Thr Thr Gln Asp
            340                 345                 350

Val Ile Tyr Phe Pro Pro Lys Ile Leu Thr Ser Val Gly Ser Asn Val
        355                 360                 365

Ser Phe His Cys Ile Tyr Lys Lys Glu Asn Lys Ile Val Pro Ser Lys
    370                 375                 380

Glu Ile Val Trp Trp Met Asn Leu Ala Glu Lys Ile Pro Gln Ser Gln
385                 390                 395                 400

Tyr Asp Val Val Ser Asp His Val Ser Lys Val Thr Phe Phe Asn Leu
                405                 410                 415

Asn Glu Thr Lys Pro Arg Gly Lys Phe Thr Tyr Asp Ala Val Tyr Cys
            420                 425                 430

Cys Asn Glu His Glu Cys His His Arg Tyr Ala Glu Leu Tyr Val Ile
        435                 440                 445

Asp Val Asn Ile Asn Ile Ser Cys Glu Thr Asp Gly Tyr Leu Thr Lys
    450                 455                 460

Met Thr Cys Arg Trp Ser Thr Ser Thr Ile Gln Ser Leu Ala Glu Ser
465                 470                 475                 480

Thr Leu Gln Leu Arg Tyr His Arg Ser Ser Leu Tyr Cys Ser Asp Ile
                485                 490                 495

Pro Ser Ile His Pro Ile Ser Glu Pro Lys Asp Cys Tyr Leu Gln Ser
            500                 505                 510

Asp Gly Phe Tyr Glu Cys Ile Phe Gln Pro Ile Phe Leu Leu Ser Gly
        515                 520                 525

Tyr Thr Met Trp Ile Arg Ile Asn His Ser Leu Gly Ser Leu Asp Ser
    530                 535                 540

Pro Pro Thr Cys Val Leu Pro Asp Ser Val Val Lys Pro Leu Pro Pro
545                 550                 555                 560

Ser Ser Val Lys Ala Glu Ile Thr Ile Asn Ile Gly Leu Leu Lys Ile
                565                 570                 575

Ser Trp Glu Lys Pro Val Phe Pro Glu Asn Asn Leu Gln Phe Gln Ile
            580                 585                 590

Arg Tyr Gly Leu Ser Gly Lys Glu Val Gln Trp Lys Met Tyr Glu Val
        595                 600                 605

Tyr Asp Ala Lys Ser Lys Ser Val Ser Leu Pro Val Pro Asp Leu Cys
    610                 615                 620

Ala Val Tyr Ala Val Gln Val Arg Cys Lys Arg Leu Asp Gly Leu Gly
625                 630                 635                 640

Tyr Trp Ser Asn Trp Ser Asn Pro Ala Tyr Thr Val Val Met Asp Ile
                645                 650                 655

Lys Val Pro Met Arg Gly Pro Glu Phe Trp Arg Ile Ile Asn Gly Asp
            660                 665                 670

Thr Met Lys Lys Glu Lys Asn Val Thr Leu Leu Trp Lys Pro Leu Met
        675                 680                 685
```

-continued

Lys Asn Asp Ser Leu Cys Ser Val Gln Arg Tyr Val Ile Asn His His
690 695 700

Thr Ser Cys Asn Gly Thr Trp Ser Glu Asp Val Gly Asn His Thr Lys
705 710 715 720

Phe Thr Phe Leu Trp Thr Glu Gln Ala His Thr Val Thr Val Leu Ala
725 730 735

Ile Asn Ser Ile Gly Ala Ser Val Ala Asn Phe Asn Leu Thr Phe Ser
740 745 750

Trp Pro Met Ser Lys Val Asn Ile Val Gln Ser Leu Ser Ala Tyr Pro
755 760 765

Leu Asn Ser Ser Cys Val Ile Val Ser Trp Ile Leu Ser Pro Ser Asp
770 775 780

Tyr Lys Leu Met Tyr Phe Ile Ile Glu Trp Lys Asn Leu Asn Glu Asp
785 790 795 800

Gly Glu Ile Lys Trp Leu Arg Ile Ser Ser Ser Val Lys Lys Tyr Tyr
805 810 815

Ile His Asp His Phe Ile Pro Ile Glu Lys Tyr Gln Phe Ser Leu Tyr
820 825 830

Pro Ile Phe Met Glu Gly Val Gly Lys Pro Lys Ile Ile Asn Ser Phe
835 840 845

Thr Gln Asp Asp Ile Glu Lys His Gln Ser Asp Ala Gly Leu Tyr Val
850 855 860

Ile Val Pro Val Ile Ile Ser Ser Ser Ile Leu Leu Leu Gly Thr Leu
865 870 875 880

Leu Ile Ser His Gln Arg Met Lys Lys Leu Phe Trp Glu Asp Val Pro
885 890 895

Asn Pro Lys Asn Cys Ser Trp Ala Gln Gly Leu Asn Phe Gln Lys Arg
900 905 910

Thr Asp Ile Leu Asp Pro Pro Val Ala Thr Met Val Ser Lys Gly Glu
915 920 925

Glu Leu Phe Thr Gly Val Val Pro Ile Leu Val Glu Leu Asp Gly Asp
930 935 940

Val Asn Gly His Lys Phe Ser Val Ser Gly Glu Gly Glu Gly Asp Ala
945 950 955 960

Thr Tyr Gly Lys Leu Thr Leu Lys Phe Ile Cys Thr Thr Gly Lys Leu
965 970 975

Pro Val Pro Trp Pro Thr Leu Val Thr Thr Phe Gly Tyr Gly Val Gln
980 985 990

Cys Phe Ala Arg Tyr Pro Asp His Met Arg Gln His Asp Phe Phe Lys
995 1000 1005

Ser Ala Met Pro Glu Gly Tyr Val Gln Glu Arg Thr Ile Phe Phe
1010 1015 1020

Lys Asp Asp Gly Asn Tyr Lys Thr Arg Ala Glu Val Lys Phe Glu
1025 1030 1035

Gly Asp Thr Leu Val Asn Arg Ile Glu Leu Lys Gly Ile Asp Phe
1040 1045 1050

Lys Glu Asp Gly Asn Ile Leu Gly His Lys Leu Glu Tyr Asn Tyr
1055 1060 1065

Asn Ser His Asn Val Tyr Ile Met Ala Asp Lys Gln Lys Asn Gly
1070 1075 1080

Ile Lys Val Asn Phe Lys Ile Arg His Asn Ile Glu Asp Gly Ser
1085 1090 1095

Val Gln Leu Ala Asp His Tyr Gln Gln Asn Thr Pro Ile Gly Asp

-continued

```
    1100                1105                1110

Gly Pro  Val Leu Leu Pro Asp  Asn His Tyr Leu Ser  Tyr Gln Ser
    1115                1120                1125

Ala Leu  Ser Lys Asp Pro Asn  Glu Lys Arg Asp His  Met Val Leu
    1130                1135                1140

Leu Glu  Phe Val Thr Ala Ala  Gly Ile Thr Leu Gly  Met Asp Glu
    1145                1150                1155

Leu Tyr  Lys
    1160


<210> SEQ ID NO 15
<211> LENGTH: 396
<212> TYPE: DNA
<213> ORGANISM: Homo sapiens
<220> FEATURE:
<221> NAME/KEY: CDS
<222> LOCATION: (1)..(396)

<400> SEQUENCE: 15

atg gca ggc atc aaa gct ttg att agt ttg tcc ttt gga gga gca atc       48
Met Ala Gly Ile Lys Ala Leu Ile Ser Leu Ser Phe Gly Gly Ala Ile
1               5                   10                  15

gga ctg atg ttt ttg atg ctt gga tgt gcc ctt cca ata tac aac aaa       96
Gly Leu Met Phe Leu Met Leu Gly Cys Ala Leu Pro Ile Tyr Asn Lys
            20                  25                  30

tac tgg ccc ctc ttt gtt cta ttt ttt tac atc ctt tca cct att cca      144
Tyr Trp Pro Leu Phe Val Leu Phe Phe Tyr Ile Leu Ser Pro Ile Pro
        35                  40                  45

tac tgc ata gca aga aga tta gtg gat gat aca gat gct atg agt aac      192
Tyr Cys Ile Ala Arg Arg Leu Val Asp Asp Thr Asp Ala Met Ser Asn
    50                  55                  60

gct tgt aag gaa ctt gcc atc ttt ctt aca acg ggc att gtc gtg tca      240
Ala Cys Lys Glu Leu Ala Ile Phe Leu Thr Thr Gly Ile Val Val Ser
65                  70                  75                  80

gct ttt gga ctc cct att gta ttt gcc aga gca cat ctg att gag tgg      288
Ala Phe Gly Leu Pro Ile Val Phe Ala Arg Ala His Leu Ile Glu Trp
                85                  90                  95

gga gct tgt gca ctt gtt ctc aca gga aac aca gtc atc ttt gca act      336
Gly Ala Cys Ala Leu Val Leu Thr Gly Asn Thr Val Ile Phe Ala Thr
            100                 105                 110

ata cta ggc ttt ttc ttg gtc ttt gga agc aat gac gac ttc agc tgg      384
Ile Leu Gly Phe Phe Leu Val Phe Gly Ser Asn Asp Asp Phe Ser Trp
        115                 120                 125

cag cag tgg tga                                                       396
Gln Gln Trp
    130


<210> SEQ ID NO 16
<211> LENGTH: 131
<212> TYPE: PRT
<213> ORGANISM: Homo sapiens

<400> SEQUENCE: 16

Met Ala Gly Ile Lys Ala Leu Ile Ser Leu Ser Phe Gly Gly Ala Ile
1               5                   10                  15

Gly Leu Met Phe Leu Met Leu Gly Cys Ala Leu Pro Ile Tyr Asn Lys
            20                  25                  30

Tyr Trp Pro Leu Phe Val Leu Phe Phe Tyr Ile Leu Ser Pro Ile Pro
        35                  40                  45

Tyr Cys Ile Ala Arg Arg Leu Val Asp Asp Thr Asp Ala Met Ser Asn
```

-continued

```
    50                  55                  60

Ala Cys Lys Glu Leu Ala Ile Phe Leu Thr Thr Gly Ile Val Val Ser
65                  70                  75                  80

Ala Phe Gly Leu Pro Ile Val Phe Ala Arg Ala His Leu Ile Glu Trp
                85                  90                  95

Gly Ala Cys Ala Leu Val Leu Thr Gly Asn Thr Val Ile Phe Ala Thr
            100                 105                 110

Ile Leu Gly Phe Phe Leu Val Phe Gly Ser Asn Asp Asp Phe Ser Trp
        115                 120                 125

Gln Gln Trp
    130


<210> SEQ ID NO 17
<211> LENGTH: 1359
<212> TYPE: DNA
<213> ORGANISM: Homo sapiens
<220> FEATURE:
<221> NAME/KEY: misc_feature
<223> OTHER INFORMATION: MY47 LUC
<220> FEATURE:
<221> NAME/KEY: CDS
<222> LOCATION: (1)..(1359)

<400> SEQUENCE: 17

atg gca ggc atc aaa gct ttg att agt ttg tcc ttt gga gga gca atc        48
Met Ala Gly Ile Lys Ala Leu Ile Ser Leu Ser Phe Gly Gly Ala Ile
1               5                   10                  15

gga ctg atg ttt ttg atg ctt gga tgt gcc ctt cca ata tac aac aaa        96
Gly Leu Met Phe Leu Met Leu Gly Cys Ala Leu Pro Ile Tyr Asn Lys
            20                  25                  30

tac tgg ccc ctc ttt gtt cta ttt ttt tac atc ctt tca cct att cca       144
Tyr Trp Pro Leu Phe Val Leu Phe Phe Tyr Ile Leu Ser Pro Ile Pro
        35                  40                  45

tac tgc ata gca aga aga tta gtg gat gat aca gat gct atg agt aac       192
Tyr Cys Ile Ala Arg Arg Leu Val Asp Asp Thr Asp Ala Met Ser Asn
    50                  55                  60

gct tgt aag gaa ctt gcc atc ttt ctt aca acg ggc att gtc gtg tca       240
Ala Cys Lys Glu Leu Ala Ile Phe Leu Thr Thr Gly Ile Val Val Ser
65                  70                  75                  80

gct ttt gga ctc cct att gta ttt gcc aga gca cat ctg att gag tgg       288
Ala Phe Gly Leu Pro Ile Val Phe Ala Arg Ala His Leu Ile Glu Trp
                85                  90                  95

gga gct tgt gca ctt gtt ctc aca gga aac aca gtc atc ttt gca act       336
Gly Ala Cys Ala Leu Val Leu Thr Gly Asn Thr Val Ile Phe Ala Thr
            100                 105                 110

ata cta ggc ttt ttc ttg gtc ttt gga agc aat gac gac ttc agc tgg       384
Ile Leu Gly Phe Phe Leu Val Phe Gly Ser Asn Asp Asp Phe Ser Trp
        115                 120                 125

cag cag tgg cga ccg gtg gat cca ccg gct aga gcc acc atg acc agc       432
Gln Gln Trp Arg Pro Val Asp Pro Pro Ala Arg Ala Thr Met Thr Ser
    130                 135                 140

aag gtg tac gac ccc gag cag agg aag agg atg atc acc ggc ccc cag       480
Lys Val Tyr Asp Pro Glu Gln Arg Lys Arg Met Ile Thr Gly Pro Gln
145                 150                 155                 160

tgg tgg gcc agg tgc aag cag atg aac gtg ctg gac agc ttc atc aac       528
Trp Trp Ala Arg Cys Lys Gln Met Asn Val Leu Asp Ser Phe Ile Asn
                165                 170                 175

tac tac gac agc gag aag cac gcc gag aac gcc gtg atc ttc ctg cac       576
Tyr Tyr Asp Ser Glu Lys His Ala Glu Asn Ala Val Ile Phe Leu His
            180                 185                 190
```

-continued ggc aac gcc gct agc agc tac ctg tgg agg cac gtg gtg ccc cac atc 624
Gly Asn Ala Ala Ser Ser Tyr Leu Trp Arg His Val Val Pro His Ile
195 200 205 gag ccc gtg gcc agg tgc atc atc ccc gat ctg atc ggc atg ggc aag 672
Glu Pro Val Ala Arg Cys Ile Ile Pro Asp Leu Ile Gly Met Gly Lys
210 215 220 agc ggc aag agc ggc aac ggc agc tac agg ctg ctg gac cac tac aag 720
Ser Gly Lys Ser Gly Asn Gly Ser Tyr Arg Leu Leu Asp His Tyr Lys
225 230 235 240 tac ctg acc gcc tgg ttc gag ctc ctg aac ctg ccc aag aag atc atc 768
Tyr Leu Thr Ala Trp Phe Glu Leu Leu Asn Leu Pro Lys Lys Ile Ile
245 250 255 ttc gtg ggc cac gac tgg ggc gcc tgc ctg gcc ttc cac tac agc tac 816
Phe Val Gly His Asp Trp Gly Ala Cys Leu Ala Phe His Tyr Ser Tyr
260 265 270 gag cac cag gac aag atc aag gcc atc gtg cac gcc gag agc gtg gtg 864
Glu His Gln Asp Lys Ile Lys Ala Ile Val His Ala Glu Ser Val Val
275 280 285 gac gtg atc gag agc tgg gac gag tgg cca gac atc gag gag gac atc 912
Asp Val Ile Glu Ser Trp Asp Glu Trp Pro Asp Ile Glu Glu Asp Ile
290 295 300 gcc ctg atc aag agc gag gag ggc gag aag atg gtg ctg gag aac aac 960
Ala Leu Ile Lys Ser Glu Glu Gly Glu Lys Met Val Leu Glu Asn Asn
305 310 315 320 ttc ttc gtg gag acc atg ctg ccc agc aag atc atg aga aag ctg gag 1008
Phe Phe Val Glu Thr Met Leu Pro Ser Lys Ile Met Arg Lys Leu Glu
325 330 335 ccc gag gag ttc gcc gcc tac ctg gag ccc ttc aag gag aag ggc gag 1056
Pro Glu Glu Phe Ala Ala Tyr Leu Glu Pro Phe Lys Glu Lys Gly Glu
340 345 350 gtg aga aga ccc acc ctg agc tgg ccc aga gag atc ccc ctg gtg aag 1104
Val Arg Arg Pro Thr Leu Ser Trp Pro Arg Glu Ile Pro Leu Val Lys
355 360 365 ggc ggc aag ccc gac gtg gtg cag atc gtg aga aac tac aac gcc tac 1152
Gly Gly Lys Pro Asp Val Val Gln Ile Val Arg Asn Tyr Asn Ala Tyr
370 375 380 ctg aga gcc agc gac gac ctg ccc aag atg ttc atc gag agc gac ccc 1200
Leu Arg Ala Ser Asp Asp Leu Pro Lys Met Phe Ile Glu Ser Asp Pro
385 390 395 400 ggc ttc ttc agc aac gcc atc gtg gag ggc gcc aag aag ttc ccc aac 1248
Gly Phe Phe Ser Asn Ala Ile Val Glu Gly Ala Lys Lys Phe Pro Asn
405 410 415 acc gag ttc gtg aag gtg aag ggc ctg cac ttc agc cag gag gac gcc 1296
Thr Glu Phe Val Lys Val Lys Gly Leu His Phe Ser Gln Glu Asp Ala
420 425 430 ccc gac gag atg ggc aag tac atc aag agc ttc gtg gag aga gtg ctg 1344
Pro Asp Glu Met Gly Lys Tyr Ile Lys Ser Phe Val Glu Arg Val Leu
435 440 445 aag aac gag cag taa 1359
Lys Asn Glu Gln
450

<210> SEQ ID NO 18
<211> LENGTH: 452
<212> TYPE: PRT
<213> ORGANISM: Homo sapiens
<220> FEATURE:
<221> NAME/KEY: misc_feature
<223> OTHER INFORMATION: MY47 LUC

<400> SEQUENCE: 18

-continued

```
Met Ala Gly Ile Lys Ala Leu Ile Ser Leu Ser Phe Gly Gly Ala Ile
1               5                   10                  15

Gly Leu Met Phe Leu Met Leu Gly Cys Ala Leu Pro Ile Tyr Asn Lys
            20                  25                  30

Tyr Trp Pro Leu Phe Val Leu Phe Phe Tyr Ile Leu Ser Pro Ile Pro
        35                  40                  45

Tyr Cys Ile Ala Arg Arg Leu Val Asp Asp Thr Asp Ala Met Ser Asn
    50                  55                  60

Ala Cys Lys Glu Leu Ala Ile Phe Leu Thr Thr Gly Ile Val Val Ser
65                  70                  75                  80

Ala Phe Gly Leu Pro Ile Val Phe Ala Arg Ala His Leu Ile Glu Trp
                85                  90                  95

Gly Ala Cys Ala Leu Val Leu Thr Gly Asn Thr Val Ile Phe Ala Thr
            100                 105                 110

Ile Leu Gly Phe Phe Leu Val Phe Gly Ser Asn Asp Asp Phe Ser Trp
        115                 120                 125

Gln Gln Trp Arg Pro Val Asp Pro Pro Ala Arg Ala Thr Met Thr Ser
    130                 135                 140

Lys Val Tyr Asp Pro Glu Gln Arg Lys Arg Met Ile Thr Gly Pro Gln
145                 150                 155                 160

Trp Trp Ala Arg Cys Lys Gln Met Asn Val Leu Asp Ser Phe Ile Asn
                165                 170                 175

Tyr Tyr Asp Ser Glu Lys His Ala Glu Asn Ala Val Ile Phe Leu His
            180                 185                 190

Gly Asn Ala Ala Ser Ser Tyr Leu Trp Arg His Val Val Pro His Ile
        195                 200                 205

Glu Pro Val Ala Arg Cys Ile Ile Pro Asp Leu Ile Gly Met Gly Lys
    210                 215                 220

Ser Gly Lys Ser Gly Asn Gly Ser Tyr Arg Leu Leu Asp His Tyr Lys
225                 230                 235                 240

Tyr Leu Thr Ala Trp Phe Glu Leu Leu Asn Leu Pro Lys Lys Ile Ile
                245                 250                 255

Phe Val Gly His Asp Trp Gly Ala Cys Leu Ala Phe His Tyr Ser Tyr
            260                 265                 270

Glu His Gln Asp Lys Ile Lys Ala Ile Val His Ala Glu Ser Val Val
        275                 280                 285

Asp Val Ile Glu Ser Trp Asp Glu Trp Pro Asp Ile Glu Glu Asp Ile
    290                 295                 300

Ala Leu Ile Lys Ser Glu Glu Gly Glu Lys Met Val Leu Glu Asn Asn
305                 310                 315                 320

Phe Phe Val Glu Thr Met Leu Pro Ser Lys Ile Met Arg Lys Leu Glu
                325                 330                 335

Pro Glu Glu Phe Ala Ala Tyr Leu Glu Pro Phe Lys Glu Lys Gly Glu
            340                 345                 350

Val Arg Arg Pro Thr Leu Ser Trp Pro Arg Glu Ile Pro Leu Val Lys
        355                 360                 365

Gly Gly Lys Pro Asp Val Val Gln Ile Val Arg Asn Tyr Asn Ala Tyr
    370                 375                 380

Leu Arg Ala Ser Asp Asp Leu Pro Lys Met Phe Ile Glu Ser Asp Pro
385                 390                 395                 400

Gly Phe Phe Ser Asn Ala Ile Val Glu Gly Ala Lys Lys Phe Pro Asn
                405                 410                 415

Thr Glu Phe Val Lys Val Lys Gly Leu His Phe Ser Gln Glu Asp Ala
```

-continued

```
                    420                 425                 430
Pro Asp Glu Met Gly Lys Tyr Ile Lys Ser Phe Val Glu Arg Val Leu
        435                 440                 445

Lys Asn Glu Gln
    450

<210> SEQ ID NO 19
<211> LENGTH: 1140
<212> TYPE: DNA
<213> ORGANISM: Artificial Sequence
<220> FEATURE:
<223> OTHER INFORMATION: MYO47 YFP
<220> FEATURE:
<221> NAME/KEY: misc_feature
<223> OTHER INFORMATION: MY47 YFP
<220> FEATURE:
<221> NAME/KEY: CDS
<222> LOCATION: (1)..(1140)

<400> SEQUENCE: 19

atg gca ggc atc aaa gct ttg att agt ttg tcc ttt gga gga gca atc      48
Met Ala Gly Ile Lys Ala Leu Ile Ser Leu Ser Phe Gly Gly Ala Ile
1               5                   10                  15

gga ctg atg ttt ttg atg ctt gga tgt gcc ctt cca ata tac aac aaa      96
Gly Leu Met Phe Leu Met Leu Gly Cys Ala Leu Pro Ile Tyr Asn Lys
            20                  25                  30

tac tgg ccc ctc ttt gtt cta ttt ttt tac atc ctt tca cct att cca     144
Tyr Trp Pro Leu Phe Val Leu Phe Phe Tyr Ile Leu Ser Pro Ile Pro
        35                  40                  45

tac tgc ata gca aga aga tta gtg gat gat aca gat gct atg agt aac     192
Tyr Cys Ile Ala Arg Arg Leu Val Asp Asp Thr Asp Ala Met Ser Asn
    50                  55                  60

gct tgt aag gaa ctt gcc atc ttt ctt aca acg ggc att gtc gtg tca     240
Ala Cys Lys Glu Leu Ala Ile Phe Leu Thr Thr Gly Ile Val Val Ser
65                  70                  75                  80

gct ttt gga ctc cct att gta ttt gcc aga gca cat ctg att gag tgg     288
Ala Phe Gly Leu Pro Ile Val Phe Ala Arg Ala His Leu Ile Glu Trp
                85                  90                  95

gga gct tgt gca ctt gtt ctc aca gga aac aca gtc atc ttt gca act     336
Gly Ala Cys Ala Leu Val Leu Thr Gly Asn Thr Val Ile Phe Ala Thr
            100                 105                 110

ata cta ggc ttt ttc ttg gtc ttt gga agc aat gac gac ttc agc tgg     384
Ile Leu Gly Phe Phe Leu Val Phe Gly Ser Asn Asp Asp Phe Ser Trp
        115                 120                 125

cag cag tgg cga ccg gtg gat cca ccg gtc gcc acc atg gtg agc aag     432
Gln Gln Trp Arg Pro Val Asp Pro Pro Val Ala Thr Met Val Ser Lys
    130                 135                 140

ggc gag gag ctg ttc acc ggg gtg gtg ccc atc ctg gtc gag ctg gac     480
Gly Glu Glu Leu Phe Thr Gly Val Val Pro Ile Leu Val Glu Leu Asp
145                 150                 155                 160

ggc gac gta aac ggc cac aag ttc agc gtg tcc ggc gag ggc gag ggc     528
Gly Asp Val Asn Gly His Lys Phe Ser Val Ser Gly Glu Gly Glu Gly
                165                 170                 175

gat gcc acc tac ggc aag ctg acc ctg aag ttc atc tgc acc acc ggc     576
Asp Ala Thr Tyr Gly Lys Leu Thr Leu Lys Phe Ile Cys Thr Thr Gly
            180                 185                 190

aag ctg ccc gtg ccc tgg ccc acc ctc gtg acc acc ttc ggc tac ggc     624
Lys Leu Pro Val Pro Trp Pro Thr Leu Val Thr Thr Phe Gly Tyr Gly
        195                 200                 205

gtg cag tgc ttc gcc cgc tac ccc gac cac atg cgc cag cac gac ttc     672
Val Gln Cys Phe Ala Arg Tyr Pro Asp His Met Arg Gln His Asp Phe
    210                 215                 220
```

```
ttc aag tcc gcc atg ccc gaa ggc tac gtc cag gag cgc acc atc ttc        720
Phe Lys Ser Ala Met Pro Glu Gly Tyr Val Gln Glu Arg Thr Ile Phe
225                 230                 235                 240

ttc aag gac gac ggc aac tac aag acc cgc gcc gag gtg aag ttc gag        768
Phe Lys Asp Asp Gly Asn Tyr Lys Thr Arg Ala Glu Val Lys Phe Glu
            245                 250                 255

ggc gac acc ctg gtg aac cgc atc gag ctg aag ggc atc gac ttc aag        816
Gly Asp Thr Leu Val Asn Arg Ile Glu Leu Lys Gly Ile Asp Phe Lys
        260                 265                 270

gag gac ggc aac atc ctg ggg cac aag ctg gag tac aac tac aac agc        864
Glu Asp Gly Asn Ile Leu Gly His Lys Leu Glu Tyr Asn Tyr Asn Ser
    275                 280                 285

cac aac gtc tat atc atg gcc gac aag cag aag aac ggc atc aag gtg        912
His Asn Val Tyr Ile Met Ala Asp Lys Gln Lys Asn Gly Ile Lys Val
290                 295                 300

aac ttc aag atc cgc cac aac atc gag gac ggc agc gtg cag ctc gcc        960
Asn Phe Lys Ile Arg His Asn Ile Glu Asp Gly Ser Val Gln Leu Ala
305                 310                 315                 320

gac cac tac cag cag aac acc ccc atc ggc gac ggc ccc gtg ctg ctg       1008
Asp His Tyr Gln Gln Asn Thr Pro Ile Gly Asp Gly Pro Val Leu Leu
            325                 330                 335

ccc gac aac cac tac ctg agc tac cag tcc gcc ctg agc aaa gac ccc       1056
Pro Asp Asn His Tyr Leu Ser Tyr Gln Ser Ala Leu Ser Lys Asp Pro
        340                 345                 350

aac gag aag cgc gat cac atg gtc ctg ctg gag ttc gtg acc gcc gcc       1104
Asn Glu Lys Arg Asp His Met Val Leu Leu Glu Phe Val Thr Ala Ala
    355                 360                 365

ggg atc act ctc ggc atg gac gag ctg tac aag taa                       1140
Gly Ile Thr Leu Gly Met Asp Glu Leu Tyr Lys
        370                 375

<210> SEQ ID NO 20
<211> LENGTH: 379
<212> TYPE: PRT
<213> ORGANISM: Artificial Sequence
<220> FEATURE:
<223> OTHER INFORMATION: MYO47 YFP
<220> FEATURE:
<221> NAME/KEY: misc_feature
<223> OTHER INFORMATION: MY47 YFP

<400> SEQUENCE: 20

Met Ala Gly Ile Lys Ala Leu Ile Ser Leu Ser Phe Gly Gly Ala Ile
1               5                   10                  15

Gly Leu Met Phe Leu Met Leu Gly Cys Ala Leu Pro Ile Tyr Asn Lys
            20                  25                  30

Tyr Trp Pro Leu Phe Val Leu Phe Phe Tyr Ile Leu Ser Pro Ile Pro
        35                  40                  45

Tyr Cys Ile Ala Arg Arg Leu Val Asp Asp Thr Asp Ala Met Ser Asn
    50                  55                  60

Ala Cys Lys Glu Leu Ala Ile Phe Leu Thr Thr Gly Ile Val Val Ser
65                  70                  75                  80

Ala Phe Gly Leu Pro Ile Val Phe Ala Arg Ala His Leu Ile Glu Trp
                85                  90                  95

Gly Ala Cys Ala Leu Val Leu Thr Gly Asn Thr Val Ile Phe Ala Thr
            100                 105                 110

Ile Leu Gly Phe Phe Leu Val Phe Gly Ser Asn Asp Asp Phe Ser Trp
        115                 120                 125

Gln Gln Trp Arg Pro Val Asp Pro Pro Val Ala Thr Met Val Ser Lys
```

-continued

```
    130                 135                 140

Gly Glu Glu Leu Phe Thr Gly Val Val Pro Ile Leu Val Glu Leu Asp
145                 150                 155                 160

Gly Asp Val Asn Gly His Lys Phe Ser Val Ser Gly Glu Gly Glu Gly
                165                 170                 175

Asp Ala Thr Tyr Gly Lys Leu Thr Leu Lys Phe Ile Cys Thr Thr Gly
            180                 185                 190

Lys Leu Pro Val Pro Trp Pro Thr Leu Val Thr Thr Phe Gly Tyr Gly
        195                 200                 205

Val Gln Cys Phe Ala Arg Tyr Pro Asp His Met Arg Gln His Asp Phe
    210                 215                 220

Phe Lys Ser Ala Met Pro Glu Gly Tyr Val Gln Glu Arg Thr Ile Phe
225                 230                 235                 240

Phe Lys Asp Asp Gly Asn Tyr Lys Thr Arg Ala Glu Val Lys Phe Glu
                245                 250                 255

Gly Asp Thr Leu Val Asn Arg Ile Glu Leu Lys Gly Ile Asp Phe Lys
            260                 265                 270

Glu Asp Gly Asn Ile Leu Gly His Lys Leu Glu Tyr Asn Tyr Asn Ser
        275                 280                 285

His Asn Val Tyr Ile Met Ala Asp Lys Gln Lys Asn Gly Ile Lys Val
    290                 295                 300

Asn Phe Lys Ile Arg His Asn Ile Glu Asp Gly Ser Val Gln Leu Ala
305                 310                 315                 320

Asp His Tyr Gln Gln Asn Thr Pro Ile Gly Asp Gly Pro Val Leu Leu
                325                 330                 335

Pro Asp Asn His Tyr Leu Ser Tyr Gln Ser Ala Leu Ser Lys Asp Pro
            340                 345                 350

Asn Glu Lys Arg Asp His Met Val Leu Leu Glu Phe Val Thr Ala Ala
        355                 360                 365

Gly Ile Thr Leu Gly Met Asp Glu Leu Tyr Lys
    370                 375
```

<210> SEQ ID NO 21
<211> LENGTH: 1114
<212> TYPE: DNA
<213> ORGANISM: Homo sapiens

<400> SEQUENCE: 21

```
gtctggcttg ggcaggctgc ccgggccgtg gcaggaagcc ggaagcagcc gcggccccag     60

ttcgggagac atggcgggcg ttaaagctct cgtggcatta tccttcagtg gggctattgg    120

actgactttt cttatgctgg gatgtgcctt agaggattat ggcgtttact ggcccttatt    180

cgtcctgatt ttccacgcca tctcccccat cccccatttc attgccaaaa gagtcaccta    240

tgactcagat gcaaccagta gtgcctgtcg ggaactggca tatttcttca ctactggaat    300

tgttgtttct gcctttggat ttcctgttat tcttgctcgt gtggctgtga tcaaatgggg    360

agcctgcggc cttgtgttgg caggcaatgc agtcattttc cttacaattc aagggttttt    420

ccttatattt ggaagaggag atgattttag ctgggagcag tggtagcact ttattctgat    480

tacagtgcat tgaatttctt agaactcata ctatctgtat acatgtgcac atgcggcatt    540

ttactatgaa atttaatatg ctgggttttt taataccttt atatatcatg ttcactttaa    600

gaaagacttc ataagtagga gatgagtttt attctcagca aatagacctg tcaaatttag    660

attatgttac tcaaattatg ttacttgttt ggctgttcat gtagtcacgg tgctctcaga    720
```

-continued

```
aaatatatta acgcagtctt gtaggcagct gccaccttat gcagtgcatc gaaacctttt    780

gcttggggat gtgcttggag aggcagataa cgctgaagca ggcctctcat gacccaggaa    840

ggccggggtg gatccctctt tgtgttgtag tccatgctat taaaagtgtg gcccacagac    900

caagagcctc aacatttcct agagccttat tagaaatgca gaatctgaag ccccactctg    960

gacccaggac attttgatga gatccaaagg agttgtatgc acatgaaagt ttgagaagca   1020

tcatcataga gaagtaaaca tcacacccaa cttccttatc tttccagtgg ctaaaccact   1080

taacctctct gggtgttacc tgctcatttg ttta                               1114


<210> SEQ ID NO 22
<211> LENGTH: 20
<212> TYPE: DNA
<213> ORGANISM: Artificial Sequence
<220> FEATURE:
<223> OTHER INFORMATION: AS01

<400> SEQUENCE: 22

gcttcctgcc acggcccggg                                                 20


<210> SEQ ID NO 23
<211> LENGTH: 20
<212> TYPE: DNA
<213> ORGANISM: Artificial Sequence
<220> FEATURE:
<223> OTHER INFORMATION: AS02

<400> SEQUENCE: 23

gccatgtctc ccgaactggg                                                 20


<210> SEQ ID NO 24
<211> LENGTH: 20
<212> TYPE: DNA
<213> ORGANISM: Artificial Sequence
<220> FEATURE:
<223> OTHER INFORMATION: AS03

<400> SEQUENCE: 24

aacgcccgcc atgtctcccg                                                 20


<210> SEQ ID NO 25
<211> LENGTH: 20
<212> TYPE: DNA
<213> ORGANISM: Artificial Sequence
<220> FEATURE:
<223> OTHER INFORMATION: AS04

<400> SEQUENCE: 25

agagctttaa cgcccgccat                                                 20


<210> SEQ ID NO 26
<211> LENGTH: 20
<212> TYPE: DNA
<213> ORGANISM: Artificial Sequence
<220> FEATURE:
<223> OTHER INFORMATION: AS05

<400> SEQUENCE: 26

ggataatgcc acgagagctt                                                 20


<210> SEQ ID NO 27
<211> LENGTH: 20
<212> TYPE: DNA
<213> ORGANISM: Artificial Sequence
```

-continued

<220> FEATURE:
<223> OTHER INFORMATION: AS06

<400> SEQUENCE: 27
aaggcacatc ccagcataag 20

<210> SEQ ID NO 28
<211> LENGTH: 20
<212> TYPE: DNA
<213> ORGANISM: Artificial Sequence
<220> FEATURE:
<223> OTHER INFORMATION: AS07

<400> SEQUENCE: 28
ccataatcct ctaaggcaca 20

<210> SEQ ID NO 29
<211> LENGTH: 20
<212> TYPE: DNA
<213> ORGANISM: Artificial Sequence
<220> FEATURE:
<223> OTHER INFORMATION: AS08

<400> SEQUENCE: 29
cagtaaacgc cataatcctc 20

<210> SEQ ID NO 30
<211> LENGTH: 20
<212> TYPE: DNA
<213> ORGANISM: Artificial Sequence
<220> FEATURE:
<223> OTHER INFORMATION: AS09

<400> SEQUENCE: 30
aataagggcc agtaaacgcc 20

<210> SEQ ID NO 31
<211> LENGTH: 20
<212> TYPE: DNA
<213> ORGANISM: Artificial Sequence
<220> FEATURE:
<223> OTHER INFORMATION: AS10

<400> SEQUENCE: 31
atgccagttc ccgacaggca 20

<210> SEQ ID NO 32
<211> LENGTH: 22
<212> TYPE: DNA
<213> ORGANISM: Artificial Sequence
<220> FEATURE:
<223> OTHER INFORMATION: AS11

<400> SEQUENCE: 32
aaatatgcca gttcccgaca gg 22

<210> SEQ ID NO 33
<211> LENGTH: 20
<212> TYPE: DNA
<213> ORGANISM: Artificial Sequence
<220> FEATURE:
<223> OTHER INFORMATION: AS12

<400> SEQUENCE: 33
aagaaatatg ccagttcccg 20

-continued

<210> SEQ ID NO 34
<211> LENGTH: 20
<212> TYPE: DNA
<213> ORGANISM: Artificial Sequence
<220> FEATURE:
<223> OTHER INFORMATION: AS13

<400> SEQUENCE: 34
cattgcctgc caacacaagg 20

<210> SEQ ID NO 35
<211> LENGTH: 20
<212> TYPE: DNA
<213> ORGANISM: Artificial Sequence
<220> FEATURE:
<223> OTHER INFORMATION: AS15

<400> SEQUENCE: 35
aaccgccgac ctgtcctccg 20

<210> SEQ ID NO 36
<211> LENGTH: 22
<212> TYPE: DNA
<213> ORGANISM: Artificial Sequence
<220> FEATURE:
<223> OTHER INFORMATION: AS16

<400> SEQUENCE: 36
aaatctgcac gttacagcca gg 22

<210> SEQ ID NO 37
<211> LENGTH: 21
<212> TYPE: DNA
<213> ORGANISM: Artificial Sequence
<220> FEATURE:
<223> OTHER INFORMATION: Artificial

<400> SEQUENCE: 37
gugccugucg ggaacuggct t 21

<210> SEQ ID NO 38
<211> LENGTH: 21
<212> TYPE: DNA
<213> ORGANISM: Artificial Sequence
<220> FEATURE:
<223> OTHER INFORMATION: Artificial

<400> SEQUENCE: 38
gccaguuccc gacaggcact t 21

<210> SEQ ID NO 39
<211> LENGTH: 38
<212> TYPE: DNA
<213> ORGANISM: Artificial Sequence
<220> FEATURE:
<223> OTHER INFORMATION: Artificial

<400> SEQUENCE: 39
tctcttgaat gaaacacatg tgcacacaca aacaaggc 38

<210> SEQ ID NO 40
<211> LENGTH: 40
<212> TYPE: DNA
<213> ORGANISM: Artificial Sequence
<220> FEATURE:
<223> OTHER INFORMATION: Artificial -continued

<400> SEQUENCE: 40
gctctagaaa aatgtgtgca catgtgtttc atctcttgaa 40

<210> SEQ ID NO 41
<211> LENGTH: 35
<212> TYPE: DNA
<213> ORGANISM: Artificial Sequence
<220> FEATURE:
<223> OTHER INFORMATION: Artificial

<400> SEQUENCE: 41
ccatctaggc caagcttatc cgacgccgcc atctc 35

<210> SEQ ID NO 42
<211> LENGTH: 47
<212> TYPE: DNA
<213> ORGANISM: Artificial Sequence
<220> FEATURE:
<223> OTHER INFORMATION: Artificial

<400> SEQUENCE: 42
tgtgtgcaca tgtgtttcat tcaagagatg aaacacatgt gcacaca 47

<210> SEQ ID NO 43
<211> LENGTH: 14
<212> TYPE: DNA
<213> ORGANISM: Artificial Sequence
<220> FEATURE:
<223> OTHER INFORMATION: Artificial

<400> SEQUENCE: 43
ccgtggcagg aagc 14

<210> SEQ ID NO 44
<211> LENGTH: 20
<212> TYPE: DNA
<213> ORGANISM: Artificial Sequence
<220> FEATURE:
<223> OTHER INFORMATION: Artificial

<400> SEQUENCE: 44
gcagcgacag ccccagctcc 20

<210> SEQ ID NO 45
<211> LENGTH: 16
<212> TYPE: DNA
<213> ORGANISM: Artificial Sequence
<220> FEATURE:
<223> OTHER INFORMATION: Artificial

<400> SEQUENCE: 45
cagccacacg agcaag 16

<210> SEQ ID NO 46
<211> LENGTH: 15
<212> TYPE: DNA
<213> ORGANISM: Artificial Sequence
<220> FEATURE:
<223> OTHER INFORMATION: Artificial

<400> SEQUENCE: 46
ggagaaggct ggggc 15

<210> SEQ ID NO 47

-continued

<211> LENGTH: 17
<212> TYPE: DNA
<213> ORGANISM: Artificial Sequence
<220> FEATURE:
<223> OTHER INFORMATION: Artificial

<400> SEQUENCE: 47
gatggcatgg actgtgg 17

<210> SEQ ID NO 48
<211> LENGTH: 131
<212> TYPE: PRT
<213> ORGANISM: Homo sapiens

<400> SEQUENCE: 48

Met Ala Gly Ile Lys Ala Leu Ile Ser Leu Ser Phe Gly Gly Ala Ile
1 5 10 15

Gly Leu Met Phe Leu Met Leu Gly Cys Ala Leu Pro Ile Tyr Asn Lys
20 25 30

Tyr Trp Pro Leu Phe Val Leu Phe Phe Tyr Ile Leu Ser Pro Ile Pro
35 40 45

Tyr Cys Ile Ala Arg Arg Leu Val Asp Asp Thr Asp Ala Met Ser Asn
50 55 60

Ala Cys Lys Glu Leu Ala Ile Phe Leu Thr Thr Gly Ile Val Val Ser
65 70 75 80

Ala Phe Gly Leu Pro Ile Val Phe Ala Arg Ala His Leu Ile Glu Trp
85 90 95

Gly Ala Cys Ala Leu Val Leu Thr Gly Asn Thr Val Ile Phe Ala Thr
100 105 110

Ile Leu Gly Phe Phe Leu Val Phe Gly Ser Lys Asp Asp Phe Ser Trp
115 120 125

Gln Gln Trp
130

<210> SEQ ID NO 49
<211> LENGTH: 142
<212> TYPE: PRT
<213> ORGANISM: C.elegans

<400> SEQUENCE: 49

Met Cys Cys His Ile His Ile Gln Cys Phe Asp Cys Cys Ser Met Lys
1 5 10 15

Asn Thr Ile Leu Ala Val Ala Ala Leu Ala Phe Ala Gly Val Val Phe
20 25 30

Leu Thr Phe Leu Val Leu Gly Cys Ala Leu Pro Arg Tyr Phe Thr Trp
35 40 45

Thr Pro Met Phe Val Ile Thr Phe Tyr Val Leu Ser Pro Val Pro Leu
50 55 60

Leu Ile Arg Arg Phe Gln Glu Asp Met Thr Gly Thr Asn Ala Cys Ile
65 70 75 80

Glu Ala Leu Phe Ile Thr Thr Gly Ile Val Ile Ser Ala Phe Ala Leu
85 90 95

Pro Ile Val Leu Ala His Ala Gly Thr Ile Ala Met Ser Ala Cys Phe
100 105 110

Leu Ile Phe Ile Ala Asn Ser Ile Asn Phe Ser Val Ile Ile Phe Tyr
115 120 125

Arg Ile Phe Asn Gly Glu Asp Met Asn Gly Met Ser Leu Trp
130 135 140

-continued

<210> SEQ ID NO 50
<211> LENGTH: 139
<212> TYPE: PRT
<213> ORGANISM: Yeast

<400> SEQUENCE: 50

```
Met Met Glu Phe Lys Val Ser Pro Leu Thr Lys Ile Ile Ser Leu Ser
1               5                   10                  15

Gly Phe Leu Ala Leu Gly Phe Leu Leu Val Ile Leu Ser Cys Ala Leu
            20                  25                  30

Phe His Asn Tyr Tyr Pro Leu Phe Asp Ile Leu Ile Phe Leu Leu Ala
        35                  40                  45

Pro Ile Pro Asn Thr Phe Asn Ala Gly Asn Lys Tyr His Thr Ser Asp
    50                  55                  60

Phe Met Ser Asp Ser Ser Asn Thr Gly Gln Asp Leu Ala His Phe Leu
65                  70                  75                  80

Thr Gly Met Leu Val Thr Ser Gly Ile Ala Leu Phe Val Val Phe Tyr
                85                  90                  95

His Cys Gln Leu Ile Gly His Leu Ser Cys Ile Met Cys Met Ile Gly
            100                 105                 110

Gly Leu Ile Thr Tyr Ser Ser Ile Val Ile Phe Lys Trp Phe Phe Lys
        115                 120                 125

Lys Asp Phe Asn Glu Asp Asp Ser Leu Phe Gly
    130                 135
```

<210> SEQ ID NO 51
<211> LENGTH: 152
<212> TYPE: PRT
<213> ORGANISM: Artificial
<220> FEATURE:
<223> OTHER INFORMATION: Consensus sequence human(2), C.elegans and yeast
<220> FEATURE:
<221> NAME/KEY: MISC_FEATURE
<222> LOCATION: (11)..(11)
<223> OTHER INFORMATION: M or D
<220> FEATURE:
<221> NAME/KEY: MISC_FEATURE
<222> LOCATION: (12)..(12)
<223> OTHER INFORMATION: M or C
<220> FEATURE:
<221> NAME/KEY: MISC_FEATURE
<222> LOCATION: (13)..(13)
<223> OTHER INFORMATION: E or C
<220> FEATURE:
<221> NAME/KEY: MISC_FEATURE
<222> LOCATION: (14)..(14)
<223> OTHER INFORMATION: F or S
<220> FEATURE:
<221> NAME/KEY: MISC_FEATURE
<222> LOCATION: (18)..(18)
<223> OTHER INFORMATION: T or P
<220> FEATURE:
<221> NAME/KEY: MISC_FEATURE
<222> LOCATION: (24)..(24)
<223> OTHER INFORMATION: S or A
<220> FEATURE:
<221> NAME/KEY: MISC_FEATURE
<222> LOCATION: (28)..(28)
<223> OTHER INFORMATION: F or A or G or S
<220> FEATURE:
<221> NAME/KEY: MISC_FEATURE
<222> LOCATION: (44)..(44)
<223> OTHER INFORMATION: R or I or D
<220> FEATURE:
<221> NAME/KEY: MISC_FEATURE
<222> LOCATION: (47)..(47)

```
<223> OTHER INFORMATION: N or T or K or V
<220> FEATURE:
<221> NAME/KEY: MISC_FEATURE
<222> LOCATION: (54)..(54)
<223> OTHER INFORMATION: I or L
<220> FEATURE:
<221> NAME/KEY: misc_feature
<222> LOCATION: (55)..(55)
<223> OTHER INFORMATION: Xaa can be any naturally occurring amino
      acid
<220> FEATURE:
<221> NAME/KEY: MISC_FEATURE
<222> LOCATION: (58)..(58)
<223> OTHER INFORMATION: I or A or V or L
<220> FEATURE:
<221> NAME/KEY: MISC_FEATURE
<222> LOCATION: (58)..(58)
<223> OTHER INFORMATION: I or F or T or L
<220> FEATURE:
<221> NAME/KEY: MISC_FEATURE
<222> LOCATION: (64)..(64)
<223> OTHER INFORMATION: H or Y or N or L
<220> FEATURE:
<221> NAME/KEY: MISC_FEATURE
<222> LOCATION: (65)..(65)
<223> OTHER INFORMATION: F or C or T or L
<220> FEATURE:
<221> NAME/KEY: MISC_FEATURE
<222> LOCATION: (75)..(75)
<223> OTHER INFORMATION: F or V or T or L
<220> FEATURE:
<221> NAME/KEY: MISC_FEATURE
<222> LOCATION: (76)..(76)
<223> OTHER INFORMATION: Q or V or T or S
<220> FEATURE:
<221> NAME/KEY: MISC_FEATURE
<222> LOCATION: (87)..(87)
<223> OTHER INFORMATION: Q or I or K or R
<220> FEATURE:
<221> NAME/KEY: MISC_FEATURE
<222> LOCATION: (91)..(91)
<223> OTHER INFORMATION: Y or I or L or H
<220> FEATURE:
<221> NAME/KEY: MISC_FEATURE
<222> LOCATION: (103)..(103)
<223> OTHER INFORMATION: A or G
<220> FEATURE:
<221> NAME/KEY: misc_feature
<222> LOCATION: (106)..(106)
<223> OTHER INFORMATION: Xaa can be any naturally occurring amino
      acid
<220> FEATURE:
<221> NAME/KEY: misc_feature
<222> LOCATION: (108)..(108)
<223> OTHER INFORMATION: Xaa can be any naturally occurring amino
      acid
<220> FEATURE:
<221> NAME/KEY: MISC_FEATURE
<222> LOCATION: (110)..(110)
<223> OTHER INFORMATION: H or R
<220> FEATURE:
<221> NAME/KEY: MISC_FEATURE
<222> LOCATION: (112)..(112)
<223> OTHER INFORMATION: Q or G or A or H
<220> FEATURE:
<221> NAME/KEY: MISC_FEATURE
<222> LOCATION: (115)..(115)
<223> OTHER INFORMATION: E or G or A or K
<220> FEATURE:
<221> NAME/KEY: MISC_FEATURE
<222> LOCATION: (120)..(120)
<223> OTHER INFORMATION: I or G or A or F
<220> FEATURE:
<221> NAME/KEY: MISC_FEATURE
<222> LOCATION: (127)..(127)
<223> OTHER INFORMATION: L or S or A or T
<220> FEATURE:
<221> NAME/KEY: MISC_FEATURE
<222> LOCATION: (128)..(128)
```

-continued

```
<223> OTHER INFORMATION: I or V
<220> FEATURE:
<221> NAME/KEY: MISC_FEATURE
<222> LOCATION: (134)..(134)
<223> OTHER INFORMATION: Q or L or I or V
<220> FEATURE:
<221> NAME/KEY: misc_feature
<222> LOCATION: (142)..(142)
<223> OTHER INFORMATION: Xaa can be any naturally occurring amino
      acid
<220> FEATURE:
<221> NAME/KEY: MISC_FEATURE
<222> LOCATION: (143)..(143)
<223> OTHER INFORMATION: E or K or G or D
<220> FEATURE:
<221> NAME/KEY: MISC_FEATURE
<222> LOCATION: (150)..(150)
<223> OTHER INFORMATION: L or Q

<400> SEQUENCE: 51

Met Cys Cys His Ile His Ile Gln Cys Phe Xaa Xaa Xaa Xaa Met Ala
1               5                   10                  15

Gly Xaa Ile Lys Ala Leu Ile Xaa Leu Ser Phe Xaa Gly Ala Ile Gly
            20                  25                  30

Leu Thr Phe Leu Met Leu Gly Cys Ala Leu Pro Xaa Tyr Gly Xaa Tyr
        35                  40                  45

Trp Pro Leu Phe Val Xaa Xaa Phe Tyr Xaa Leu Ser Pro Ile Pro Xaa
    50                  55                  60

Xaa Ile Ala Arg Arg Gly Asn Lys Tyr His Xaa Xaa Asp Asp Met Asp
65                  70                  75                  80

Ala Thr Ser Asn Ala Cys Xaa Glu Leu Ala Xaa Phe Leu Thr Thr Gly
                85                  90                  95

Ile Val Val Ser Ala Phe Xaa Leu Pro Xaa Val Xaa Ala Xaa Ala Xaa
            100                 105                 110

Leu Ile Xaa Trp Gly Ala Cys Xaa Leu Val Leu Ile Gly Asn Xaa Xaa
        115                 120                 125

Ile Phe Ser Thr Ile Xaa Gly Phe Phe Leu Ile Phe Gly Xaa Xaa Asp
    130                 135                 140

Asp Phe Ser Trp Ser Xaa Trp Gly
145                 150
```